US006544519B1

(12) United States Patent
Tokunaga et al.

(10) Patent No.: US 6,544,519 B1
(45) Date of Patent: *Apr. 8, 2003

(54) **POLYPEPTIDE ORIGINATING IN *HAEMOPHILUS PARAGALLINARUM* AND PROCESS FOR PRODUCING THE SAME**

(75) Inventors: Eiji Tokunaga, Kumamoto (JP); Masashi Sakaguchi, Kumamoto (JP); Kazuo Matsuo, Kumamoto (JP); Fukusaburo Hamada, Kumamoto-ken (JP); Sachio Tokiyoshi, Kumamoto (JP)

(73) Assignee: Juridical Foundation The Chemo-Suro-Therapeutic Research Institute, Kumamoto-ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/077,098

(22) PCT Filed: Sep. 17, 1997

(86) PCT No.: PCT/JP97/03222

§ 371 (c)(1),
(2), (4) Date: May 19, 1998

(87) PCT Pub. No.: WO98/12331

PCT Pub. Date: Mar. 26, 1998

(30) Foreign Application Priority Data

Sep. 19, 1996 (JP) .............................................. 8-271408

(51) Int. Cl.$^7$ ........................ A61K 39/38; A61K 39/00; A61K 39/02; A61K 39/102; C12N 1/00
(52) U.S. Cl. .............................. 424/185.1; 424/184.1; 424/190.1; 424/234.1; 424/256.1; 435/851
(58) Field of Search .......................... 424/229.1, 256.1, 424/803, 184.1, 185.1, 190.1, 234.1; 530/319, 350; 435/851

(56) References Cited

U.S. PATENT DOCUMENTS

| | | | | |
|---|---|---|---|---|
| 4,247,539 A | * | 1/1981 | Iritani et al. ................... | 424/92 |
| 4,746,613 A | * | 5/1988 | Wichmann ................... | 435/253 |
| 5,196,514 A | * | 3/1993 | Avakian et al. .............. | 530/350 |
| 5,240,705 A | * | 8/1993 | Jacobs ........................... | 424/88 |
| 5,650,153 A | * | 7/1997 | Ishikawa et al. .......... | 424/229.1 |

FOREIGN PATENT DOCUMENTS

| JP | 5645416 | 4/1981 |
|---|---|---|
| JP | 56115724 | 9/1981 |
| JP | 64000467 | 1/1989 |
| JP | 5112466 | 5/1993 |
| JP | 8027028 | 1/1996 |

OTHER PUBLICATIONS

Database SRS Fleischmann, et al., "Haemophilus Influenzae Genome." Database accession No. U32845 (1995).
Ben–Yehuda, et al., "Recombinant Vaccinia Virus With Influenza Hemagglutinin Protects Old Mice from Influenza Infection," Transactions of the Association of American Physicians. 105:177–181 (1992).
Ohuchi, et al., "Mutations at the Cleavage Site of the Hemagglutinin Alter the Pathogenicity of Influenza Virus A/Chick/Penn/83 (H5N2)." Virology. 168:274–280 (1989).
Jacobs, et al., "Efficacy of a trivalent *Haemophilus paragallinarum* vaccine compared to bivalent vaccines." Veterinary Microbiology. 32:43–49 (1992).
Kume et al. 1980. Immunologic Relationship between Page's and Sawata's Serotype Strains of *Haemophilus paragallinarum*. Am. J.Vet. Res. 41:757–760.*
Sawata et al. 1980. Biologic and Immunologic Studies on Three Types of Hemagglutinin of *Haemophilus paragallinarum* Serotype 1 Organisms. Am/ J. Vet. Res. 41:1901–1904.*
Yamaguchi et al. 1988. Serological Response of Chickens Either vaccinated or Artificially Infected with *Haemophilus paragallinarum*. Avain Disease. 32:308–312.*
Iritani et al. 1988. Purification and Properties of *Haemophilus paragallinarum* Hemagglutinin. Am J. Vet. Res. 41:2114–2118.*
Takagi et al. 1993. Purification of Hemagglutinin from *Haemophilus paragallinarum* using monoclonal antibody. Vet. Microbio. 34:191–197.*
Matsumoto, M. et al., "A Broth Bactern Against Infectious Coryza: Immunogenicity of Various Preparations," *Avian Diseases*, 18:109–177 (1971).
Otsuki, K. et al., "Preparation and Immunological Response to a New Mixed Vaccine Composed of Inactivated Newcastle Disease Virus, Inactivated Infectious Bronchitis Virus, and Inactivated Hemophilus Gallinarum," *Avian Diseases*, 18–3:297–304 (1974).
Kume, K. et al., "Clearance of the Challenge Organisms from the Upper Respitory Tract of Chickens Injected with an Inactivated *Haemophilus paragallinarum* Vaccine," *Jpn. J. Vet. Sci.*, 46:843–850 (1984).

(List continued on next page.)

*Primary Examiner*—Mark Navarro
*Assistant Examiner*—Jana Hines
(74) *Attorney, Agent, or Firm*—Browdy and Neimark, PLLC

(57) ABSTRACT

A novel peptide obtained from *Haemophilus paragallinarum* has been found useful for preventing avian infectious coryza. This polypeptide induces production of hemagglutination-inhibition antibody and prevents infection and onset of avian infectious coryza. The invention further provides a gene coding for the polypeptide, a recombinant vector for expression of this gene, a host transformed with this vector, a process for preparing the polypeptide in a host, a vaccine for avian infectious coryza comprising the polypeptide as an active ingredient, a monoclonal antibody obtained using the polypeptide as an immunogen, and a diagnostic agent and a therapeutic agent for avian infectious coryza using the peptide and the antibody.

2 Claims, 12 Drawing Sheets

OTHER PUBLICATIONS

Page, L. A., "Haemophilus Infections in Chickens. I. Characteristics of 12 Haemophilus Isolates Recovered from Diseased Chickens," *Am. J. Vet. Res.*, 23:85–95 (1962).

Sawata A., et al., "Haemophilus Infections in Chickens 2. types of *Haemophilus paragallinarum* Isolates from Chickens with Infectious Coryza, in Relation to Haemophilus gallinarum Strain No. 221," *Jpn. J. Vet. Sci.*, 40:645–652 (1978).

Kume, K. et al., "Immunologic Relationship Between Page's and Sawata's Serotype Strains of *Haemophilus paragallinarum*," *Am. J. Vet. Res.*, 41:757–760 (1980).

Sawata, A. et al., "Biologic and Serologic Relationships Between Page's and Sawata's Serotypes of *Haemohilus paragallinarum*," *Am. J. Vet. Res.*, 41:1901–1904 (1980).

Kume, K. et al., "Serologic amd Immunologic Studies on Three Types of Hemagglutinin of *Haemophilus paragallinarum* Serotype 1 Organisms," *Jpn. J. Vet. Sci.*, 45:783–792 (1983).

Sawata, A. et al., "Hemagglutinins of *Haemophilus paragallinarum* Serotype 1 Organisms," *Jpn. J. Vet. Sci.*, 46:21–29 (1984).

Yamaguchi T., et al., "Occurence of Two Hemagglutinins on *Haemophilus paragallinarum* Strain 221 and Comparison of Their Properties," *Jpn. J. Vet. Sci.*, 42:709–711 (1980).

Iritani, Y., et al., "Purification and Properties of *Haemophilus paragallinarum* Hemagglutinin," *Am. J. Vet. Res.*, 41:2114–2118 (198).

Sawata, A., et al., "Hemagglutinin of *Haemophilus paragallinarum* serotype 2 organisms: Occurence and immunologic properties of hemagglutinin," *Am. J. Vet. Res.*, 43:1311–1314 (1982).

Takagi M., et al., "Purification of hemagglutinin from *Haemophilus paragallinarum* using monoclonal antibody," *Vet. Microbiol.*, 34:191–197 (1993).

* cited by examiner

Fig. 6 a)

| | 1 | 2 |
|---|---|---|
| 200Kd → | | |
| 116Kd → | | ← ← |
| 66Kd → | | |
| 42Kd → | | |
| 30Kd → | | |
| 17Kd → | | |

CBB staining b)

| | 1 | 2 |
|---|---|---|
| 202Kd → | | |
| 133Kd → | | |
| 71Kd → | | |
| 42Kd → | | |
| 31Kd → | | |
| 18Kd → | | |

Western Blot 1. purified HPGp130
2. Serotype A strain 221

Fig. 10

| | 1 | 2 | 3 | 4 | 5 | 6 | 7 | 8 | 9 |

27.7Kb →
23.1Kb →
9.4 Kb →
6.56Kb →
4.36Kb →
3.16Kb →
2.69Kb →
2.32Kb →
2.02Kb →
1.57Kb →
1.1 Kb →

1. Serotype A strain 221
2. Serotype A strain 083
3. Serotype A strain W
4. Serotype A strain Germany
5. Serotype A strain Georgia
6. Serotype B strain Spross
7. Serotype B strain 0222
8. Serotype C strain Modesto
9. Serotype C strain 53-47

1. Serotype A strain 221
2. Serotype A strain 083
3. Serotype A strain W
4. Serotype A strain Germany
5. Serotype A strain Georgia
6. Serotype B strain Spross
7. Serotype B strain 0222
8. Serotype C strain Modesto
9. Serotype C strain 53-47

POLYPEPTIDE ORIGINATING IN *HAEMOPHILUS PARAGALLINARUM* AND PROCESS FOR PRODUCING THE SAME

FIELD OF THE INVENTION

The present invention relates to a polypeptide which can prevent avian infectious coryza. More particularly, the present invention relates to a polypeptide from *Haemophilus paragallinarum*, the causative agent of avian infectious coryza, a gene coding for said polypeptide and an antibody protein which recognizes said polypeptide. The present invention further relates to a process for preparing said polypeptide and the use of said polypeptide for a vaccine, a diagnostic agent and a therapeutic agent.

BACKGROUND ART

Avian infectious coryza is one of the most important respiratory diseases in poultry, which is an acute respiratory disease caused by infection with *Haemophilus paragallinarum* (hereinafter also referred to as "HPG") with cardinal symptoms being a running nose, swelling of the face and epiphora. Avian infectious coryza brings about a great economical damage since it leads to decrease in the breeding rate of poultry, retarding of egg laying, decrease in egg production or failure of egg laying. For prevention of avian infectious coryza, an inactivated vaccine has hitherto been used widely which is obtained by culturing *Haemophilus paragalinarum*, recovering and inactivating the cells with formalin, thimerosal and the like. However, adverse side effects caused by such an inactivated vaccine has been an issue as it has been reported that local necrotic lesions are formed in the inoculated chicken when the vaccine is administered (M. Matsumoto and R. Yamamoto, Avian Dis., 15: 109–117, 1971), and hence, development of a highly safe vaccine is earnestly desired.

In recent years, laborsaving in breeding and managing poultry is in progress with a scale-up of breeding poultry. As a part of this, laborsaving in vaccination has also been earnestly desired, and as a result, a mixed vaccine has already been developed and widely used in the field so that a frequency of inoculation can be reduced by mixing several kinds of vaccines together.

In order to provide a mixed vaccine showing immunogenicity equivalent to that of each plain vaccine without increase of dosage amount, it is necessary to increase an amount of each antigen contained in a mixed vaccine or to find out and use a more suitable adjuvant. However, in case of gram-negative bacteria such as HPG, a higher amount of antigen is likely to enhance a response to injection such as swelling at the inoculated site. Therefore, in order to reduce such an adverse response, it is preferable to obtain only a protective antigen, i.e. an effective component, from bacterial cells or culture supernatant, or to clone a gene coding for said antigen by the genetic recombination technique, to express said gene in bacteria, yeast, an animal cell, a plant cell, an insect cell and the like, and to purify a product expressed in a large amount, which is then mixed with an appropriate adjuvant together with other vaccines.

Another approach for laborsaving of vaccination is the use of virus or bacteria as a vector. That is, genes coding for protective antigens from one or plural pathogens have been incorporated into an attenuated virus or bacteria to prepare a polyvalent live vaccine. For fowls, poxvirus, Marek's disease virus and the like have been investigated as a vector. A vaccine comprising a viral vector has been put into practice wherein genes coding for HN and F proteins of Newcastle disease virus are incorporated into fowl pox virus.

It is thus most important to identify a protective antigen of HPG for development of a safe and effective vaccine against avian infectious coryza both as a component vaccine and as a vector vaccine.

Among protective antigens of HPG such as hemagglutinin (HA) and outer-membrane protein, HA is considered a most important antigen since immunization of chicken with HPG increases a hemagglutination-inhibition antibody (hereinafter referred to as "HI antibody") and higher protective effect is observed for chickens with high level of HI antibody (K. Otsuki and Y. Iritani, Avian Dis., 18: 297–304, 1974 and K. Kume et al., Jpn. J. Vet. Sci., 46: 843–850, 1984).

Serotype of HPG is classified into serotypes A, B and C (Page, Am. J. Vet. Res., 23: 85–95, 1962) or into serotypes 1 and 2 (Sawata et al., Jpn. J. Vet. Sci., 40: 645–652, 1978) based on the agglutination test. It is considered that serotype A by Page corresponds to serotype 1 by Sawata et al. whereas serotype C by Page corresponds to serotype 2 by Sawata et al. (K. Kume, et al., Am. J. Vet. Res., 41: 757–760, 1980 and Sawata et al., Am. J. Vet. Res., 41: 1901–1904, 1980).

Kume et al. reported that HPG serotype A (serotype 1) has at least three kinds of HA, i.e. HA-L (heat-labile, trypsin-sensitive), HA-HL (heat-labile, trypsin-resistant) and HA-HS (heast-stable, trypsin-resistant), and that HA-L alone exhibits not only HA activity to usual fresh chicken erythrcytes but also to glutaraldehyde-fixed chicken erythrocytes and is involved in protection against infection with HPG serotype A (K. Kume, Jpn. J. Vet. Sci., 45: 783–792, 1983 and Sawata et al., Jpn. J. Vet. Sci., 46: 21–29, 1984).

Iritani et al. reported that HPG serotype A has two kinds of HA, i.e. type 1 HA (heat-labile, protease-sensitive) and type 2 HA (heat-labile, protease-resistant), and that type 1 HA, which is heat-labile and protease-sensitive and consisted of a polypeptide having a molecular weight of about 39 kd as a subunit, is involved in protection against infection (T. Yamaguchi and Y Iritani, Jpn. J. Vet. Sci., 42: 709–711, 1980 and Y. Iritani et al., Am. J. Vet. Res., 41: 2114–2118, 1980). It is considered that HA-L and HA-HL by Kume et al. correspond to type 1 HA and type 2 HA by Iritani et al., respectively. As to HPG serotype C (serotype 2), Sawata et al. reported that an antigen was found which is heat-labile and trypsin-sensitive and exhibits the HA activity to glutaraldehyde-fixed chicken erythrocytes and that this antigen is distinct from HA of HPG serotype A in their antigenicity (Sawata et al., Am. J. Vet. Res., 43: 1311–1314, 1982). However, to date, a protective antigen of HPG has not yet seen materially identified except for type 1 HA produced by HPG serotype A as reported by Iritani et al.

As mentioned hereinabove, the conventional inactivated vaccine obtained by inactivating *Haemophilus paragalinarum* cells with thimerosal, formalin and the like has provoked problems in that the adverse side effects as mentioned above are induced when it is applied to fowls in a large amount since it includes various substances from the cells other than the protective antigen.

DISCLOSURE OF INVENTION

The inventor has earnestly studied in order to solve the problems, and as a result, has successfully purified, from a culture supernatant of *Haemophilus paragallinarum* serotype A, a polypeptide having about 130 kd of molecular weight from *Haemophilus paragallinarum* serotype A, said polypeptide inducing production of HI antibody and protecting against avian infectious coryza by *Haemophilus paragallinarum* serotype A.

Furthermore, the present inventor has prepared a genomic DNA library from HPG serotype A, cloned a gene fragment coding for the above 130 Kd polypeptide, expressed said gene fragment in *E. coli* and has found that the produced polypeptide could prevent avian infectious coryza by *Haemophilus paragallinarum* serotype A. Said gene fragment coding for the above 130 Kd polypeptide was also used as a probe for cloning a gene fragment hybridizable with said DNA fragment from HPG serotype C to give *E. coli* which expresses the polypeptide from HPG serotype C.

The present invention provides a safer, effective vaccine against avian infectious coryza, pathogenic bacteria of which is *Haemophilus paragallinarum*, with less adverse side effects and a process for preparing the same.

That is, an object of the present invention is to provide a novel polypeptide from *Haemophilus paragallinarum* as well as a peptide which shares at least a portion of the amino acid sequence.

Another object of the present invention is to provide a gene coding for said novel polypeptide from *Haemophilus paragallinarum* as well as the peptide which shares at least a potion of the amino acid sequence and a recombinant vector for expression of said gene.

Still another object of the present invention is to provide a process for preparing said novel polypeptide from *Haemophilus paragallinarum* and the polypeptide which shares at least a portion of the amino acid sequence from microorganisms or cells transformed with said recombinant vector.

Still further object of the present invention is to provide a monoclonal or polyclonal antibody which is prepared by using as an immunogen the thus prepared novel peptide from *Haemophilus paragallinarum* or the polypeptide which shares at least a portion of the amino acid sequence.

Still another object of the present invention is to provide a method for detecting *Haemophilus paragallinarum* or an antibody thereto by a combination of the above-mentioned peptide, DNA fragment, transformant or antibody.

Still further object of the present invention is to provide a therapeutic agent for avian infectious coryza which comprises as an active ingredient the antibody against the novel polypeptide from *Haemophilus paragallinarum*.

BRIEF DESCRIPTION OF DRAWINGS

FIG. 6 is (a) a photograph showing the results of SDS-PAGE electrophoresis with CBB staining of the purified HPGp130 polypeptide and *Haemophilus paragallinarum* serotype A strain 221 treated with 2-mercaptoethanol; and (b) a photograph showing the results of detection of proteins reactive with guinea pig antiserum against the purified HPGp130 polypeptide after SDS-PAGE electrophoresis of the purified HPGp130 polypeptide and *Haemophilus paragallinarum* serotype A strain 221 treated with 2-mercaptoethanol and transferring to a thin membrane (PVDF).

FIG. 10 is a photograph showing the results of detection of DNA fragments hybridizable with HPG1.2 k DNA as a probe after agarose electrophoresis of DNA fragments obtained by digesting the genome from *Haemophilus paragallinarum* serotypes A, B and C with restriction enzyme EcoRI and transferring to a thin membrane (Hybond N+).

BEST MODE FOR CARRYING OUT THE INVENTION

Figure 1:
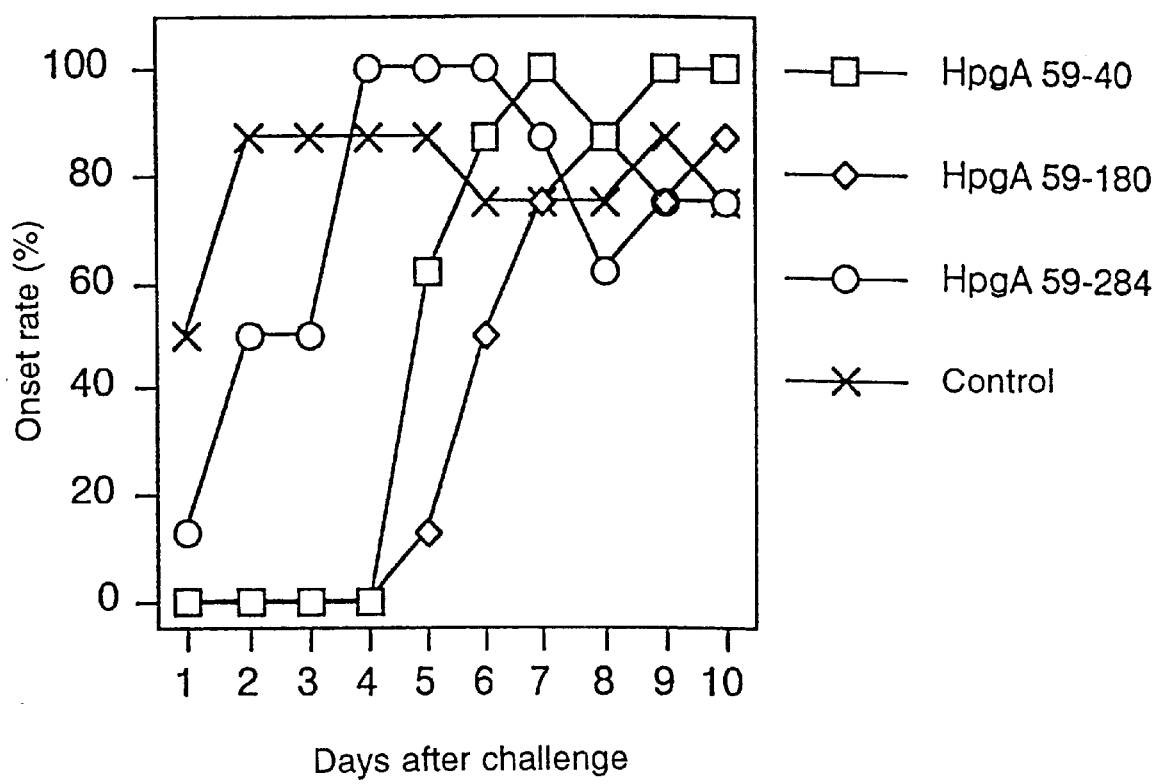
FIG. 1 shows the results obtained by challenging chickens with *Haemophilus paragallinarum* serotype A strain 221 after passive immunization with monoclonal antibodies (clones HpgA 59-40, HpgA 59-180 and HpgA 59-284) wherein the onset of the disease was retarded in the groups previously administered with the monoclonal antibodies having the HI activity (clones HpgA 59-40 and HpgA 59-180).
Figure 2:
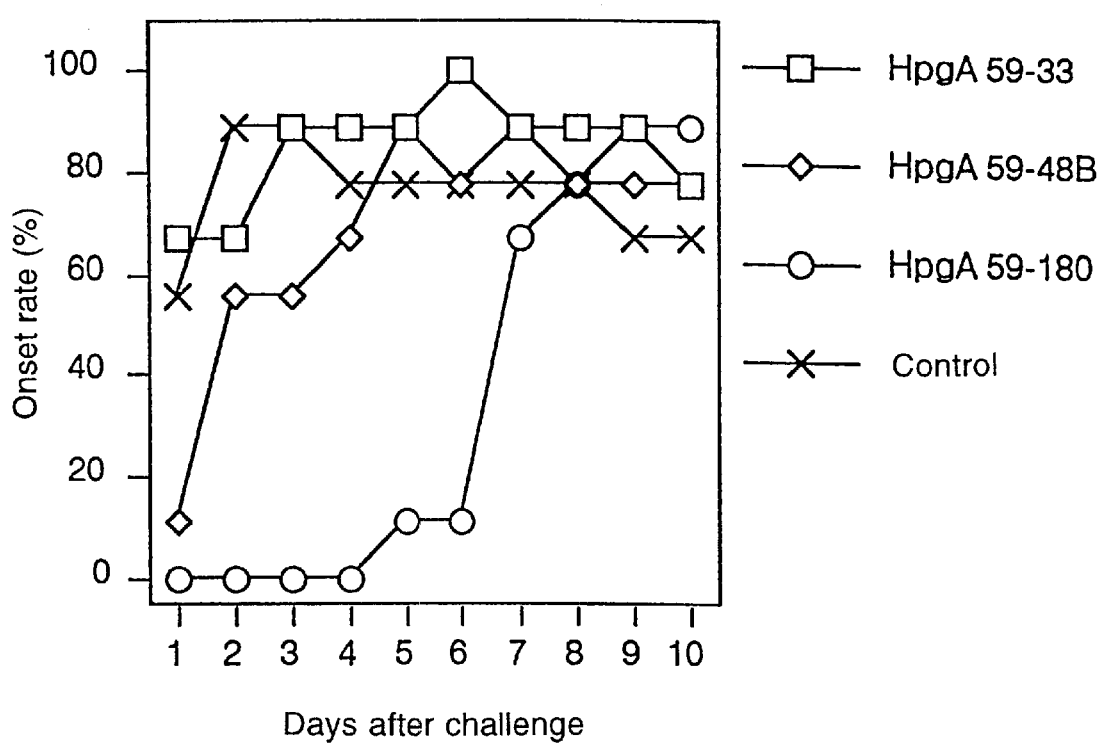
FIG. 2 shows the results obtained by challenging chickens with *Haemophilus paragallinarum* serotype A strain 221 after passive immunization with monoclonal antibodies (clones HpgA 59-33, HpgA 59-48B and HpgA 59-180) wherein the onset of the disease was retarded in the groups previously administered with the monoclonal antibody having the HI activity (clone HpgA 59-180).
Figure 3:
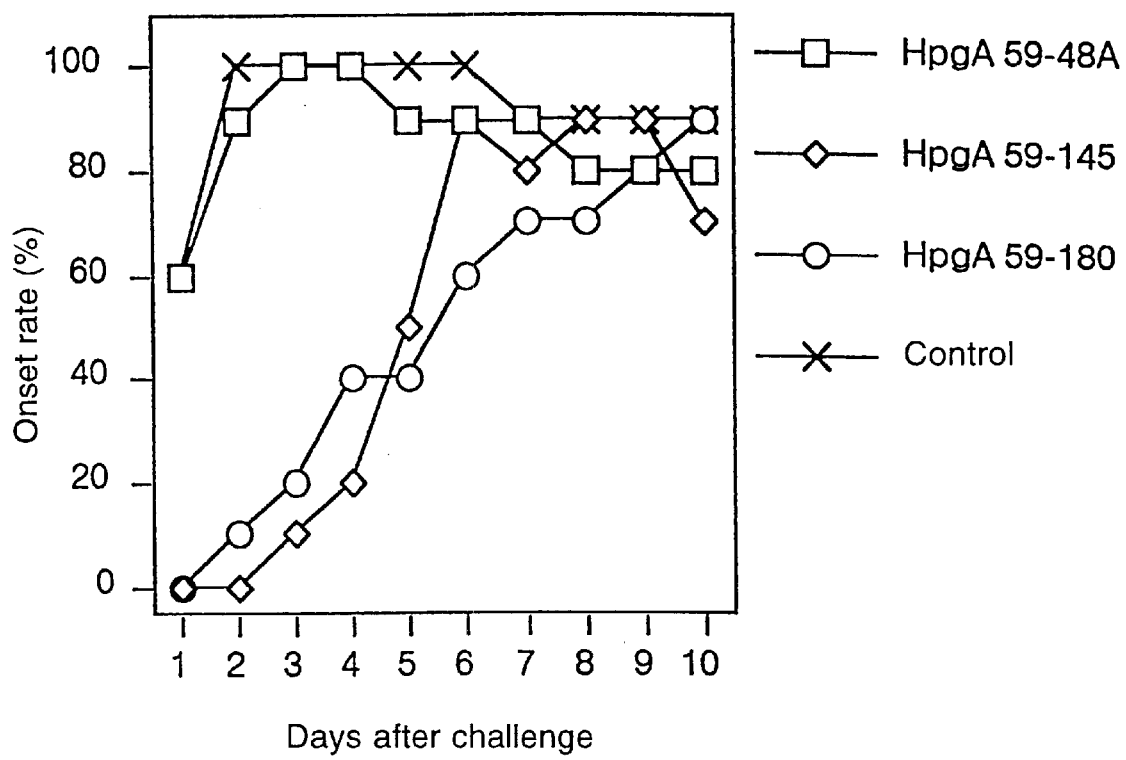
FIG. 3 shows the results obtained by challenging chickens with *Haemophilus paragallinarum* serotype A strain 221 after passive immunization with monoclonal antibodies (clones HpgA 59-48A, HpgA 59-145 and HpgA 59-180) wherein the onset of the disease was retarded in the groups previously administered with the monoclonal antibodies having the HI activity (clones HpgA 59-145 and HpgA 59-180).
Figure 4:
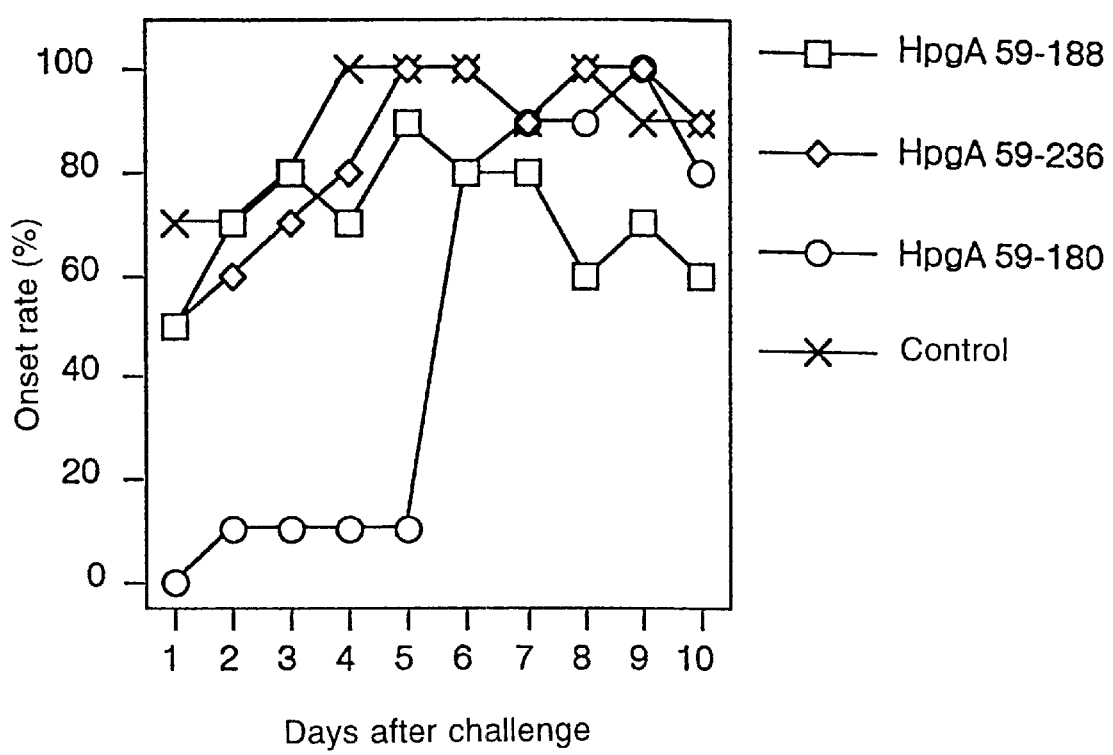
FIG. 4 shows the results obtained by challenging chickens with *Haemophilus paragallinarum* serotype A strain 221 after passive immunization with monoclonal antibodies (clones HpgA 59-188, HpgA 59-236 and HpgA 59-180) wherein the onset of the disease was retarded in the groups previously administered with the monoclonal antibody having the HI activity (clone HpgA 59-180).

The present invention is explained in more detail hereinbelow.

The polypeptide from *Haemophilus paragallinarum* serotype A of the present invention which induces production of the HI antibody is prepared from a culture supernatant of HPG serotype A or a suspension of ruptured cells by affinity chromatography with the monoclonal antibody having the HI activity as a ligand.

The monoclonal antibody having the HI activity (hereinafter also referred to as "HI-MCA") is obtained by preparing the hybridomas producing the monoclonal antibodies which bind to *Haemophilus paragallinarum* serotype A by the conventional cell fusion procedure and then screening the hybridoma producing the monoclonal antibody having the HI activity with HI test.

For use as an immunogen for production of the above antibody, *Haemophilus paragallinarum* serotype A is obtained by the conventional procedure used for usual culture of *Haemophilus paragallinarum*. For example, the cells of HPG strain 221 can be recovered by shaking culture in a chicken meat infusion medium supplemented with chicken serum (including chicken meat infusion 300 ml, chicken serum 10 ml, polypeptone 5 g, glucose 1 g, casamino acid 1 g, sodium glutamate 5 g, sodium chloride 5 g, nicotinamide adenine dinucleotide 0.025 g in 1000 ml medium) at 37° C. overnight followed by centrifugation.

Immunization can be carried out in a usual manner, for example, after inactivating *Haemophilus paragallinarum* serotype A with thimerosal, formalin and the like, by administering the inactivated cells together with the conventional adjuvant to BALB/c mouse via intraperitoneal, subcutaneous, intradermal or intravenous administration. The immunogen includes HPG cells per se, or alternatively, the cells treated with potassium rhodanide, sonication or hyaluronidase, or a processed antigen obtained by treatment with a surf actant such as sodium N-lauroylsarcosinate, NONIDET P-40 or TRITON X-100. The adjuvant includes Freund's complete adjuvant, Freund's incomplete adjuvant, aluminum hydroxide gel, and the like. More specifically, immunization is conducted as follows: *Haemophilus paragallinarum* serotype A strain 221 cultured in a chicken meat infusion medium supplemented with chicken serum is inactivated with thimerosal and then sonicated. An emulsion obtained by mixing the resultant suspension of ruptured cells with Freund's complete adjuvant is administered subcutaneously to the back of BALB/c mouse, followed by subcutaneous administration of an emulsion prepared from the same amount of the suspension and Freund's incomplete adjuvant at the back every 2 to 4 weeks. A serum antibody level is monitored, and after confirming the elevated level of antibody titer, a suspension of ruptured cells after sonication is further administered intravenously after additional 2 to 4 weeks as a final immunization.

As an immunocyte for preparing a monoclonal antibody, splenocytes removed 2 to 4 days after the final administration is preferably used. Mouse myeloma cells include, for example, NSI-Ag4/1 (Eur. J. Immunol., 6: 511, 1976), P3X63-Ag8.U1 (Curr. Topics Microbiol. Immunol., 81:1, 1978), X63-Ag8.653 (J. Immunol., 123: 1548, 1979), and the like. Fusion of splenocytes with mouse myeloma cells may be carried out in accordance with Milstein et al., Method Enzymol., 73, 3–46,1981. That is, fusion can be carried out with approximately 1 to 10 folds higher amount of splenocytes than mouse myeloma cells. A cell fusion promoting agent may be polyethylene glycol having a molecular weight of 1,000–6,000 at a concentration of 30 to 50% (w/v). More specifically, cell fusion is preferably carried out with about $10^8$ splenocytes and about $10^7$ P3X63-Ag8.U1 myeloma cells in a culture medium usually used for culture of lymphocytes such as RPMI 1640 medium, containing 45% polyethylene glycol 4,000, which is previously heated at 37° C.

Hybridoma may be obtained by culture in HAT medium for a sufficient period of time so that the non-fused cells cannot survive, usually for several days to several weeks. The thus obtained hybridomas are then used for selection and cloning of strains producing a desired antibody in accordance with the usual limiting dilution procedure, using the culture supernatant of the hybridomas.

Screening of strains producing an antibody recognizing *Haemophilus paragallinarum* serotype A is carried out in accordance with the usual ELISA, RIA, Western blotting, and the like. An antigen used in these methods may be either a suspension of *Haemophilus paragallinarum* serotype A cells, the cells treated with potassium rhodanide, sonication, hyaluronidase, and the like, or an extraction of said cells with a surfactant.

Then, strains producing an antibody having the HI activity are screened in accordance with the usual HI test, using a culture supernatant of the above hybridomas or ascites from mouse administered with said hybridomas. HA antigen includes a suspension of *Haemophilus paragallinarum* cells or the cells treated with potassium rhodanide, sonication, hyaluronidase, and the like. Erythrocytes used for HI test may be either 0.5% fresh chicken erythrocytes, glutaraldehyde-fixed 1% chicken erythrocytes or formalin-fixed chicken erythrocytes, with glutaraldehyde-fixed chicken erythrocytes being preferable.

More specifically, a supernatant obtained after centrifugation of ascites treated with 5 folds amount of a 25% kaolin solution is added to precipitates of glutaraldehyde-fixed chicken erythrocytes, which is then shaken at 37° C. for 60 minutes for sensitization. To a two-fold serial dilution of this supernatant is added the same amount of a suspension of strain 221 cells including 4 hemagglutinin units and the mixture is left to stand for 15 minutes. Thereto is added a suspension of glutaraldehyde-fixed 1% chicken erythrocytes, the mixture is left to stand at room temperature for 60 minutes, and observed at the bottom of microtiter plate. An HI antibody titer is defined as a maximum dilution which can block hemagglutination.

Recovery of monoclonal antibodies having the HI activity from the thus obtained hybridomas is carried out by culturing said hybridomas in a large amount and harvesting said antibodies from the culture supernatant, or by administering said hybridomas to mice compatible with said hybridomas so that said hybridomas are proliferated and harvesting said antibodies from the ascites thereof.

Purification of the monoclonal antibody may be done by the conventional procedures used in the protein chemistry such as, for example, a salting out, ultrafiltration, an isoelectric precipitation, an electrophoresis, an ion exchange chromatography, a gel filtration chromatography, an affinity chromatography, and the like. More specifically, purification of the monoclonal antibody from ascites may be done using Protein A-Sepharose CL-4B (manufactured by Pharmacia) and MAPS-II Mouse Monoclonal Antibody Purification Kit (manufactured by Bio Rad) in accordance with protocol of the manufacturer.

An affinity column with the antibody having the HI activity as a ligand for purification of the polypeptide from Haemophilus paragallinarum serotype A which induces production of the HI antibody may be prepared by a conventional procedure, for example, by binding the above purified antibody to HiTrap NHS-Activated Column (manufactured by Pharmacia) in accordance with protocol of the manufacturer.

Using the thus prepared affinity column, the polypeptide from *Haemophilus paragallinarum* serotype A which induces production of the HI antibody may be obtained from a culture supernatant of HPG serotype A cells or from a suspension of ruptured cells. Specifically, a polypeptide (hereinafter referred to as "HPGp130") with a molecular weight of about 130 Kd having a high capacity to produce the HI antibody and the activity to prevent avian infectious coryza was obtained from a culture supernatant of HPG strain 221 cultured in the chicken meat infusion medium supplemented with chicken serum at 37° C. for two days.

An amino acid sequence of the thus obtained polypeptide may be determined by the usual procedures such as Edman degradation (P. Edman, Acta Chem. Scand., 4: 283, 1950). The amino acid sequence at the N-terminal of said polypeptide is shown in SEQ ID NO: 2.

Cloning of a gene or a gene fragment coding for the polypeptide from *Haemophilus paragallinarum* serotype A may be done by the usual procedures as described by Sambrook et al. (Molecular Cloning, A Laboratory Manual, 2nd Edition, Cold Spring Harbor Laboratory Press, New York, 1989). That is, *Haemophilus paragallinarum* serotype A strain 221 cells are cultured and recovered by the above procedures, a genomic DNA is extracted and purified with Sepagene kit (manufactured by Sanko Junyaku K.K.) in accordance with protocol attached thereto. The genomic DNA is then cleaved with a commercially available restriction enzyme (preferably EcoRI), the obtained DNA fragments are inserted into a commercially available cloning vector (e.g. λgt11) to prepare a DNA library, among which such clones expressing the antigen that responds to the desired antibody having the HI activity are screened. The antibody having the HI activity includes the culture supernatant of the hybridomas or the ascites of mice obtained as mentioned above. Antisera is preferably used which is obtained by immunization with the polypeptide from *Haemophilus paragallinarum* serotype A isolated by affinity chromatography with the monoclonal antibody having the HI activity as a ligand. A nucleotide sequence of the exogenous DNA fragment in the thus obtained recombinant λgt11 phage DNA may be determined with a DNA sequencer (for example, Applied Biosystems 377). Novelty of the obtained exogenous DNA fragment may be confirmed by homology search between the whole nucleotide sequence and the existing data base (for example, GeneBank, EMBL, and the like).

As shown in Example 3, for example, ten positive λgt11 phages were obtained from the DNA library and each DNA of these phages included an exogenous DNA fragment of about 1.2 kb (hereinafter also referred to as "HPG1.2 k DNA fragment") as demonstrated in an agarose electrophoresis. The nucleotide sequence of said exogenous DNA corresponds to the nucleotide sequence of from nucleotides No. 1988 to No. 3157 of SEQ ID NO: 1.

Since an initiation codon and a termination codon are not found in the HPG1.2 k DNA, this DNA fragment is considered to encode a portion of the polypeptide from *Haemophilus paragallinarum* serotype A. A gene coding for a full length of said polypeptide may be obtained by using the HPG1.2 k DNA as a probe to give a longer DNA fragment, determining a nucleotide sequence of this DNA fragment and finding out an initiation codon and a termination codon.

More specifically, the genomic DNA of *Haemophilus paragallinarum* serotype A strain 221 is cleaved with a restriction enzyme whose cleavage site is not present in the 1.2 kb DNA (for example, HindIII) and the resulting DNA fragments are separated with an agarose electrophoresis. Using DIG-DNA Labeling Kit (manufactured by Boehringer Mannheim), Southern hybridization is carried out using digoxigenin (DIG)-labeled 1.2 kb DNA fragment as a probe for detecting desired DNA fragments. As a result, there was obtained a HindIII-digested DNA fragment of about 3.5 kb which hybridized with the 1.2 kb DNA fragment (hereinafter also referred to as "HPG3.5 k DNA fragment"). A nucleotide sequence of the HPG3.5 k DNA fragment corresponds to the nucleotide sequence of from nucleotides No. 1 to No. 3450 of SEQ ID NO: 1. An identical sequence to the amino acid sequence at the N-terminal of the above HPGp130 polypeptide was found at the amino acid sequence of from amino acid residues No. 1 to No. 13 (corresponding to nucleotide sequence of from No. 453 to No. 491) in SEQ ID NO: 1.

Since only an initiation codon was found in the HPG3.5 k DNA but a termination codon was not, the 1.2 kb DNA fragment and the 3.5 kb DNA fragment labeled with DIG were used as a probe to give a XhoI-XbaI digested DNA fragment of about 4.1 kb (hereinafter also referred to as "HPG4.1 k DNA fragment"). A nucleotide sequence of the HPG4.1 k DNA fragment corresponds to the nucleotide sequence of from nucleotides No. 2212 to No. 6275 of SEQ ID NO: 1. Since a termination codon was not found in the HPG4.1 k DNA fragment, a XhoI-PstI digested DNA fragment of about 6.7 kb (hereinafter also referred to as "HPG6.7 k DNA fragment"; this fragment encompasses the above HPG4.1 k DNA fragment) was obtained using the 1.2 kb DNA and the 3.5 kb DNA labeled with DIG. A nucleotide sequence of the HPG6.7 k DNA fragment corresponds to the nucleotide sequence of from nucleotides No. 2212 to No. 8930 of SEQ ID NO: 1. There existed a termination codon in the HPG6.7 k DNA fragment.

It was found that the nucleotide sequence of SEQ ID NO: 1, consisting of a total of 8930 nucleotides, included an open reading frame starting from nucleotide No. 243 which can code for 2042 amino acid residues (SEQ ID NO:6). A polypeptide comprising the 2042 amino acid residues is hereinafter also referred to as "serotype A HMTp210". Homology search with the existing data base (GeneBank and EMBL) revealed no homology with any known nucleotide and amino acid sequences, indicating that the serotype A HMTp120 polypeptide is a novel substance.

The presence of another possible open reading frame in the nucleotide sequence of SEQ ID NO: 1 was also suggested which starts from nucleotide No. 8375 and can code for 185 amino acid residues (SEQ ID NO: 8). No termination codon was found-in this sequence. Homology search with the existing data base (GeneBank and EMBL) revealed no homology with any known nucleotide and amino acid sequences, indicating that the polypeptide coded by this open reading frame is also a novel substance.

The DNA fragments from *Haemophilus paragallinarum* serotype A can also be used as a probe for obtaining DNA fragments from different serotype of *Haemophilus paragallinarum* such as serotype B or serotype C as well as polypeptides coded by said DNA fragments.

More specifically, a genomic DNA is extracted and purified from HPG serotype C strain 53-47 and cleaved with a suitable restriction enzyme (preferably HindIII), the obtained DNA fragments are inserted into a commercially available cloning vector (e.g. λDASHII) to prepare a DNA library, among which clones are screened by using the serotype A HPG3.5 k DNA fragment labeled with DIG as a probe.

As shown in Example 5, ten positive λDASHII phages were obtained from the DNA library and each DNA of these phages included an exogenous DNA fragment of about 13.5 kb (hereinafter also referred to as "HPG-C1 DNA") as demonstrated in an agarose electrophoresis.

Since the HPG-C1 DNA fragment of about 13.5 kb is too large to be subcloned into a plasmid vector, it was cleaved with a suitable restriction enzyme (preferably XbaI) and the resulting DNA fragments were inserted into a commercially available cloning vector (for example, pUC119). As a result, DNA fragments of about 5.6 kb (hereinafter also referred to as "HPG-C2 DNA"), about 0.9 kb (hereinafter also referred to as "HPG-C3 DNA") and about 6.9 kb (hereinafter also referred to as "HPG-C4 DNA") were obtained. A nucleotide sequence of a portion of HPG-C2 DNA fragment and HPG-C4 DNA fragment was determined to reveal the presence of an initiation codon and a termination codon in these DNA fragments, respectively.

It was found that the nucleotide sequence of SEQ ID NO: 5, consisting of a total of 7486 nucleotides, included an open reading frame starting from nucleotide No. 848 which can code for 2039 amino acid residues (SEQ ID NO: 7). A polypeptide comprising the 2039 amino acid residues is hereinafter also referred to as "serotype C HMTp210". Homology search with the existing data base (GeneBank and EMBL) revealed no homology with any known nucleotide and amino acid sequences, indicating that the serotype C HMTp120 polypeptide is a novel substance.

Homology search between the nucleotide sequences coding for the serotype C HMTp120 polypeptide and the serotype A HMTp120 polypeptide revealed about 80% homology. It was further revealed that the region of about 3.4 kb at the 5' site and the region of about 1.2 kb at the 3' site exhibited extremely high homology whereas the region of about 1.5 kb between these 5' and 3' regions showed low homology. The same was also applicable to the corresponding polypeptides encoded by these genes.

Based on the nucleotide sequence coding for the serotype A HMTp120 polypeptide, there can also be obtained, by PCR, DNA fragments from different serotype of *Haemophilus paragallinarum* such as serotype B or serotype C as well as polypeptides coded by said DNA fragments.

More specifically, based on the nucleotide sequence coding for the serotype A HMTp120 polypeptide, there were prepared a synthetic DNA having the nucleotide sequence of SEQ ID NO: 3 as an upstream PCR primer and a synthetic DNA having the nucleotide sequence of SEQ ID NO: 4 as a downstream PCR primer. These primers were designed such that BamHI recognition sequences were added at the 5' sites, respectively, and a full length of translation region of the serotype A HMTp210 polypeptide can be amplified. Using these primers, PCR was carried out using as a template the genomic DNAs from a total of nine strains, i.e. *Haemophilus paragallinarum* serotype A strains 221, 083, W, Germany and Georgia, HPG serotype B strains Spross and 0222, and HPG serotype C strains Modesto and 53-47. Analysis of the obtained PCR products on 0.8% agarose gel electrophoresis confirmed the amplified fragment of about 6.1 kb in any of these strains.

The thus obtained DNA fragment or a portion thereof may be incorporated into a suitable expression vector, the resulting expression vector is used for transformation of a microorganism or an animal cell, and the transformant is cultured to produce the polypeptide of the present invention from *Haemophilus paragallinarum* or a peptide which shares at least a portion of the amino acid sequence of said polypeptide. The peptide which shares a portion of the amino acid sequence can also be produced with a peptide synthesizer.

A suitable signal sequence for secretion in a microorganism or an animal cell can also be linked upstream the DNA coding for the polypeptide of the present invention so that said polypeptide can be secreted into a culture medium. The thus modified DNA for secretion is advantageous in that said polypeptide secreted into a culture medium can easily be purified. A signal sequence includes pelB signal (S. P. Lei et al., J. Bacteriology, 169: 4379–4383, 1987) for *E. coli,* signal from α factor (A. J. Brake, Yeast Genetic Engineering, p269, Butterworth, 1989) for yeast, signal SG-1 from immunoglobulin (H. Maeda et al., Hum. Antibod. Hybridomas, 2: 124–134, 1991), C25 signal (PCT International Publication No. WO94/20632) for an animal cell.

An expression vector includes a plasmid, a viral vector and the like. Any promoter may be included in the expression vector such as lac, tac, pho5, adh, SV40 early, SV40 late, β actin and the like, in consideration of a microorganism or an animal cell used as a host, insofar as the polypeptide having the activity to prevent avian infectious coryza is ultimately obtained. The polypeptide of the present invention can also be expressed as a fusion protein with another protein or peptide such as β-galactosidase, glutathione-S-transferase, maltose binding protein, Protein A, histidine hexamer, and the like. A marker gene includes, in case of an expression vector for a microorganism cell, ampicillin resistant gene, tetracycline resistant gene for *E. coli* as a host, β-isopropyl malate dehydrogenase (Leu2) gene for yeast as a host, and in case of an expression vector for an animal cell, aminoglycoside 3' phosphotransferase (neo) gene, dihydrofolate reductase (dhfr) gene, glutamine synthetase (GS) gene, and the like. An additive for selection includes G418, neomycin, methotrexate, and the like.

Transformation of a host cell may be carried out by the known methods including, for example, a calcium chloride method, a calcium phosphate coprecipitation method, a DEAE dextran method, a lipofectin method, a protoplast polyethylene fusion method, an electroporation, and the like, which can suitably be selected depending on a host used.

The novel polypeptide of the present invention from *Haemophilus paragallinarum* or a peptide which shares at least a portion of the amino acid sequence of said polypeptide may be prepared as described hereinbelow. For example, the HPG3.5 k DNA fragment from HGP serotype A is incorporated into an expression vector pTrcHisC (manufactured by Invitrogen), said expression vector is introduced into *E. coli* strain JM109 for transformation. Among the resulting transformed cells, those transformants which produce the target novel polypeptide are screened by a dot blotting with an index of reactivity with the antibody against said polypeptide. Chicken immunized with a supernatant obtained after centrifugation of a suspension of the ruptured cells have an elevated protection against challenge with HPG serotype A strain 221.

The novel polypeptide may be purified from an extract of cells or a culture supernatant from a large scale culture of the transformant producing said polypeptide by utilizing the above-mentioned methods used in the field of protein chemistry.

The thus obtained novel polypeptide from *Haemophilus paragallinarum* has the activity to prevent avian infectious coryza. Said polypeptide from *Haemophilus paragallinarum*, monoclonal and polyclonal antibodies against said polypeptide and the expression vector as mentioned above may be used as a vaccine or a therapeutic agent for avian infectious coryza either alone or in combination with a suitable carrier, diluent or stabilizing agent in a conventional manner such as injections or oral drugs.

The above novel polypeptide from *Haemophilus paragallinarum* or a polypeptide which shares at least a portion of the amino acid sequence of said polypeptide may be used as an immunogen for preparing a polyclonal and monoclonal antibodies in accordance with the procedures described hereinabove. Said polypeptide as well as the antibody having the capacity to bind thereto may also be utilized in an antigen or antibody detection system such as Western blot, ELISA, and the like, and may also be a material for constructing a diagnostic agent. In addition, affinity chromatography with a suitable carrier to which the above antibody is bound may be used for purification of the above polypeptide.

In accordance with the present invention, there are provided the novel polypeptide from *Haemophilus paragallinarum* and the gene fragment coding for said polypeptide for prevention of avian infectious coryza and the antibody having the HI activity which can be used as a therapeutic agent.

The polypeptide from *Haemophilus paragallinarum,* which the present inventor has found, has a molecular weight of about 130 Kd, has the activity to induce production of the HI antibody, and is the novel, important polypeptide for prevention of avian infectious coryza. Technical problems associated with the obtention of said polypeptide, such as isolation of the gene coding for said polypeptide, construction of the expression vector, preparation of the expression cell, and purification of said polypeptide, are solved by the present invention, which allows for provision of a more effective vaccine than the prior art vaccines. Furthermore, these are useful as a material for providing a rapid, simple diagnostic agent for avian infectious coryza.

The present invention is illustrated in more detail by means of the following Examples but should not be construed to be limited thereto.

EXAMPLE 1

Preparation and Features of Monoclonal Antibody

(1) Preparation of Monoclonal Antibody

*Haemophilus paragallinarum* serotype A strain 221 cells were inoculated to 100 ml of chicken meat infusion medium supplemented with chicken serum and shake-cultured at 37° C. overnight, followed by centrifugation (8,000 rpm, 20 minutes) to recover cells. The obtained cells were washed with PBS while centrifugation and then suspended in PBS containing 0.01% thimerosal at about $5\times10^{10}$ cells/ml. The suspension was sonicated with Branson Sonifier 350 at 20 kHz, 4° C. for 10 minutes (alternative repeat of sonication for 0.5 second and cooling for 0.5 second). The thus obtained suspension of the ruptured cells by sonication was mixed with the same amount of Freund's complete adjuvant and the mixture was well blended till a water-in-oil (w/o) was achieved. Each 0.1 ml of this emulsion was subcutaneously administered to BALB/c mouse at two sites of the back. Four weeks later, each 0.1 ml of an emulsion prepared similarly with Freund's incomplete adjuvant was subcutaneously administered at two sites of the back. After additional 18 days, 0.1 ml of the suspension of the ruptured cells by sonication was intravenously administered.

Three days after the final administration, splenocytes were removed. Said splenocytes ($1\times10^8$ cells) were mixed with mouse myeloma cells P3X63-Ag8.U1 ($1\times10^7$ cells) by padding, thereto was added RPMI1640 medium containing 45% polyethylene glycol previously warmed at 37° C. to conduct cell fusion. The cells after fusion reaction were suspended in HAT medium (RPMI1640 medium containing 5% fetal calf serum supplemented with $1\times10^{-4}$ M hypoxanthine, $4\times10^{-7}$ M aminopterin and $1.6\times10^{-5}$ M thymidine), and after plated on 96-well microtiter plate for cell culture (manufactured by Coning), cultured under the conditions of 37° C. and 5% $CO_2$.

For the wells where hybridomas propagated, the presence of the monoclonal antibody recognizing *Haemophilus paragallinarum* in the culture supernatant was determined with ELISA as described hereinbelow. A suspension of ruptured cells by sonication of *Haemophilus paragallinarum* serotype A strain 221 prepared as mentioned above was diluted 300 folds with PBS and each 100 μl of the suspension was plated on well of microtiter plate for ELISA (Immulon II manufactured by Dynatech). The microtiter plate was left to stand at 4° C. overnight and masked with PBS containing 5% skim milk at 200 μl per well at room temperature for 2 hours. The microtiter plate was washed with PBS containing 0.05% TWEEN 20 (PBS-T) and thereto was added 100 μl of the culture supernatant of hybridomas diluted 10 folds with PBS-T containing 5% skim milk for reaction at room temperature for 2 hours. After washing with PBS-T, each 100 μl of peroxidase-labeled anti-mouse IgG (manufactured by Bio-Rad) diluted 10,000 folds with PBS-T containing 5% skim milk was added for reaction at room temperature for 2 hours. Then, after washing with PBS-T, each 100 μl of 0.05 M citrate-0.1 M disodium hydrogenphosphate buffer (pH 5.0) containing 6 mg per 11 ml of ortho-phenylene-diamine dihydrochloride (OPD; manufactured by Katayama Kagaku K.K.) and 4.75 μl of hydrogen peroxide (containing $H_2O_2$ at 31%; manufactured by Mitsubishi Gasu Kagaku K.K.) was added for reaction at room temperature for 30 minutes. Each 50 μl of 3 M sulfuric acid was added to quench the reaction and absorbance (490 nm) of each well was measured with Autoreader for ELISA.

Hybridomas of the wells where the antibody against *Haemophilus paragallinarum* serotype A was secreted in the culture supernatant were cloned by a limiting dilution method so that they become monoclonal. Thus, nine clones producing the monoclonal antibody against *Haemophilus paragallinarum* serotype A were obtained.

(2) HI Activity of Monoclonal Antibodies

These hybridomas were cultured in a large amount and intraperitoneally administered to BALB/c mice, pretreated with an immunosuppressive agent, pristane (2,6,10,14-tetramethyl-pentadecane; manufactured by Aldrich), where the hybridomas propagated. Ten to twenty days later, the mice were sacrificed and the produced ascites were removed therefrom and HI activity of the ascites was determined.

A suspension of *Haemophilus paragallinarum* serotype A strain 221 cells inactivated with thimerosal was used as an HA antigen for HI test and prepared based on HA titer. First, using a V-shaped microtiter plate (Sanko Junyaku K.K.), a suspension of a glutaraldehyde-fixed 1% chicken erythrocytes (0.05 ml) was added to a 2 folds serial dilution of HA antigen (0.05 ml), and after standing at room temperature for 60 minutes, the bottom of the plate was observed. A maximum dilution which agglutinates erythrocytes was defined as HA titer and, regarding a concentration of HA antigen at this dilution as 1 unit, a stock solution of HA antigen was prepared so that it contains 4 units.

Then, to 0.2 ml of mouse ascites was added 5 folds amount of 25% kaolin solution and the mixture was shaken at 37° C. for 30 minutes for sensitization, followed by centrifugation to give a supernatant. This supernatant of centrifugation after kaolin treatment was added to precipitates obtained by centrifugation of glutaraldehyde-fixed 10% chicken erythrocytes (2 ml) and the mixture was shaken for sensitization at 37° C. for 60 minutes. After sensitization, a supernatant was obtained by centrifugation and used as 5 folds diluted mouse ascites for determination of HI antibody. Using a V-shaped microtiter plate, to 0.025 ml of a 2 folds serial dilution of this supernatant was added the same amount of the suspension of strain 221 cells inactivated with thimerosal containing 4 hemagglutination units and, after mixing, the mixture was left to stand for 15 minutes. After sufficient sensitization, 0.05 ml of a suspension of glutaraldehyde-fixed 1% chicken erythrocytes was added. After the mixture was left to stand at room temperature for 60 minutes, the bottom of the microtiter plate was observed. A maximum dilution which inhibits hemagglutination was defined as an HI antibody titer. Among nine clones, the monoclonal antibodies from three clones (HpgA 59-40, HpgA 59-145 and HpgA 59-180) exhibited a high HI activity (Table 1). The clone HpgA 59-180 has been deposited by the applicant as FERM BP-6084 at National Institute of Bioscience and Human-Technology Agency of Industrial Science and Technology (1–3, Higashi 1-chome, Tsukuba-shi, Ibaraki-ken) on Sep. 5, 1996.

TABLE 1

| Monoclonal antibody | HI antibody titer |
| --- | --- |
| HpgA 59-33 | <50 |
| HpgA 59-40 | 25,600 |
| HpgA 59-48A | <50 |
| HpgA 59-48B | <50 |
| HpgA 59-145 | 1,600 |
| HpgA 59-180 | 12,800 |
| HpgA 59-188 | <50 |
| HpgA 59-236 | <50 |
| HpgA 59-284 | <50 |

(3) Protective Activity of Monoclonal Antibodies

A mouse ascites (0.3 ml) containing these antibodies was intraperitoneally administered to SPF white leghorn chickens of 4 to 6 weeks old, each group comprising 8 to 10 chickens, and on the next day, about $10^8$ cells of *Haemophilus paragallinarum* serotype A strain 221 were applied dropwise to the nasal cavity of the chickens for challenge. A control group which was given no mouse ascites was also used and was challenged in the same manner. Each group was observed for the presence of the coryza symptoms (i.e. a running nose, swelling of the face and epiphora) for 10 days. All the groups which previously received the monoclonal antibodies having the HI activity (hereinafter also referred to as "HI-MCA") were likely to retard the onset as compared to the control group. On the contrary, all the groups administered with the monoclonal antibodies of the other clones showed no significant difference (FIGS. 1 to 4).

EXAMPLE 2

Purification and Property of Antigen Recognized by HI-MCA (1) Purification of HI-MCA HI-MCA (HpgA 59-180) was purified from mouse ascites using Protein A-Sepharose CL-4B (manufactured by Pharmacia) and MAPS-II Mouse Monoclonal Antibody Purification Kit (manufactured by Bio-Rad) in accordance with protocol attached thereto. First of all, to 4 ml of mouse ascites was added the same amount of a binding buffer included in the Antibody Purification Kit. After the mixture was filtered with Sterivex filter of 0.45 micron (manufactured by Millipore), it was applied to Protein A-Sepharose CL-4B column (gel bed volume 5 ml) and was thoroughly washed with the binding buffer till less than 0.05 of the absorbance at 280 nm was obtained. Then, the antibodies bound to the column were eluted with an elution buffer included in the kit. The eluted antibodies were dialyzed against 0.2 M sodium hydrogen carbonate (pH 8.3) containing 0.5 M sodium chloride to give 40 mg of purified HI-MCA (HpgA 59-180). Similarly, HI-MCA (HpgA 59-40) was also purified to give 12 mg.

(2) Binding of HI-MCA to Carrier

Then, the purified HI-MCA (HpgA 59-180) as a ligand was bound to HiTrap NHS-activated column (manufactured by Pharmacia) in accordance with protocol attached thereto. First of all, HiTrap NHS-activated column (gel bed volume 1 ml) was washed with 1 mM hydrochloric acid and then circulated with 0.2 M sodium hydrogen carbonate solution (10 ml) containing 0.5 M sodium chloride and 10 mg of the above purified HI-MCA (HpgA 59-180) at room temperature for 30 minutes so that HI-MCA was bound to the column. The obtained HI-MCA-bound HiTrap column was washed each three times alternatively with 0.5 M ethanolamine (pH 8.3) containing 0.5 M sodium chloride, and 0.1 M sodium acetate buffer (pH 4.0) containing 0.5 M sodium chloride and equilibrated with PBS for purification of an antigen recognized by HI-MCA.

(3) Purification of Antigen Recognized by HI-MCA

An antigen was purified from a culture of *Haemophilus paragallinarum* serotype A strain 221 by an affinity chromatography using HI-MCA as a ligand. An antigen was detected by ELISA method as described hereinbelow.

The above purified HI-MCA (HpgA 59-40) was diluted with 0.05 M sodium carbonate buffer (pH 9.0) to a concentration of 1.6 $\mu$g/ml and was placed in a well of microtiter plate for ELISA. The plate was left to stand at 4° C. overnight and masked with PBS containing 5% skim milk at room temperature for 2 hours. After washing with PBS-T, an eluate from the column diluted 10 folds with PBS-T containing 5% skim milk was reacted at room temperature for 2 hours. After washing with PBS-T, peroxidase-labeled HI-MCA (HpgA 59-180) diluted 10,000 folds with PBS-T containing 5% skim milk was reacted at room temperature for 2 hours. Then, after washing with PBS-T, a substrate solution containing OPD and hydrogen peroxide was added for reaction at room temperature for 30 minutes. Peroxidase-labeled HI-MCA (HpgA 59-180) was prepared by binding horseradish peroxidase (manufactured by Toyobo K.K.) to the above purified HI-MCA (HpgA 59-180) as described by Yoshitake et al. (J. Biochem., 92: 1413–1424, 1982).

*Haemophilus paragallinarum* serotype A strain 221 cells were inoculated to 100 ml of chicken meat infusion culture supplemented with chicken serum and shake-cultured at 37° C. for 2 days. To a culture supernatant obtained after removal of cells by centrifugation at 8,000 rpm for 20 minutes was immediately added a serine protease inhibitor, phenylmethylsulfonyl fluoride, at 1 mM, and the mixture was filtered with 0.45 micron Sterivex filter. The HI-MCA-bound HiTrap column preequilibrated with PBS was added with 60 ml of the above filtrate and washed with PBS. When the absorbance at 280 nm became less than 0.05, an antigen bound to HI-MCA was eluted with 3M sodium thiocyanate. Antigens recognized by HI-MCA were not found in unbound fractions but in most part were recovered in fractions eluted with 3 M sodium thiocyanate. This eluate was dialyzed against 50 mM Tris-HCl buffer (pH 8.0) containing 50 mM sodium chloride.

(4) Amino Acid Sequence Analysis of N-terminal of Antigen Recognized by HI-MCA

Figure 5:
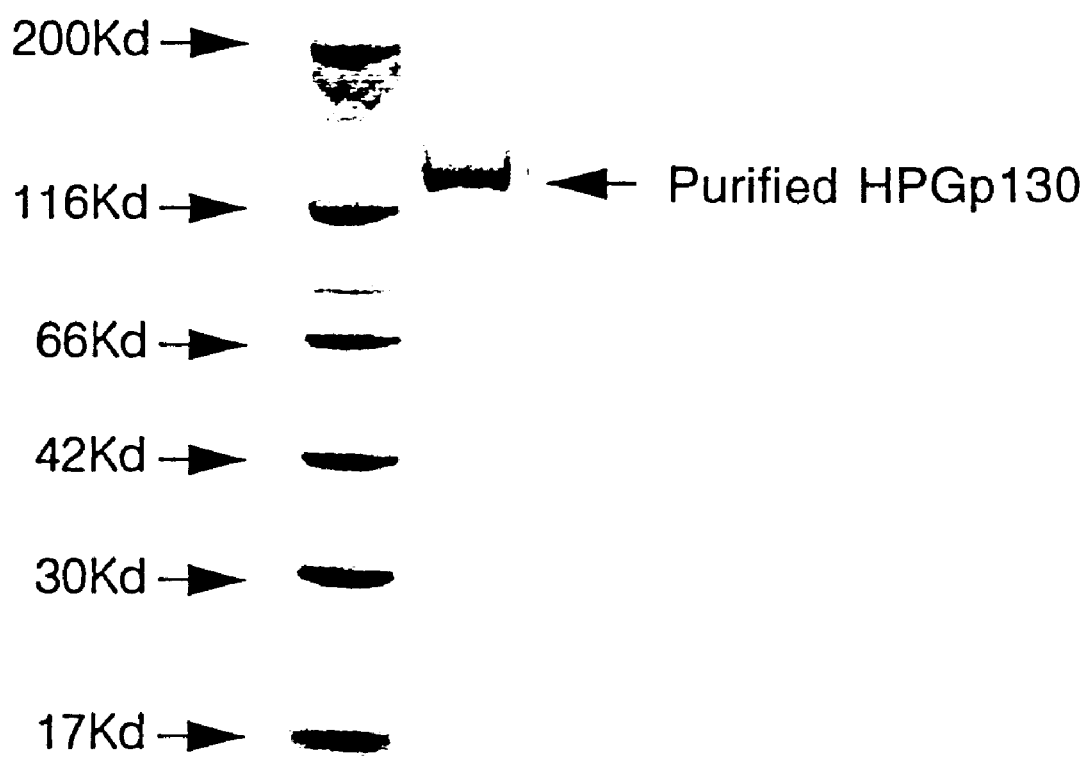
FIG. 5 is a photograph showing the result of SDS-PAGE electrophoresis with CBB staining of HPGp130 polypeptide which is purified by affinity chromatography using the monoclonal antibody having the HI activity (clone HpgA 59-180) as a ligand.

After treatment with 2-mercaptoethanol, the eluate from the affinity column was subjected to sodium dodecyl sulfate polyacrylamide gel electrophoresis (SDS-PAGE) with 5 to 20% polyacrylamide gel in accordance with Laemmli, Nature, 227: 680–685, 1970, which was stained with 0.25% Coomassie Brilliant Blue R250 (CBB) dissolved in 50% methanol-10% acetic acid to reveal a band of a molecular weight about 130 Kd (FIG. 5). This polypeptide was referred to as HPGp130 and an amino acid sequence of the N-terminal was determined as described hereinbelow.

First, the purified HPGp130 polypeptide was treated with 2-mercaptoethanol and then subjected to SDS-PAGE using 5% polyacrylamide gel. After electrophoresis, the gel was washed with a transfer buffer (10 mM N-cyclohexyl-3-amino-propanesulfonic acid, 10% methanol, pH 11) and overlaid to polyvinylidene difluoride (PVDF) membrane (manufactured by Millipore), which was previously immersed successively in 100% methanol and a transfer buffer, followed by transfer with TRANS-BLOT CELL (manufactured by Bio Rad) at 20 V overnight. The PVDF membrane after transfer was washed with water and stained with 0.1% Amido Black dissolved in 45% methanol-10% acetic acid for 30 seconds, followed by decolorization with distilled water.

The stained band of a molecular weight 130 Kd was cut out and analyzed with Protein Sequencer (Applied Biosystems 477A). Thirteen amino acid residues at the N-terminal were analyzed, and as a result, the amino acid sequence was found to be Lys-Trp-Leu-Glu-Val-Tyr-Ser-Ser-Ser-Val-Lys-Leu-Ser as shown in SEQ ID NO: 2.

(5) Induction of HI Antibody Production by HPGp130

Whether HPGp130 polypeptide could induce production of HI antibody was investigated. An emulsion (1 ml; about 20 μg of HPGp130 polypeptide per animal) prepared by mixing the HPGp130 polypeptide solution (about 40 μg/ml) with the same amount of Freund's complete adjuvant was subcutaneously injected to guinea pig at two sites of the back for immunization. About three weeks later, 1 ml of an emulsion prepared similarly with Freund's incomplete adjuvant was injected subcutaneously at two sites of the back. Additional two weeks later, the emulsion prepared with Freund's incomplete adjuvant was boosted subcutaneously at two sites of the back and four weeks thereafter the test animals were bled. HI antibody titer of the obtained antisera was determined as described above to reveal a high HI antibody titer (5,120 folds). Thus, it was found that the HPGp130 polypeptide induced production of HI antibody deeply involved in protection against avian infectious. coryza.

(6) Peptide Recognized by Anti-HPGp130 Polypeptide Guinea Pig Sera

A polypeptide recognized by anti-HPGp130 polypeptide guinea pig serum was analyzed by Western blot. First, the purified HPGp130 polypeptide and HPG seritype A strain 221 cells cultured in chicken meat infusion medium supplemented with chicken serum were treated with 2-mercaptoethanol and subjected to SDS-PAGE. After completion of electrophoresis, the gel was immersed in a transfer buffer (25 mM Tris, 192 mM glycine, 20% ethanol, pH 8.3) for 5 minutes and overlaid to PVDF membrane, which was previously immersed in 100% methanol and the transfer buffer in this order, and a transfer was carried out using TRANS-BLOT SD CELL (manufactured by Bio Rad) at 7 V for 1 hour. The membrane was masked with PBS containing 5% skim milk at 4° C. overnight, washed with PBS-T and then reacted with anti-HPGp130 polypeptide guinea pig serum diluted 1,000 folds with PBS-T containing 5% skim milk at room temperature for 2 hours. After washing with PBS-T, peroxidase-labeled anti-guinea pig IgG (manufactured by Zymed) diluted 2,000 folds with PBS-T containing 5% skim milk was reacted at room temperature for 2 hours. After washing with PBS-T, the membrane was immersed in 10 ml of 0.1 M Tris-HCl buffer (pH 7.5) containing 5 mg of 3,3'-diaminobenzidine tetrahydrochloride (DAB; manufactured by Dojin Kagaku K.K.) and 3 μl of hydrogen peroxide for reaction. As a result, anti-HPGp130 polypeptide guinea pig serum recognized the HPGp130 polypeptide and a band of a molecular weight about 160 Kd, possibly a precursor of the polypeptide (FIG. 6).

(7) Immunogenicity of HPGp130 Polypeptide

In accordance with the procedures as described hereinabove, ten SPF white leghorn chickens of 5 weeks old were immunized by subcutaneously administering at the leg 0.5 ml of an emulsion (containing about 10 μg of HPGp130 polypeptide) prepared by mixing an HPGp130 polypeptide solution (about 40 μg/ml) and the same amount of Freund's complete adjuvant. Three weeks later, the chickens were subcutaneously administered at the leg with 0.5 ml of an emulsion prepared similarly with Freund's incomplete adjuvant. Two weeks later, the chickens were boosted subcutaneously at the leg with an emulsion prepared similarly with Freund's incomplete adjuvant. Seven weeks after the first immunization, the chickens were challenged with *Haemophilus paragallinarum* serotype A strain 221. As a control, one group was immunized twice with 0.5 ml of 0.25% formalin-inactivated HPG serotype A strain 221 (cell number prior to inactivation: $4 \times 10^8$ cells/ml) supplemented with aluminum hydroxide gel (in terms of aluminum: 0.5 mg/ml) at the interval of three weeks and another group was not immunized and both control groups were challenged similarly. The results are shown in Table 2. Both groups immunized either with HPGp130 polypeptide or formalin-inactivated cells showed protection against the onset of the disease in all the chickens. For the non-immunization group, however, the symptoms were shown in all the chickens.

TABLE 2

| Immunization group | Tested chicken | Protected chicken | Protection rate (%) |
| --- | --- | --- | --- |
| Purified HPGp130 | 10 | 10 | 100 |
| Formalin-inactivated strain 221 | 10 | 10 | 100 |
| Non immunization control | 8 | 0 | 0 |

EXAMPLE 3

Cloning of Gene Coding for Polypeptide (Serotype A HMTp210) from *Haemophilus paragallinarum* Serotype A Strain 221

(1) Screening from Genomic Library

*Haemophilus paragallinarum* serotype A strain 221 cells were inoculated to 5 ml of chicken meat infusion medium supplemented with chicken serum and shake-cultured at 37° C. overnight and the cells were recovered by centrifugation. After washing the obtained cells with PBS by centrifugation, DNA was extracted and purified from the cells with Sepagene kit (manufactured by Sanko Junyaku K.K.) in accordance with protocol attached thereto. The DNA was dissolved in 50 $\mu$l of TE buffer (10 mM Tris-HCl buffer containing 1 mM EDTA, pH 8.0) and the obtained solution was used as a genomic DNA solution. Then, using cDNA Rapid Cloning Module-λgt11 (manufactured by Amersham), 0.2 μg of the genomic DNA digested with restriction enzyme EcoRI was ligated to 0.5 μg of λgt11 arm digested with restriction enzyme EcoRI in accordance with protocol attached thereto. Using λ-DNA In Vitro Packaging Module (manufactured by Amersham), the ligated product was inserted into λ phage in accordance with protocol attached thereto. The obtained solutions of recombinant phage were used as a genomic library.

The above solutions of genomic library were added to a suspension of *E.coli* strain Y1090 (manufactured by Amersham) about $10^8$ cells in an aqueous solution of 10 mM magnesium sulfate for absorption at 37° C. for 15 minutes. Thereto was added LB soft agar medium (containing tryptone 10 g, yeast extract 5 g, sodium chloride 10 g, ampicillin 50 mg, maltose 4 g and agar 8 g in 1000 ml, pH 7) for overlay warmed at 45° C. The mixture was overlaid to LB agar medium (containing tryptone 10 g, yeast extract 5 g, sodium chloride 10 g, ampicillin 50 mg and agar 15 g in 1000 ml, pH 7) and incubated at 42° C. for 3 hours. A nitrocellulose membrane immersed in an aqueous solution of 10 mM isopropyl-β-D-thiogalacto-pyranoside (IPTG) was air-dried, overlaid to the above plate and incubated at 37° C. overnight. The nitrocellulose membrane was then peeled off from the plate, washed with PBS-T and masked with PBS containing 5% skim milk at room temperature for 2 hours. Thereafter, the procedures as described in Example 2 (6) were repeated so that anti-HPGp130 polypeptide guinea pig serum, peroxidase-labeled anti-guinea pig IgG and a substrate were successively reacted. A series of these procedures gave plaques which express an antigen specifically reactive with anti-HPGp130 guinea pig serum from *Haemophilus paragallinarum* serotype A strain 221. About 5,000 plaques were immunologically screened as described above to give 43 positive plaques. These positive plaques were recovered in an SM buffer (50 mM Tris-HCl buffer containing 0.1 M sodium chloride, 10 mM magnesium sulfate and 0.01% gelatin, pH 7.5) and, after adding several drops of chloroform, stored at 4° C. Ten among the recovered positive plaques were further subjected to second and third screening as in the primary screening.

The recombinant λgt11 phages found positive in the immunological screening were added to a suspension of *E. coli* strain Y1090 about $10^8$ cells in an aqueous solution of 10 mM magnesium sulfate for absorption at 37° C. for 15 minutes. Thereto was added 10 ml of LB liquid medium containing 0.4% maltose, 5 mM calcium chloride and ampicillin 50 μg/ml and the cells were further cultured at 37° C. overnight. After bacteriolysis with addition of several drops of chloroform, the lysis solution was centrifuged to remove the intact *E. coli* cells and debris. To 5 ml of the obtained culture supernatant was added the same amount of an aqueous solution of 2.5 M sodium chloride containing 20% polyethylene glycol 6,000 and the mixture was left to stand on ice for 1 hour. After centrifugation at 10,000 rpm, precipitated λgt11 phage was subjected to. phenol treatment and isopropanol precipitation to recover phage DNA. About 150 μg of the obtained phage DNA was digested with EcoRI and then electrophoresed on 0.8% agarose gel to separate DNA fragments derived from *Haemophilus paragallinarum* serotype A strain 221. Using SEPHAGLAS™ BandPrep Kit (manufactured by Pharmacia), the DNA fragments were eluted and recovered from the gel in accordance with protocol attached thereto. All the DNA fragments obtained from ten positive phages had a length of about 1.2 kb. A DNA fragment (hereinafter referred to as "HPG1.2 k DNA") obtained from the phage of a clone (clone 2) was used in the following test.

(2) Nucleotide Sequence of HPG1.2 k DNA Fragment

Plasmid pUC119 (manufactured by Takara Shuzo K.K.) was digested with EcoRI and then treated with alkaline phosphatase to dephosphorize the 5' end. The cleaved pUC119 DNA was treated with phenol and chloroform and then harvested by precipitation with ethanol. The cleaved pUC119 and the HPG1.2 k DNA fragment were ligated together with DNA Ligation Kit ver. 2 (manufactured by Takara Shuzo K.K.). Competent cells of *E.coli* strain JM109 (manufactured by Takara Shuzo K.K.) were transformed with the ligated product and then cultured on Circle Grow agar medium (manufactured by BIO101) containing 50 μg/ml of ampicillin at 37° C. overnight. Colonies grown on the agar medium were inoculated to 0.5 ml of Circle Grow medium containing 50 μg/ml of ampicillin and cultured at 37° C. for 5 hours. Plasmids were extracted from the cells by an alkali method and, after digestion with EcoRI, subjected to 0.8% agarose gel electrophoresis to detect recombinant plasmids containing DNA fragment with the same length as the 1.2 k DNA derived from *Haemophilus paragallinarum* serotype A strain 221, and thereby transformed *E.coli* were confirmed.

The obtained transformants of *E.coli* were cultured on Circle Grow medium containing 50 μg/ml of ampicillin and then the recombinant plasmids (hereinafter referred to as "pUA1.2") were recovered from the cells by PEG precipitation method. Using a Primer Walking method, a nucleotide sequence of the HPG1.2 k DNA fragment was analyzed using a DNA sequencer (Applied Biosytems 377). As a result, a sequence of 1170 nucleotides was determined. It was found that the nucleotide sequence of the HPG1.2 k DNA corresponds to the sequence of from No. 1988 to No. 3157 in SEQ ID NO: 1, which is a nucleotide sequence coding for serotype A HMTp120 polypeptide as described hereinbelow, and codes for 389 amino acid residues with no initiation codon and termination codon within this region. A corresponding amino acid sequence was also shown which depicts no sequence equivalent to the N-terminal amino acid sequence of HPGp130 polypeptide. Accordingly, it was considered that HPG1.2 k DNA codes for a portion of HPGp130 polypeptide.

(3) Cloning of HPG3.5 k DNA

Using DIG-DNA Labeling Kit (manufactured by Boehringer Mannheim), about 0.3 μg of the above HPG1.2 k DNA was labeled with digoxigenin (DIG) in accordance with protocol attached thereto. After the genomic DNA of *Haemophilus paragallinarum* serotype A strain 221 was cleaved with several restriction enzymes, a suitable amount of the cleaved products was electrophoresed on 0.8% agarose gel and then transferred to HYBOND N+ membrane (manufactured by Amersham). Using the DIG-labeled HPG1.2 k DNA as a probe, a Southern hybridization was carried out with DIG Nucleic Acid Detection Kit (manufactured by Boehringer Mannheim) in accordance with protocol attached thereto for detection of desired DNAs. As a result, about 3.5 kb fragment obtained by HindIII digestion hybridized to the DIG-labeled HPG1.2 k DNA. Thus, this fragment was separated on 0.8% agarose gel electrophoresis and eluted and recovered from the gel with SEPHAGLAS™ BandPrep Kit in accordance with protocol attached thereto.

On the other hand, plasmid pUC119 was digested with HindIII and then treated with alkaline phosphatase to dephosphorize the 5' end. The cleaved pUC119 DNA was treated with phenol and chloroform and then recovered by precipitation with ethanol. The cleaved pUC119 and the above HindIII digest (about 3.5 kb) from the genome of *Haemophilus paragallinarum* serotype A strain 221 were ligated together with DNA Ligation Kit ver. 2. Competent cells of *E.coli* strain JM109 were transformed with the ligated product and then cultured on Circle Grow agar medium containing 50 µg/ml of ampicillin at 37° C. overnight. To the agar medium where transformed *E.coli* grown was overlaid Hybond N+ membrane to lift the colonies. Using the DIG-labeled HPG1.2 k DNA as a probe, a colony hybridization was carried out in the conventional manner and positive clones were screened with DIG Nucleic Acid Detection Kit.

The positive clones were cultured on Circle Grow medium containing 50 µg/ml of ampicillin. Plasmids were recovered from the cells by PEG precipitation method. The obtained recombinant plasmid (hereinafter referred to as "pUA3.5") was digested with HindIII and then electrophoresed on 0.8% agarose gel to separate 3.5 kb DNA fragment derived from *Haemophilus paragallinarum* serotype A strain 221. Using Seph-ag-l-as BandPrep Kit, this DNA fragment (hereinafter referred to as "HPG3.5 k DNA") was eluted and recovered in accordance with protocol attached thereto. *E.coli* UA3.5JM transformed with the recombinant plasmid has been deposited by the applicant as FERM BP-6083 at National Institute of Bioscience and Human-Technology Agency of Industrial Science and Technology (1-3, Higashi 1-chome, Tsukuba-shi, Ibarakiken) on Sep. 5, 1996.

(4) Expression of HPG3.5 k DNA

The expression vector pTrcHisC (manufactured by Invitrogen) was digested with HindIII and then treated with alkaline phosphatase to dephosphorize the 5' end. The cleaved pTrcHisC DNA was treated with phenol and chloroform and then recovered by precipitation with ethanol. The cleaved pTrcHisC and the above HPG3.5 k DNA were ligated together with DNA Ligation Kit ver. 2. Competent cells of *E.coli* strain JM109 were transformed with the ligated product and then cultured on CIRCLE GROW agar medium containing 50 μg/ml of ampicillin at 37° C. overnight. Colonies grown on the agar medium were inoculated to 0.5 ml of CIRCLE GROW medium containing 50 μg/ml of ampicillin and cultured at 37° C. for 5 hours. Plasmids were extracted from the cells by an alkali method and, after digestion with HindIII, subjected to 0.8% agarose gel electrophoresis to detect recombinant plasmids containing DNA fragment with the same length as the 3.5 k DNA derived from *Haemophilus paragallinarum* serotype A strain 221, and thereby transformed *E.coli* cells were confirmed.

The obtained transformants of *E.coli* were plated on 1 ml of CIRCLE GROW medium containing 50 μg/ml of ampicillin and cultured at 37° C. for 3 hours. Thereto was further added IPTG (final concentration of 1 mM) and the transformants were cultured at 37° C. for additional 3 hours. The cells were harvested from the culture by centrifugation and suspended in 50 μl of PBS. The suspension of the cells (10 μl) was mixed with the same amount of 2% SDS and the mixture was boiled for 5 minutes and 2 μl was then spotted on a nitrocellulose membrane. The nitrocellulose membrane was air-dried and then masked with PBS containing 5% skim milk at 4° C. overnight. Thereafter, the procedures as described in Example 2 (6) were repeated so that anti-HPGp130 polypeptide guinea pig serum, peroxidase-labeled anti-guinea pig IgG and a substrate were successively reacted. A series of these procedures gave *E.coli* which was transformed with a recombinant plasmid wherein HPG3.5 k DNA was ligated in a right direction and expresses an antigen specifically reactive with anti-HPGp130 guinea pig serum.

(5) Immunogenicity of HPG3.5 k-HIS Polypeptide

The obtained transformants of *E.coli* were inoculated to 200 ml of Circle Grow medium containing 50 μg/ml of ampicillin and cultured at 37° C. for 3 hours. Thereto was added IPTG (final concentration of 1 mM) and the transformants were cultured at 37° C. for additional 3 hours. The cells were harvested from the culture by centrifugation and suspended in 10 ml of PBS. To the suspension was added lysozyme at 100 μg/ml for reaction at 4° C. for 1 hour. The suspension was sonicated with Branson SONIFIER 350 at 4° C. for 10 minutes for bacteriolysis. Intact cells were removed by centrifugation and the obtained supernatant was used as a crude HPG3.5 k-HIS polypeptide.

Ten SPF white leghorn chickens 8 weeks old were immunized by subcutaneously administering at the leg 0.5 ml of an emulsion prepared by thoroughly mixing the crude HPG3.5 k-HIS polypeptide solution with the same amount of Freund's complete adjuvant. Three weeks later, the chickens were subcutaneously administered at the leg with 0.5 ml of an emulsion prepared similarly with Freund's incomplete adjuvant. Two weeks later, the chickens were boosted subcutaneously at the leg with an emulsion prepared similarly with Freund's incomplete adjuvant. Seven weeks after the first immunization, the chicken were challenged with *Haemophilus paragallinarum* serotype A strain 221. As a control, as described in Example 2 (7), one group was immunized with formalin-inactivated HPG serotype A strain 221 and another group was not immunized and both control groups were challenged similarly. The results are shown in Table 3. The group immunized with the crude HPG3.5 k-HIS polypeptide showed protection against the onset of the disease in seven among ten chicken. The group immunized with the formalin-inactivated cells exhibited protection against the onset of the disease in all the chickens whereas the non-immunization group showed the symptoms in all the chickens.

TABLE 3

| Immunization group | Tested chicken | Protected chicken | Protection rate (%) |
|---|---|---|---|
| Crude HPGp3.5k-HIS | 10 | 7 | 70 |
| Formalin-inactivated strain 221 | 10 | 10 | 100 |
| Non immunization control | 8 | 0 | 0 |

(6) Nucleotide Sequence of HPG3.5 k DNA Fragment

A nucleotide sequence of HPG3.5 k DNA fragment was analyzed with a DNA sequencer as described above. As a result, a sequence of 3450 nucleotides was determined. The nucleotide sequence of HPG3.5 k DNA fragment corresponds to the nucleotide sequence of from nucleotides No. 1 to No. 3450 in SEQ ID NO: 1. A region was found which codes for an amino acid sequence identical to that of the N-terminal of HPGp130 polypeptide. An open reading frame was obtained from HPG3.5 k DNA in the same frame as that of HPGp130 polypeptide and it was found that translation starts at nucleotide No. 243 to code for 1069 amino acid residues. There was no termination codon within the region and thus it was assumed that HPG3.5 k DNA codes for a portion of HPGp130 polypeptide. A corresponding amino acid sequence is also shown.

(7) Cloning of HPG4.1 k DNA

The above HPG3.5 k DNA fragment was labeled with DIG as described above. After the genomic DNA of *Hae-*

Figure 7:
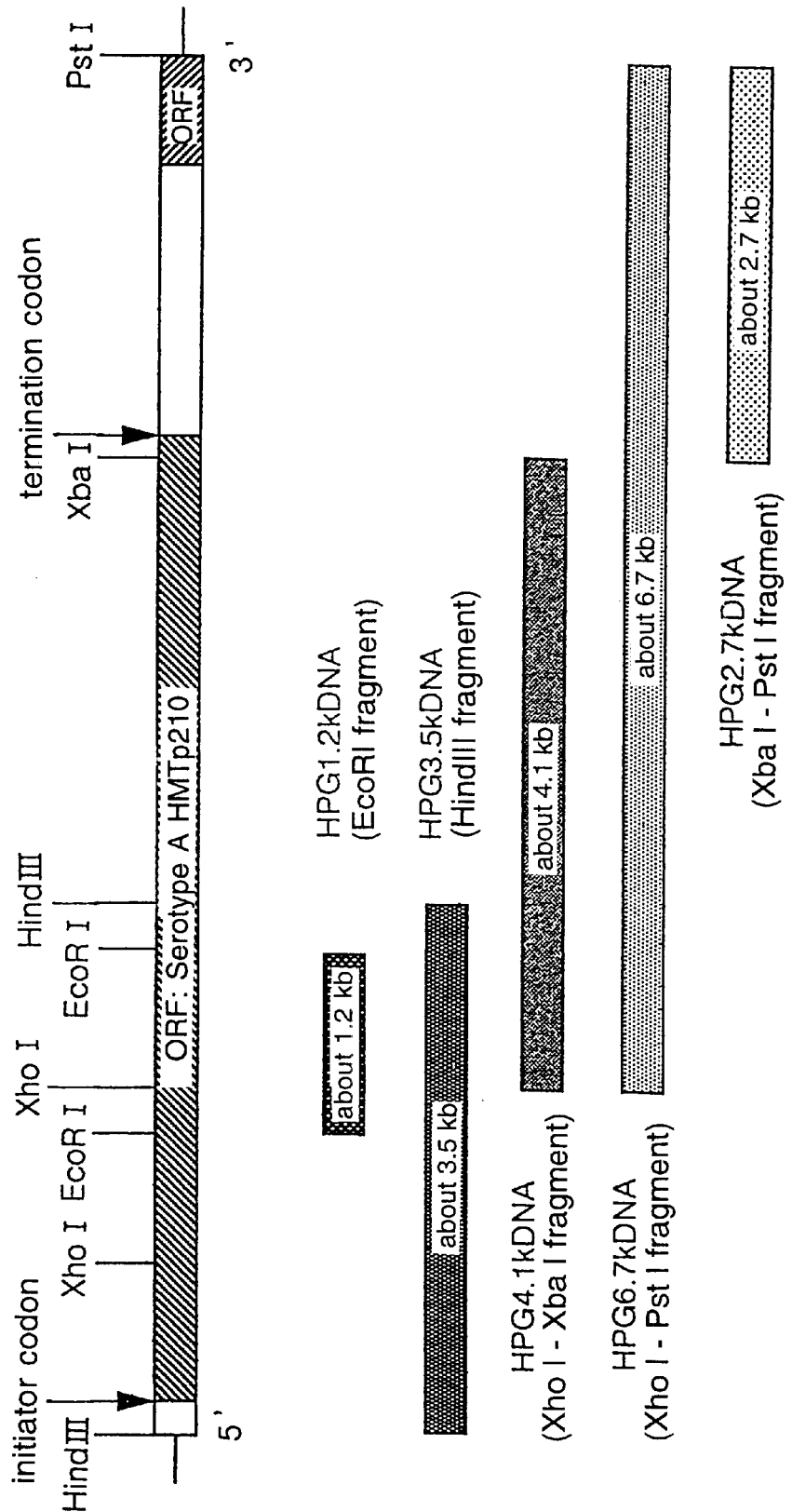
FIG. 7 is a schematic illustration showing the position of HPG1.2 k DNA, HPG3.5 k DNA, HPG4.1 k DNA, HPG6.7 k DNA and HPG2.7 k DNA fragments cloned from the genome of *Haemophilus paragallinarum* serotype A strain 221.

*mophilus paragallinarum* serotype A strain 221 was cleaved with restriction enzymes XhoI and XbaI, a Southern hybridization was carried out as described in Example 3 (3) using the DIG-labeled HPG3.5 k DNA or the DIG-labeled HPG1.2 k DNA as a probe. As a result, DNAs of about 5.5 kb, about 4.1 kb and about 1 kb were detected with the DIG-labeled HPG3.5 k DNA as a probe. When the DIG-labeled HPG1.2 k DNA was used as a probe, DNAs of about 4.1 kb and about 1 kb were detected. Since there are two XhoI sites within the HPG3.5 k DNA fragment as shown in FIG. 7, it was considered that the DNA of about 5.5 kb was a fragment corresponding to the 5' site from the first XhoI cleavage site, the DNA of about 4.1 kb was a fragment corresponding to the 3' site from the second XhoI cleavage site and the DNA of about 1 kb was a fragment between these two XhoI sites. Thus, the fragment of about 4.1 kb was separated and recovered on 0.8% agarose gel electrophoresis.

Figure 8:
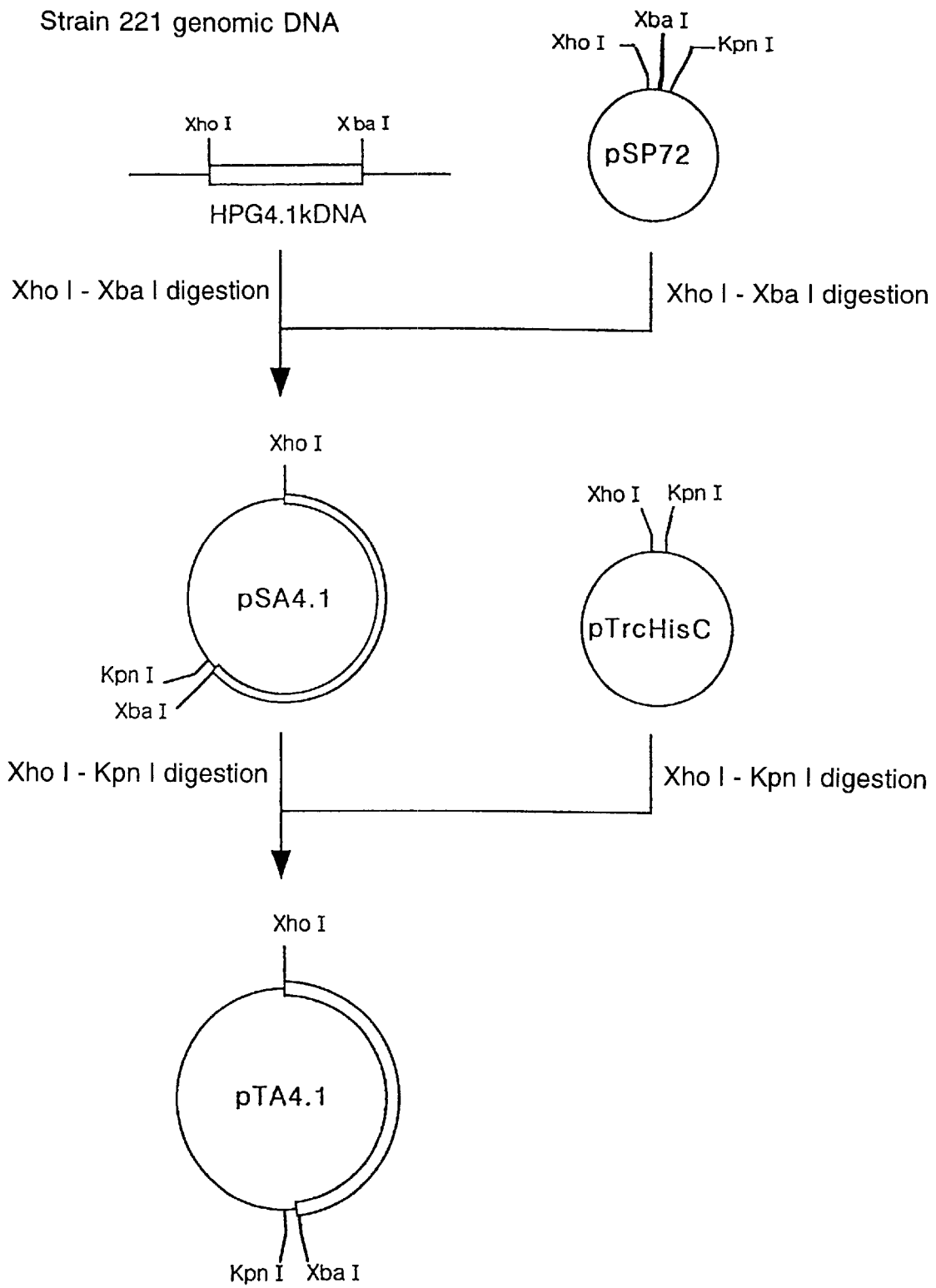
FIG. 8 is a schematic illustration showing construction of plasmid pSA4.1 by inserting the XhoI-XbaI fragment (HPG4.1 k DNA) from the genome of *Haemophilus paragallinarum* serotype A strain 221 into plasmid pSP72, followed by construction of plasmid pTA4.1 by inserting the XhoI-KpnI fragment from the plasmid pSA4.1 into plasmid pTrcHisC.

As shown in FIG. 8, plasmid pSP72 (manufactured by Promega) was digested with XhoI and XbaI and, after dephosphorizing the 5' end, ligated with the above XhoI-XbaI digest (about 4.1 kb) derived from the genome of *Haemophilus paragallinarum* serotype A strain 221. *E.coli* strain JM109 cells were transformed with the ligated product. For the obtained *E.coli* transformants, a colony hybridization was carried out using the DIG-labeled HPG3.5 k DNA as a probe to screen positive clones.

The positive clones were cultured on Circle Grow medium containing 50 µg/ml of ampicillin. Plasmids were recovered from the cells by PEG precipitation method. The obtained plasmid (hereinafter referred to as "pSA4.1"), in which the XhoI-XbaI digest fragment (hereinafter referred to as "HPG4.1 k DNA") derived from *Haemophilus paragallinarum* serotype A strain 221 was incorporated, was digested with XhoI and XpnI and then electrophoresed on 0.8% agarose gel to separate and recover a DNA fragment of about 4.1 kb which was the above HPG4.1 k DNA added with XbaI-KpnI fragment from the plasmid pSP72.

(8) Expression of HPG4.1 k DNA

As described in Example 3 (4), the expression vector pTrcHisC was digested with XhoI and XpnI and, after dephosphorizing the 5' end, ligated with the above XhoI-XpnI digest of about 4.1 kb. *E.coli* strain JM109 cells were transformed with the ligated product. From the obtained transformants of *E.coli*, there was obtained *E.coli* which was transformed with a recombinant plasmid wherein HPG4.1 k DNA was ligated in a right direction and expresses an antigen specifically reactive with anti-HPGp130 guinea pig serum.

(9) Immunogenicity of HPG4.1 k-HIS Polypeptide

The obtained transformants of *E.coli* were inoculated to 200 ml of Circle Grow medium containing 50 µg/ml of ampicillin and cultured at 37° C. for 3 hours. Thereto was added IPTG (final concentration of 1 mM) and the transformants were cultured at 37° C. for additional 3 hours. The cells were harvested from the culture by centrifugation and suspended in 10 ml of PBS. To the suspension was added lysozyme at 100 µg/ml for reaction at 4° C. for 1 hour. The suspension was sonicated at 4° C. for 10 minutes for bacteriolysis. Intact cells were removed by centrifugation and the obtained supernatant was used as a crude HPG4.1 k-HIS polypeptide.

Ten SPF white leghorn chickens 5 weeks old were immunized by subcutaneously administering at the leg 0.5 ml of an emulsion prepared by thoroughly mixing the crude HPG4.1 k-HIS polypeptide solution with the same amount of Freund's complete adjuvant. About three weeks later, the chickens were subcutaneously administered at the leg with 0.5 ml of an emulsion prepared similarly with Freund's incomplete adjuvant. Two weeks later, the chickens were boosted subcutaneously at the leg with an emulsion prepared similarly with Freund's incomplete adjuvant. Seven weeks after the first immunization, the chickens were challenged with *Haemophilus paragallinarum* serotype A strain 221. As a control, as described in Example 2 (7), one group was immunized with formalin-inactivated HPG serotype A strain 221 and another group was not immunized and both control groups were challenged similarly. The results are shown in Table 4. The group immunized with the crude HPG4.1 k-HIS polypeptide showed protection against the onset of the disease in every ten among the tested chickens. The group immunized with the formalin-inactivated cells exhibited protection against the onset of the disease in all the chickens whereas the non-immunization group showed the symptoms in all the chickens.

TABLE 4

| Immunization group | Tested chicken | Protected chicken | Protection rate (%) |
|---|---|---|---|
| Crude HPGp4.1k-HIS | 10 | 10 | 100 |
| Formalin-inactivated strain 221 | 10 | 10 | 100 |
| Non immunization control | 10 | 0 | 0 |

(10) Nucleotide Sequence of HPG4.1 k DNA Fragment

A nucleotide sequence of a region in HPG4.1 k DNA fragment which does not overlap with HPG3.5 k DNA fragment, i.e. a region ranging from the HindIII cleavage site to the XbaI cleavage site, was analyzed with a DNA sequencer as described above. As a result, a sequence of 2831 nucleotides was determined. The analyzed nucleotide sequence of HPG4.1 k DNA fragment corresponds to the nucleotide sequence of from nucleotides No. 3445 to No. 6275 in SEQ ID NO: 1. No termination codon was found within the region of said DNA fragment. A corresponding amino acid sequence is also shown.

(11) Cloning of HPG6.7 k DNA

After the genomic DNA of *Haemophilus paragallinarum* serotype A strain 221 was cleaved with XhoI and PstI, a Southern hybridization was carried out as described in Example 3 (3) using the DIG-labeled HPG3.5 k DNA or the DIG-labeled HPG1.2 k DNA as a probe. As a result, DNAs of about 9.4 kb, about 6.7 kb and about 1 kb were detected with the DIG-labeled HPG3.5 k DNA as a probe. When the DIG-labeled HPG1.2 k DNA was used as a probe, DNAs of about 6.7 kb and about 1 kb were detected. Since there are two XhoI cleavage sites within the HPG3.5 k DNA fragment as described above, it was considered that the DNA of about 9.4 kb was a fragment corresponding to the 5' site from the first XhoI cleavage site, the DNA of about 6.7 kb was a fragment corresponding to the 3' site from the second XhoI cleavage site and the DNA of about 1 kb was a fragment between these two XhoI sites. Thus, the fragment of about 6.7 kb was separated and recovered on 0.8% agarose gel electrophoresis.

Figure 9:
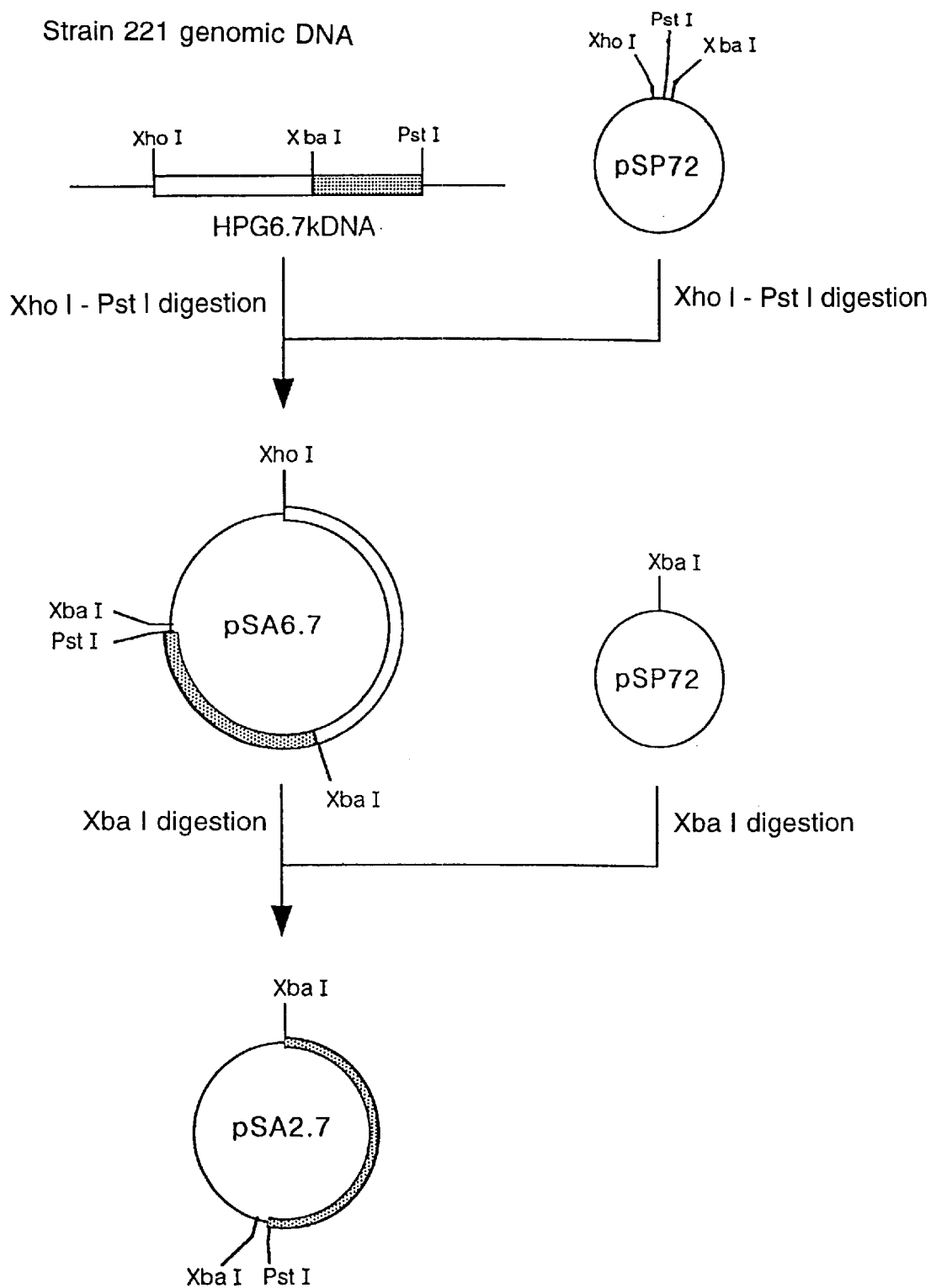
FIG. 9 is a schematic illustration showing construction of plasmid pSA6.7 by inserting the XhoI-PstI fragment (HPG6.7 k DNA) from the genome of *Haemophilus paragallinarum* serotype A strain 221 into plasmid pSP72, followed by construction of plasmid pSA2.7 by inserting the XbaI fragment from the plasmid pSA6.7 into plasmid pSP72.

As shown in FIG. 9, plasmid pSP72 was digested with XhoI and PstI and, after dephosphorizing the 5' end, ligated with the above XhoI-PstI digest (about 6.7 kb) derived from the genome of *Haemophilus paragallinarum* serotype A strain 221. *E.coli* strain JM109 cells were transformed with the ligated product. For the obtained *E.coli* transformants, a colony hybridization was carried out using the DIG-labeled HPG3.5 k DNA as a probe to screen positive clones.

The positive clones were cultured on CIRCLE GROW medium containing 50 µg/ml of ampicillin. Plasmids were recovered from the cells by PEG precipitation method. The obtained recombinant plasmid is hereinafter referred to as "pSA6.7". *E.coli* SA6.7JM transformed with the recombinant plasmid has been deposited by the applicant as FERM BP-6081 at National Institute of Bioscience and Human-Technology Agency of Industrial Science and Technology (1-3, Higashi 1-chome, Tsukuba-shi, Ibaraki-ken) on Aug. 27, 1997.

(12) Cloning of HPG2.7 k DNA

Since the DNA fragment of about 6.7 kb (hereinafter referred to as "HPG6.7 k DNA") incorporated in the obtained recombinant plasmid (pSA6.7) encompasses the above HPG4.1 k DNA, a fragment of about 2.7 kb (hereinafter referred to as "HPG2.7 k DNA") was subcloned which is a subtraction of HPG4.1 k DNA from HPG6.7 k DNA. pSA6.7 was digested with XbaI and then electrophoresed on 0.8% agarose gel to separate and recover a DNA fragment of about 2.7 kb which was the above HPG2.7 k DNA added with PstI-XbaI fragment from the plasmid pSP72.

Plasmid pSP72 was then digested with XbaI and, after dephosphorizing the 5' end, ligated with the above XbaI digest of about 2.7 kb. *E.coli* strain JM109 cells were transformed with the ligated product. The obtained *E.coli* transformants were cultured on CIRCLE GROW medium containing 50 μg/ml of ampicillin. Plasmids were recovered from the cells by PEG precipitation method. The obtained recombinant plasmid is hereinafter referred to as "pSA2.7".

(13) Nucleotide Sequence of HPG2.7 k DNA

A nucleotide sequence of HPG2.7 k DNA fragment was analyzed with a DNA sequencer as described above. As a result, a sequence of 2661 nucleotides was determined. The nucleotide sequence of HPG2.7 k DNA fragment corresponds to the nucleotide sequence of from nucleotides No. 6270 to No. 8930 in SEQ ID NO: 1. A termination codon was found within the region. A corresponding amino acid sequence is also shown.

It was found that the nucleotide sequence of SEQ ID NO: 1, consisting of a total of 8930 nucleotides, included an open reading frame starting from nucleotide No. 243 which can code for 2042 amino acid residues. A polypeptide comprising the 2042 amino acid residues is hereinafter referred to as "serotype A HMTp210". Homology search with the existing data base (GeneBank and EMBL) revealed no homology with any known nucleotide and amino acid sequences, indicating that the serotype A HMTp120 polypeptide is a novel substance.

The presence of another possible open reading frame in the nucleotide sequence of SEQ ID NO: 1 was also suggested which starts from nucleotide No. 8375 and can code for 185 amino acid residues. No termination codon was found in this sequence. Homology search with the existing data base (GeneBank and EMBL) revealed no homology with any known nucleotide and amino acid sequences, indicating that the polypeptide coded by this open reading frame is also a novel substance.

EXAMPLE 4

Search for DNA Fragment Hybridizable to HPG1.2 k DNA from Other Strains than *Haemophilus paragallinarum* Serotype A strain 221

As described in Example 3 (1), genomic DNAs were prepared from a total of nine strains, i.e. HPG serotype A strains 221, 083, W, Germany and Georgia, HPG serotype B strains Spross and 0222, and HPG serotype C strains Modesto and 53-47. After the prepared genomic DNAs were cleaved with restriction enzyme EcoRI, a Southern hybridization was carried out using the DIG-labeled HPG1.2 k DNA as a probe as described in Example 3 (3). As a result, fragments hybridizable with HPG1.2 k DNA were detected in every strains although size of each fragment was varied depending on the strains (FIG. 10).

EXAMPLE 5

Cloning of Gene Coding for Polypeptide (Serotype C HMTp210) from *Haemophilus paragallinarum* Serotype C (1) Screening from Genomic Library A genomic library of *Haemophilus paragallinarum* serotype C strain 53-47 was prepared in the same manner as described in Example 3 (1). That is, a genomic DNA of HPG serotype C strain 53-47 digested with restriction enzyme HindIII was ligated to λDASHII (manufactured by STRATAGENE) arm digested with restriction enzyme HindIII using cDNA Rapid Cloning Module-λgt11. Using λ-DNA in vitro packaging module, the ligated product was inserted into λ phage. The obtained solutions of recombinant phage were used as a genomic library.

The above solutions of genomic library were added to a suspension of *E.coli* strain XL1-Blue MRA (P2) (manufactured by STRATAGENE) about $10^8$ cells in an aqueous solution of 10 mM magnesium sulfate for absorption at 37° C. for 15 minutes. Thereto was added LB soft agarose medium (containing tryptone 10 g, yeast extract 5 g, sodium chloride 10 g, ampicillin 50 mg, maltose 4 g and agarose 8 g in 1000 ml, pH 7) for overlay warmed at 45° C. The mixture was overlaid to LB agar medium and incubated at 37° C. overnight. To the agar medium where transformed *E.coli* grown was overlaid Hybond N+ membrane to lift the phage plaques. Using the DIG-labeled serotype A HPG3.5 k DNA as a probe, a plaque hybridization was carried out in the conventional manner and positive clones were screened. About 1,000 plaques were immunologically screened as described above to give 37 positive plaques. Ten among the obtained positive plaques were further subjected to second and third screening as in the primary screening.

The recombinant λDASHII phages found positive in the plaque hybridization were added to a suspension of *E. coli* strain XL1-Blue MRA (manufactured by STRATAGENE) about $10^8$ cells in an aqueous solution of 10 mM magnesium sulfate for absorption at 37° C. for 15 minutes. As described in Example 3 (1), the phage DNA was recovered. The obtained phage DNA was digested with HindIII and then electrophoresed on 0.8% agarose gel to separate and recover DNA fragments derived from *Haemophilus paragallinarum* serotype C strain 53-47. All the DNA fragments obtained from ten positive phages had a length of about 13.5 kb. A DNA fragment (hereinafter referred to as "HPG-C1 DNA") obtained from the phage of a clone (clone 1) was used in the following test.

(2) Fragmentation and Subcloning of HPG-C1 DNA

Since the HPG-C1 DNA of about 13.5 kb is too large to be subcloned into a plasmid vector, it was cleaved with several restriction enzymes and a suitable amount of the resulting DNA fragments was electrophoresed on 0.8% agarose gel. As a result, DNA fragments of about 6.9 kb, about 5.6 kb and about 0.9 kb were detected when digested with XbaI.

Plasmid pUC119 was digested with HindIII and XbaI and, after dephosphorizing the 5' end, ligated with the above XbaI digests of HPG-C1 DNA. *E.coli* strain JM109 cells were transformed with the ligated products. Furthermore, *E.coli* cells transformed with the recombinant plasmid containing either DNA fragment of about 5.6 kb or about 0.9 kb were cultured and the plasmids were recovered from the cells by PEG precipitation method. The obtained recombinant plasmids (hereinafter referred to as "pU-C2" and "pU-C3", containing either DNA fragment of about 5.6 kb and about 0.9 kb, respectively) was digested with HindIII-XbaI and then electrophoresed on 0.8% agarose gel to separate and recover DNA fragments of about 5.6 kb and about 0.9 kb (hereinafter referred to as "HPG-C2 DNA" and "HPG-C3 DNA" respectively). *E.coli* U-C2JM transformed with the recombinant plasmid pU-C2 has been deposited by the applicant as FERM BP-6082 at National Institute of Bioscience and Human-Technology Agency of Industrial Science and Technology (1-3, Higashi 1-chome, Tsukuba-shi, Ibaraki-ken) on Aug. 27, 1997.

Plasmid pUC119 was digested with XbaI and, after dephosphorizing the 5' end, ligated with the above XbaI digests of HPG-C1 DNA. *E.coli* strain JM109 cells were transformed with the ligated products. Furthermore, *E.coli* cells transformed with the recombinant plasmid containing DNA fragment of about 6.9 kb were cultured and the plasmid was recovered from the cells by PEG precipitation method. The obtained recombinant plasmid (hereinafter referred to as "pU-C4") was digested with XbaI and then electrophoresed on 0.8% agarose gel to separate and recover DNA fragment of about 6.9 kb (hereinafter referred to as "HPG-C4 DNA"). *E.coli* U-C4JM transformed with the recombinant plasmid pU-C4 has been deposited by the applicant as FERM BP-6080 at National Institute of Bioscience and Human-Technology Agency of Industrial Science and Technology (1–3, Higashi 1-chome, Tsukuba-shi, Ibaraki-ken) on Aug. 27, 1997.

Figure 11:
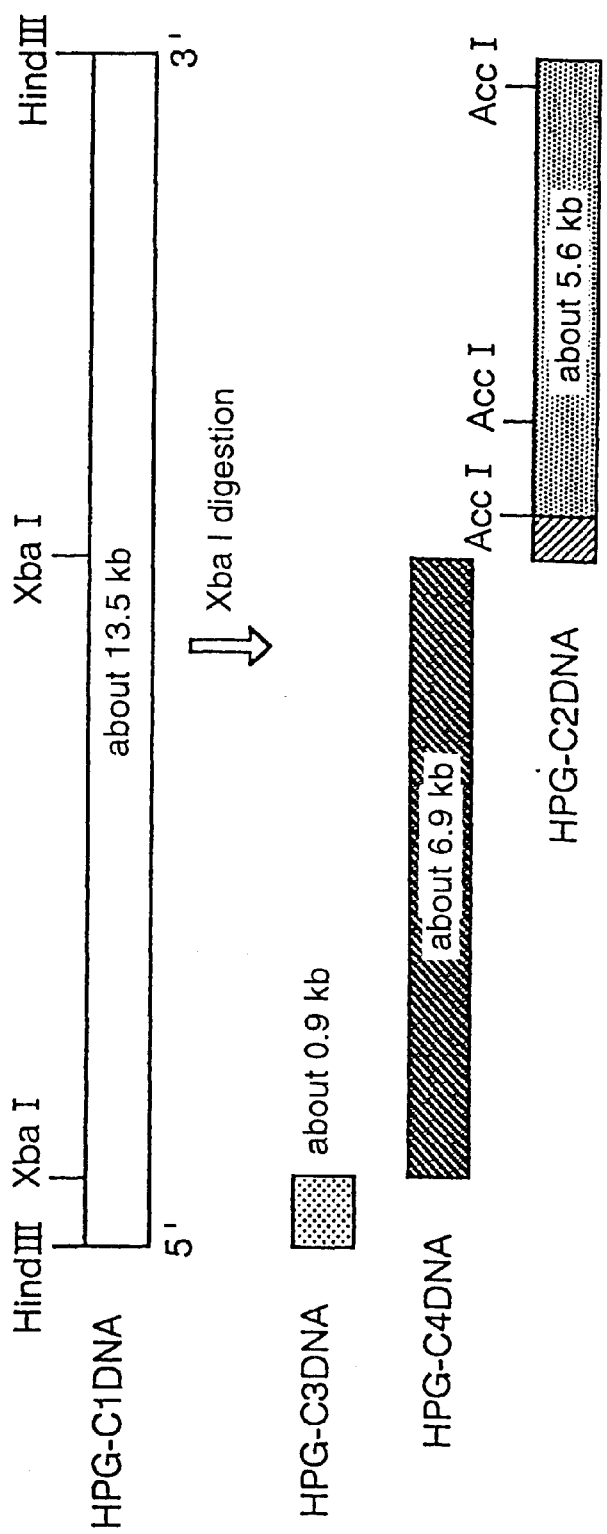
FIG. 11 is a schematic illustration showing the position of HPG-C1 DNA, HPG-C2 DNA, HPG-C3 DNA and HPG-C4 DNA fragments cloned from the genome of *Haemophilus paragallinarum* serotype C strain 53-47.
Figure 12:
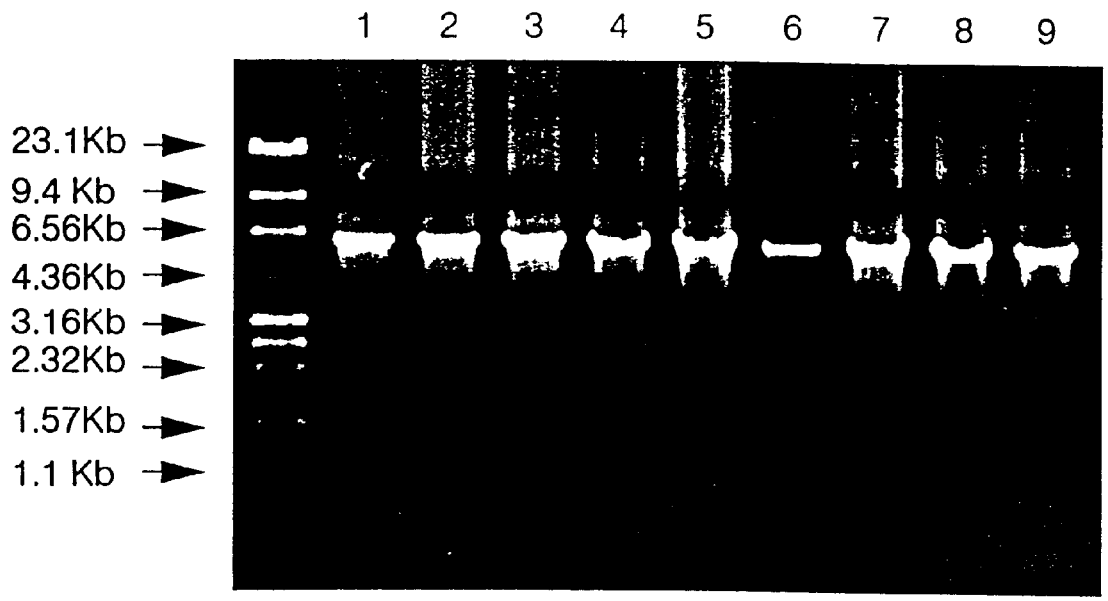
FIG. 12 is a photograph showing the result of 0.8% agarose gel electrophoresis of PCR products obtained by PCR with primers prepared on the basis of the nucleotide sequences coding for the N-terminal and C-terminal amino acid sequences of HPG serotype A HMTp210 polypeptide and the genome of *Haemophilus paragallinarum* serotype A, B or C as a template.

Each of the obtained DNA fragments HPG-C2, HPG-C3 and HPG-C4 was spotted on Hybond N+ membrane. Then, a dot hybridization was carried out using as a probe either the above DIG-labeled HPG3.5 k DNA or HPG4.1 k or HPG2.7 k DNA labeled similarly with DIG. When the DIG-labeled HPG3.5 k DNA or DIG-labeled HPG4.1 k DNA was used as a probe, HPG-C4 DNA was detected. On the other hand, when HPG2.7 k DNA was used as a probe, HPG-C2 DNA was detected. From this, it was assumed that HPG-C3, HPG-C4 and HPG-C2 were positioned in this order from the 5' site and HPG-C4 mainly encompasses a region coding for the polypeptide as shown in FIG. 11.

(3) Nucleotide Sequence of HPG-C4 DNA Fragment

A nucleotide sequence of HPG-C4 DNA fragment was analyzed with a DNA sequencer as described above. As a result, a sequence of 6871 nucleotides was determined. The nucleotide sequence of HPG-C4 DNA fragment corresponds to the nucleotide sequence of from nucleotides No. 1 to No. 6871 in SEQ ID NO: 5. Based on high homology with the gene coding for serotype A HMTp210, an open reading frame was obtained from HPG-C4 DNA in the same frame as that of the gene coding for serotype A HMTp120 and it was found that translation starts at nucleotide No. 848 to code for 2008 amino acid residues. However, no termination codon was found within the region of said DNA fragment. A corresponding amino acid sequence was also shown.

(4) Nucleotide Sequence of a Portion of HPG-C2 DNA Fragment

Since no termination codon was found within the region of HPG-C4 DNA fragment, a nucleotide sequence at the 5' site of HPG-C2 DNA fragment, which is at the 3' site of HPG-C4 DNA fragment, was analyzed. As shown in FIG. 11, there are three AccI cleavage sites within HPG-C2 DNA fragment. It was also revealed that a fragment ranging from the cloning site, i.e. XbaI cleavage site, to the first AccI cleavage site is of size about 0.6 Kb as demonstrated in an agarose gel electrophoresis. Thus, a nucleotide sequence of this fragment of about 0.6 Kb was analyzed with a DNA sequencer as described above. As a result, a sequence of 621 nucleotides was determined. The nucleotide sequence of a portion of HPG-C2 DNA fragment corresponds to the nucleotide sequence of from nucleotides No. 6866 to No. 7486 in SEQ ID NO: 5. A termination codon was found within the region of this portion of HPG-C2 DNA fragment. A corresponding amino acid sequence was also shown.

It was found that the nucleotide sequence of SEQ ID NO: 5, consisting of a total of 7486 nucleotides, included an open reading frame starting from nucleotide No. 848 which can code for 2039 amino acid residues. A polypeptide comprising the 2039 amino acid residues is hereinafter referred to as "serotype C HMTp210". Homology search with the existing data base (GeneBank and EMBL) revealed no homology with any known nucleotide and amino acid sequences, indicating that the serotype C HMTp120 polypeptide is a novel substance.

Homology search between the nucleotide sequences coding for the serotype C HMTp120 polypeptide and the serotype A HMTp120 polypeptide revealed about 80% homology. It was further revealed that the region of about 3.4 kb at the 5' site and the region of about 1.2 kb at the 3' site exhibited extremely high homology whereas the region of about 1.5 kb between these 5' and 3' regions showed low homology. The same was also applicable to the corresponding polypeptides encoded by these genes.

EXAMPLE 6

PCR Amplification of HMTp120 Gene from Genomic DNA of HPG Serotypes A, B and C Cells As described in Example 3 (1), genomic DNAs were prepared from a total of nine strains, i.e. HPG serotype A strains 221, 083, W, Germany and Georgia, HPG serotype B strains Spross and 0222, and HPG serotype C strains Modesto and 53-47. Based on the nucleotide sequence coding for the Type A HMTp120 polypeptide, there were prepared a synthetic DNA having the nucleotide sequence of SEQ ID NO: 3 as an upstream PCR primer and a synthetic DNA having the nucleotide sequence of SEQ ID NO: 4 as a downstream PCR primer. These primers were designed such that BamHI recognition sequences were added at the 5' site, respectively, and a full length of translation region of the serotype A HMTp120 polypeptide can be amplified. Using these primers, PCR was carried out using the genomic DNAs prepared as mentioned above as a template. PCR was carried out with LA PCR Kit ver. 2 (manufactured by Takara Shuzo K.K.) under the following conditions: after reaction at 94° C. for 1 minute, 30 cycles of reactions at 98° C. for 40 seconds and at 60° C. for 10 minutes, followed by reaction at 72° C. for 10 minutes. Analysis of the obtained PCR products on 0.8% agarose gel electrophoresis confirmed the amplified fragment of about 6.1 Kb in any of these strains (FIG. 12).

EXAMPLE 7

Expression of Full-length Serotypes A and C HMTp210 Polypeptides (1) Expression of Serotype A HMTp120 Polypeptide The PCR product obtained in Example 6 with the genomic DNA from *Haemophilus paragallinarum* serotype A strain 221 as a template was digested with BamHI. After separation on 0.8% agarose gel electrophoresis, the amplified fraction of about 6.1 Kb was eluted and recovered with Sephaglas™ BandPrep Kit.

Plasmid pUC119 was digested with BamHI and, after dephosphorizing the 5' end, ligated with the above amplified fragment of about 6.1 kb. *E.coli* strain JM109 cells were transformed with the ligated product. Furthermore, *E.coli* cells transformed with the recombinant plasmid containing DNA fragment of about 6.1 kb were cultured and the plasmid was recovered from the cells by PEG precipitation method. The obtained recombinant plasmid (hereinafter referred to as "pU-AP1") was digested with BamHI and then electrophoresed on 0.8% agarose gel to separate and recover DNA fragment of about 6.1 kb (hereinafter referred to as "HPG-AP1 DNA").

As described in Example 3 (4), the expression vector pTrcHisA (manufactured by Invitrogen) was digested with BamHI and, after dephosphorizing the 5' end, ligated with the above HPG-AP1 DNA. *E.coli* strain JM109 cells were transformed with the ligated product. From the obtained transformants of *E.coli*, there was obtained *E.coli* which was transformed with a recombinant plasmid wherein HPG-AP1 DNA was ligated in a right direction and expressed an antigen specifically reactive with anti-HPGp130 guinea pig serum.

(2) Expression of Serotype C HMTp120 Polypeptide

The PCR product obtained in Example 6 with the genomic DNA from *Haemophilus paragallinarum* serotype C strain 53-47 as a template was digested with BamHI. After separation on 0.8% agarose gel electrophoresis, the amplified fraction of about 6.1 Kb was recovered.

Plasmid pUC119 was digested with BamHI and, after dephosphorizing the 5' end, ligated with the above amplified fragment of about 6.1 kb. *E.coli* strain JM109 cells were transformed with the ligated product. Furthermore, *E.coli* cells transformed with the recombinant plasmid containing DNA fragment of about 6.1 kb were cultured and the plasmid was recovered from the cells by PEG precipitation method. The obtained recombinant plasmid (hereinafter referred to as "pU-CP1") was digested with BamHI and then electrophoresed on 0.8% agarose gel to separate and recover DNA fragment of about 6.1 kb (hereinafter referred to as "HPG-CP1 DNA").

As described in Example 3 (4), the expression vector pTrcHis A (manufactured by Invitrogen) was digested with BamHI and, after dephosphorizing the 5' end, ligated with the above HPG-CP1 DNA. *E.coli* strain JM109 cells were transformed with the ligated product. From the obtained transformants of *E.coli,* there was obtained *E.coli* which was transformed with a recombinant plasmid wherein HPG-CP1 DNA was ligated in a right direction and expressed an antigen specifically reactive with anti-HPGp130 guinea pig serum.

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 8930 base pairs
        (B) TYPE: nucleic acid
        (C) STRANDEDNESS: double
        (D) TOPOLOGY: linear (ii) MOLECULE TYPE: genomic DNA (vi) ORIGINAL SOURCE:

(ix) FEATURE:
        (A) NAME/KEY: CDS
        (B) LOCATION: 8374..8929

(xi) SEQUENCE DESCRIPTION: SEQ ID NO: 1:

```
AAGCTTTTTC GGGCGATTGA AGACGGAATG TTACTTTGGC AAGCGGTTTG AAACCTTTGA        60

ACAGCTTGAA AAAGTGATTC ACGAGTACAT TCATTACTAC AACAATGAGC GTATTCAAG       120

GAAGCTCAAA GGACTAAGCC CTGTGGAATA CAGAACTCAG TCCTTGAATG AAATTAGAA       180

ATAGTCTAAC TTTTTGGGGC AGATCAACAC TCATTTTTAA TATTAATATA GGAAAATGA       240

TT ATG AAT AAA GTT TTT AAA ATT AAA TAT TCT GTT GTA AAA CAA GAA        287
   Met Asn Lys Val Phe Lys Ile Lys Tyr Ser Val Val Lys Gln Glu
       -70             -65                 -60

ATG ATT GTG GTT TCA GAG CTA GCA AAT AAT AAA GAT AAA ACA GCT AGC       335
Met Ile Val Val Ser Glu Leu Ala Asn Asn Lys Asp Lys Thr Ala Ser
-55                 -50                 -45                 -40

CAA AAA AAC ACA CAT AAT ACT GCA TTT TTT CAA CCG CTA TTT ACA AAG       383
Gln Lys Asn Thr His Asn Thr Ala Phe Phe Gln Pro Leu Phe Thr Lys
                -35                 -30                 -25

TGT ACA TAT CTT GCT CTT CTC ATT AAT ATC GCA CTA GGA GCA TCA TTA       431
Cys Thr Tyr Leu Ala Leu Leu Ile Asn Ile Ala Leu Gly Ala Ser Leu
```

```
                -20              -15              -10
TTC CCT CAA TTA GCT AAT GCG AAG TGG TTA GAG GTT TAT AGT AGC TCC      479
Phe Pro Gln Leu Ala Asn Ala Lys Trp Leu Glu Val Tyr Ser Ser Ser
         -5                   1               5

GTA AAA CTA TCT ACT GTT AGT GCA CAA AGT AAT AGT GTT AAT CTT AAT      527
Val Lys Leu Ser Thr Val Ser Ala Gln Ser Asn Ser Val Asn Leu Asn
10               15                  20                  25

CCA TCG GGA GCT GAG AGT GTT GGC ACA AAT AGC CCA CAA GGG GTT GCT      575
Pro Ser Gly Ala Glu Ser Val Gly Thr Asn Ser Pro Gln Gly Val Ala
                 30                  35                  40

ATT GGC TAT GGT GCA ACC AAC GAT AGA TCT GCA ACA GGA GCT ATT GCT      623
Ile Gly Tyr Gly Ala Thr Asn Asp Arg Ser Ala Thr Gly Ala Ile Ala
             45                  50                  55

CTT GGG GTT GGG GTA AAA AAT GAA ACT TTA GCG AAA GAC TCT ATT GCC      671
Leu Gly Val Gly Val Lys Asn Glu Thr Leu Ala Lys Asp Ser Ile Ala
             60                  65                  70

ATT GGT TAT GGG GCA AAA AAT GAA AGC ACA GCA CCA AGT TCT GTG ACT      719
Ile Gly Tyr Gly Ala Lys Asn Glu Ser Thr Ala Pro Ser Ser Val Thr
75               80                  85

ATT GGA AAA CAG GCG ATT AAC CGT TTT GAA AAA TCT ATT GTG ATG GGT      767
Ile Gly Lys Gln Ala Ile Asn Arg Phe Glu Lys Ser Ile Val Met Gly
90               95                  100                 105

CTT AAT GCT TAT ACA CAA TTA GAT CCC CGT GGA ACT AGT AAA GAA ACC      815
Leu Asn Ala Tyr Thr Gln Leu Asp Pro Arg Gly Thr Ser Lys Glu Thr
                 110                 115                 120

CGT CAA GGT TCT GTA GTG ATT GGG GAA AAT GCG AAA AGT GCT GGG AAT      863
Arg Gln Gly Ser Val Val Ile Gly Glu Asn Ala Lys Ser Ala Gly Asn
             125                 130                 135

CAA TCT GTT TCT TTA GGG CAA AAT TCG TGG TCA AAA ACC AAT TCT ATT      911
Gln Ser Val Ser Leu Gly Gln Asn Ser Trp Ser Lys Thr Asn Ser Ile
             140                 145                 150

TCT ATT GGG GCA GGA ACC TTT GCG GAA GGA AAA TCA AGC ATT GCT ATA      959
Ser Ile Gly Ala Gly Thr Phe Ala Glu Gly Lys Ser Ser Ile Ala Ile
155                  160                 165

GGG ACT GAT AAA ATA TCA GGG ACT AAG TAT AAT GAC AAA TTG CCT GCT     1007
Gly Thr Asp Lys Ile Ser Gly Thr Lys Tyr Asn Asp Lys Leu Pro Ala
170              175                 180                 185

ACT GCT TGG AAT GGA ACA GGC ACT GTT CCG AAA AAC TCC ATT TGG GAT     1055
Thr Ala Trp Asn Gly Thr Gly Thr Val Pro Lys Asn Ser Ile Trp Asp
                 190                 195                 200

ATA TTT TCT GAG TTA TAT ATG GGG AAA CAG ACT AAC GGC AGA GAT TAT     1103
Ile Phe Ser Glu Leu Tyr Met Gly Lys Gln Thr Asn Gly Arg Asp Tyr
             205                 210                 215

GAT ACA ACT ACT CGA GAC CCT AAT AAA CCG GAG GCA TTT TAT AAA TTT     1151
Asp Thr Thr Thr Arg Asp Pro Asn Lys Pro Glu Ala Phe Tyr Lys Phe
             220                 225                 230

AGC GAT TTT AAA GGA AAA TAT GTC AAT ACC CCA ACT GCT TCA CCT ACT     1199
Ser Asp Phe Lys Gly Lys Tyr Val Asn Thr Pro Thr Ala Ser Pro Thr
         235                 240                 245

TAT GCA GGG AAA TTA GGG GCA ATT GCT CTA GGT TCC CGC ACC ATT GCC     1247
Tyr Ala Gly Lys Leu Gly Ala Ile Ala Leu Gly Ser Arg Thr Ile Ala
250                  255                 260                 265

GCG GGG GAA ATG TCC ACC GCA GTG GGT TCG TTA GCC TTT GCA TTG GCA     1295
Ala Gly Glu Met Ser Thr Ala Val Gly Ser Leu Ala Phe Ala Leu Ala
                 270                 275                 280

GAT AGA TCC ACC GCA ATG GGG TTA CGT TCT TTT GTT GCT AAA GAC GCC     1343
Asp Arg Ser Thr Ala Met Gly Leu Arg Ser Phe Val Ala Lys Asp Ala
             285                 290                 295

GTA GGT GGA ACG GCG ATC GGG GAA GAA TCT CGA ACC TTT GCT AAA GAT     1391
```

-continued

```
Val Gly Gly Thr Ala Ile Gly Glu Glu Ser Arg Thr Phe Ala Lys Asp
            300                 305                 310

TCC GTT GCC ATT GGT AAT AAA ACT GAA GCC TCA AAT GCT GGC TCA ATG    1439
Ser Val Ala Ile Gly Asn Lys Thr Glu Ala Ser Asn Ala Gly Ser Met
315                 320                 325

GCT TAT GGT TAT AAG GCG AAA GCA GTA GGT GCG GGA GCA ATC GCA ATT    1487
Ala Tyr Gly Tyr Lys Ala Lys Ala Val Gly Ala Gly Ala Ile Ala Ile
330                 335                 340                 345

GGG ACA GAA GTC GCA GCA GGG GCT AAA TTT AAT AGC CAT CAA ACA GGA    1535
Gly Thr Glu Val Ala Ala Gly Ala Lys Phe Asn Ser His Gln Thr Gly
                350                 355                 360

AAT TTA CTA CAG GAT AAT AAT GCT TAT GCT ACC TTA AAA AAT GCC GAT    1583
Asn Leu Leu Gln Asp Asn Asn Ala Tyr Ala Thr Leu Lys Asn Ala Asp
            365                 370                 375

AAA TCA GAT GAT ACT AAA ACC GGA AAT GCG ATT ACT GTA TTT ACC CAG    1631
Lys Ser Asp Asp Thr Lys Thr Gly Asn Ala Ile Thr Val Phe Thr Gln
        380                 385                 390

TCT TTT GAT AAT ATG CTT ACT AAT GGA TTA CCG CTG GTA AGT GAA AAC    1679
Ser Phe Asp Asn Met Leu Thr Asn Gly Leu Pro Leu Val Ser Glu Asn
395                 400                 405

GAA ACC TAT TTA ACG ACC TCA GCG GGA GCA ATT AAA AAA ACT GCA ACA    1727
Glu Thr Tyr Leu Thr Thr Ser Ala Gly Ala Ile Lys Lys Thr Ala Thr
410                 415                 420                 425

ACA GAC AGC AGT GCG GGG GGA GGT AAA AAT GCC ATT GCA ATT GGT AGT    1775
Thr Asp Ser Ser Ala Gly Gly Gly Lys Asn Ala Ile Ala Ile Gly Ser
                430                 435                 440

AAA ACC TTT GCC TCT AAA GCA AAT TCT GTG GCA TTA GGG AGC TAT GCC    1823
Lys Thr Phe Ala Ser Lys Ala Asn Ser Val Ala Leu Gly Ser Tyr Ala
            445                 450                 455

TTA GCC GAT GCC CAA AAT GCC TTT GCA CTA GGT TCT TAT TCT TTT GTG    1871
Leu Ala Asp Ala Gln Asn Ala Phe Ala Leu Gly Ser Tyr Ser Phe Val
        460                 465                 470

GAA TCT TCA GCA ACA AAT ACA ATC ACA ATT GGT GTG GGA AGT TAT GCC    1919
Glu Ser Ser Ala Thr Asn Thr Ile Thr Ile Gly Val Gly Ser Tyr Ala
475                 480                 485

AAA GGG AAA AAC AGT TTC TTA GGG GGG ACT TGG GCA TCA ACC CTT TCA    1967
Lys Gly Lys Asn Ser Phe Leu Gly Gly Thr Trp Ala Ser Thr Leu Ser
490                 495                 500                 505

GAT CGG ACA GTT GTG CTA GGG AAT TCC ACT TCA ATT AGC TCA GGT TCT    2015
Asp Arg Thr Val Val Leu Gly Asn Ser Thr Ser Ile Ser Ser Gly Ser
                510                 515                 520

CAG AAT GCA TTA GCA ATC GGG GTG AAT GTC TTT ATT GGT AAT GAT AGT    2063
Gln Asn Ala Leu Ala Ile Gly Val Asn Val Phe Ile Gly Asn Asp Ser
            525                 530                 535

GCT TCT TCA TTG GCA TTA GGT ATG GGT TCT ACT ATT GCG AAA AGT GCC    2111
Ala Ser Ser Leu Ala Leu Gly Met Gly Ser Thr Ile Ala Lys Ser Ala
        540                 545                 550

AAA TCC CCT GAC AGC TTA GCC ATT GGT AAA GAG GCA CGA ATT GAC GCT    2159
Lys Ser Pro Asp Ser Leu Ala Ile Gly Lys Glu Ala Arg Ile Asp Ala
555                 560                 565

AAA GAT ACA GAT AAT GGT ACT TTG TAT CAG CCT CAA GTT TAT GAT GAA    2207
Lys Asp Thr Asp Asn Gly Thr Leu Tyr Gln Pro Gln Val Tyr Asp Glu
570                 575                 580                 585

ACT ACT CGA GCC TTT AGA AAC TTT AAT GAA AGT AGC GAT TAT ATG CGT    2255
Thr Thr Arg Ala Phe Arg Asn Phe Asn Glu Ser Ser Asp Tyr Met Arg
                590                 595                 600

CAA GCA ATG GCA TTA GGT TTT AAT GCT AAA GTT TCG CGT GGG GTG GGC    2303
Gln Ala Met Ala Leu Gly Phe Asn Ala Lys Val Ser Arg Gly Val Gly
            605                 610                 615
```

```
AAA ATG GAA ACG GGG ATT AAC TCG ATG GCG ATT GGT GCT TAT GCT CAA    2351
Lys Met Glu Thr Gly Ile Asn Ser Met Ala Ile Gly Ala Tyr Ala Gln
        620                 625                 630

GCA ACT TTG CAA AAT TCC ACC GCA CTT GGG GTA GGC TCT AAA ACA GAT    2399
Ala Thr Leu Gln Asn Ser Thr Ala Leu Gly Val Gly Ser Lys Thr Asp
            635                 640                 645

TAC ACT TGG GAA CAG TTA GAA ACC GAT CCT TGG GTA TCT GAA GGG GCA    2447
Tyr Thr Trp Glu Gln Leu Glu Thr Asp Pro Trp Val Ser Glu Gly Ala
650                 655                 660                 665

ATC AGT ATC CCA ACT TCA GGT AAA ACT GGG GTT ATC TCT GTG GGT TCA    2495
Ile Ser Ile Pro Thr Ser Gly Lys Thr Gly Val Ile Ser Val Gly Ser
                670                 675                 680

AAA GGT TCA GAA CGT CGT ATT GTG AAT CTT GCT TCG GGT TCT TCT GAT    2543
Lys Gly Ser Glu Arg Arg Ile Val Asn Leu Ala Ser Gly Ser Ser Asp
                    685                 690                 695

ACT GAT GCC GTG AAT GTT GCT CAG TTA AAA ACC GTT GAA GAA CGT TTC    2591
Thr Asp Ala Val Asn Val Ala Gln Leu Lys Thr Val Glu Glu Arg Phe
            700                 705                 710

CTA TCT GAA ATT AAT TTA TTA CAA AAT GGC GGT GGG GTG AAA TAT CTC    2639
Leu Ser Glu Ile Asn Leu Leu Gln Asn Gly Gly Gly Val Lys Tyr Leu
715                 720                 725

TCT GTT GAA AAA ACG AAT ATC AAT GGA CAA TCG GGG AGA GTG GCT AGC    2687
Ser Val Glu Lys Thr Asn Ile Asn Gly Gln Ser Gly Arg Val Ala Ser
730                 735                 740                 745

CAA ATT CGT AAA GGG GAA AAT TAT GAG CGA TAT GTG AAA TTA AAA ACA    2735
Gln Ile Arg Lys Gly Glu Asn Tyr Glu Arg Tyr Val Lys Leu Lys Thr
                750                 755                 760

CAA TTG CTC TAT TTA GAT GCA CGA GGA AAA TTA AAT GGA GAG AAG TTT    2783
Gln Leu Leu Tyr Leu Asp Ala Arg Gly Lys Leu Asn Gly Glu Lys Phe
                    765                 770                 775

GAT CAA AAT TCA TTA AAC AAA ATT CGT GCG GTA GTG CAA GAA CTT GAA    2831
Asp Gln Asn Ser Leu Asn Lys Ile Arg Ala Val Val Gln Glu Leu Glu
            780                 785                 790

GCG GAA TAT AGT GGC GAG TTA AAA ACA ACC GCG TCA GCT CTC AAT CAG    2879
Ala Glu Tyr Ser Gly Glu Leu Lys Thr Thr Ala Ser Ala Leu Asn Gln
795                 800                 805

GTT GCA ACA CAA TTA GAG CAA GAA GTA ACC ACA AAT AAC TTC GAC AAA    2927
Val Ala Thr Gln Leu Glu Gln Glu Val Thr Thr Asn Asn Phe Asp Lys
810                 815                 820                 825

TTT AAT CAA TAT AAA ACG CAG ATT GAG AAT GCA AGC AAT GCG GAT TCA    2975
Phe Asn Gln Tyr Lys Thr Gln Ile Glu Asn Ala Ser Asn Ala Asp Ser
                830                 835                 840

GCA AGA AAT GTA GGC GGC TTA ACC CCT CAA GCA ATT GCA CAG TTA AAA    3023
Ala Arg Asn Val Gly Gly Leu Thr Pro Gln Ala Ile Ala Gln Leu Lys
                    845                 850                 855

GCC AAT AAT AAC TAT CTT AAT GAT GGT GCA AAA GGG CAA GAC AGT ATT    3071
Ala Asn Asn Asn Tyr Leu Asn Asp Gly Ala Lys Gly Gln Asp Ser Ile
            860                 865                 870

GCA TTT GGC TGG CAG GCA AAA ACC TCA GGA GCT AAT AAT GGA TTA GCA    3119
Ala Phe Gly Trp Gln Ala Lys Thr Ser Gly Ala Asn Asn Gly Leu Ala
875                 880                 885

GGG AAA CAA GCC ATT GCG ATT GGT TTC CAA GCG AAT TCT TCC GCT GAA    3167
Gly Lys Gln Ala Ile Ala Ile Gly Phe Gln Ala Asn Ser Ser Ala Glu
890                 895                 900                 905

AAT GCC ATT TCA ATC GGC ACG AAT TCG GAT ACC TCA ATG ACA GGG GCA    3215
Asn Ala Ile Ser Ile Gly Thr Asn Ser Asp Thr Ser Met Thr Gly Ala
                910                 915                 920

GTG GCG ATT GGT AAA GGT GCA ACG GTT ACT GCG GGT GGA AAA CCT TCC    3263
Val Ala Ile Gly Lys Gly Ala Thr Val Thr Ala Gly Gly Lys Pro Ser
                    925                 930                 935
```

```
ATT GCA TTG GGG CAA GAT TCG ACG GTT GCC AAT TCC GCA ATT AGC CGT      3311
Ile Ala Leu Gly Gln Asp Ser Thr Val Ala Asn Ser Ala Ile Ser Arg
            940                 945                 950

ACA AGT TCA CCG ATG ATA AAT GGT TTA ATA TTC AAT AAT TTT GCA GGT      3359
Thr Ser Ser Pro Met Ile Asn Gly Leu Ile Phe Asn Asn Phe Ala Gly
        955                 960                 965

TCC CCT GAA ACA CTC GGT GTG TTA AGT ATC GGA ACG GCT GGG AGA GAG      3407
Ser Pro Glu Thr Leu Gly Val Leu Ser Ile Gly Thr Ala Gly Arg Glu
970                 975                 980                 985

CGT AAA ATT GTT AAT GTT GCA GCA GGC GAT GTT TCG CAA GCT TCT ACT      3455
Arg Lys Ile Val Asn Val Ala Ala Gly Asp Val Ser Gln Ala Ser Thr
                990                 995                 1000

GAA GCC ATT AAC GGC TCA CAG CTT TAT GCA ACG AAC TTT ATG TTG AGC      3503
Glu Ala Ile Asn Gly Ser Gln Leu Tyr Ala Thr Asn Phe Met Leu Ser
            1005                1010                1015

AAA GTG GCT CAA TCT GTT AAG AGC AAC TTT GGT GGC AAT GTA AAT CTT      3551
Lys Val Ala Gln Ser Val Lys Ser Asn Phe Gly Gly Asn Val Asn Leu
        1020                1025                1030

GGC ACT GAT GGC ACA ATT ACA TTT ACA AAT ATT GGC GGC ACA GGG CAA      3599
Gly Thr Asp Gly Thr Ile Thr Phe Thr Asn Ile Gly Gly Thr Gly Gln
    1035                1040                1045

GCT ACA ATC CAC GAT GCG ATT AAT AAT GTT CTC ACT AAA GGG ATC TAC      3647
Ala Thr Ile His Asp Ala Ile Asn Asn Val Leu Thr Lys Gly Ile Tyr
1050                1055                1060                1065

CTT AAA GCG GAT CAG AAT GAT CCA ACA GGA AAT CAA GGT CAG AAA GTG      3695
Leu Lys Ala Asp Gln Asn Asp Pro Thr Gly Asn Gln Gly Gln Lys Val
                1070                1075                1080

GAA CTT GGT AAT GCA ATA ACG CTT TCG GCA ACA AAT CAA TGG GCG AAT      3743
Glu Leu Gly Asn Ala Ile Thr Leu Ser Ala Thr Asn Gln Trp Ala Asn
            1085                1090                1095

AAC GGC GTA AAT TAT AAA ACG AAC AAT TTA ACC ACT TAT AAT TCA CAA      3791
Asn Gly Val Asn Tyr Lys Thr Asn Asn Leu Thr Thr Tyr Asn Ser Gln
        1100                1105                1110

AAT GGC ACG ATT TTA TTT GGA ATG CGT GAA GAT CCA AGT GTA AAA CAA      3839
Asn Gly Thr Ile Leu Phe Gly Met Arg Glu Asp Pro Ser Val Lys Gln
    1115                1120                1125

ATT ACA GCG GGA ACC TAT AAT ACA ACG GGT GAT GCG AAC AAT AAA AAT      3887
Ile Thr Ala Gly Thr Tyr Asn Thr Thr Gly Asp Ala Asn Asn Lys Asn
1130                1135                1140                1145

CAA CTA AAT AAT ACA CTT CAA CAA ACC ACG CTT GAA GCA ACT GGG ATC      3935
Gln Leu Asn Asn Thr Leu Gln Gln Thr Thr Leu Glu Ala Thr Gly Ile
                1150                1155                1160

ACC AGT AGC GTA GGT TCA ACT AAC TAC GCT GGC TTT AGC TTA GGG GCA      3983
Thr Ser Ser Val Gly Ser Thr Asn Tyr Ala Gly Phe Ser Leu Gly Ala
            1165                1170                1175

GAC AGC GTC ACC TTC TCG AAA GGT GGA GCT GGC ACG GTG AAA CTT TCT      4031
Asp Ser Val Thr Phe Ser Lys Gly Gly Ala Gly Thr Val Lys Leu Ser
        1180                1185                1190

GGC GTA AGC GAT GCC ACA GCC GAC ACC GAC GCT GCC ACT CTA AAA CAA      4079
Gly Val Ser Asp Ala Thr Ala Asp Thr Asp Ala Ala Thr Leu Lys Gln
    1195                1200                1205

GTG AAA GAA TAC CGC ACA ACA TTA GTG GGT GAT AAT GAC ATC ACC GCA      4127
Val Lys Glu Tyr Arg Thr Thr Leu Val Gly Asp Asn Asp Ile Thr Ala
1210                1215                1220                1225

GCA GAT CGT AGT GGC GGC ACA AGC AAT GGC ATT ACC TAC AAC TTA AGC      4175
Ala Asp Arg Ser Gly Gly Thr Ser Asn Gly Ile Thr Tyr Asn Leu Ser
                1230                1235                1240

CTT AAT AAA GGT ACG GTT TCG GCA ACA GAA GAA AAA GTG GTG TCA GGG      4223
Leu Asn Lys Gly Thr Val Ser Ala Thr Glu Glu Lys Val Val Ser Gly
```

```
            1245                1250                1255
AAA ACT GTC TAT GAA GCC ATT AGA AAT GCC ATC ACA GGC AAC ATC TTC    4271
Lys Thr Val Tyr Glu Ala Ile Arg Asn Ala Ile Thr Gly Asn Ile Phe
        1260                1265                1270

ACA ATT GGC TTA GAC GAT ACC ACC TTG AAC AAA ATC AAC AAT CCC GCG    4319
Thr Ile Gly Leu Asp Asp Thr Thr Leu Asn Lys Ile Asn Asn Pro Ala
    1275                1280                1285

GAT CAA GAT CTT TCA AAC CTC AGT GAA AGT GGC AAA AAT GCC ATT ACG    4367
Asp Gln Asp Leu Ser Asn Leu Ser Glu Ser Gly Lys Asn Ala Ile Thr
1290                1295                1300                1305

GGC TTA GTG GAT GTG GTG AAA AAA ACA AAT TCA CCG ATC ACA GTT GAG    4415
Gly Leu Val Asp Val Val Lys Lys Thr Asn Ser Pro Ile Thr Val Glu
                1310                1315                1320

CCT TCT ACC GAT AGC AAC AAG AAA AAA ACC TTC ACT GTA GGC GTG GAT    4463
Pro Ser Thr Asp Ser Asn Lys Lys Lys Thr Phe Thr Val Gly Val Asp
            1325                1330                1335

TTC ACC GAT ACC ATT ACG GAA GGT GAC GCA ACG GAT GAT AAA AAA CTG    4511
Phe Thr Asp Thr Ile Thr Glu Gly Asp Ala Thr Asp Asp Lys Lys Leu
        1340                1345                1350

ACG ACT TCA AAA TCC GTT GAA AGC TAT GTC ACA AAC AAA CTC GCG AAC    4559
Thr Thr Ser Lys Ser Val Glu Ser Tyr Val Thr Asn Lys Leu Ala Asn
    1355                1360                1365

TTC TCT ACA GAT ATT TTG TTA TCG GAT GGG CGT TCT GGT AAC GCA ACA    4607
Phe Ser Thr Asp Ile Leu Leu Ser Asp Gly Arg Ser Gly Asn Ala Thr
1370                1375                1380                1385

ACG GCA AAT GAT GGG GTG GGT AAA CGT CGT TTG TCT GAT GGC TTT ACG    4655
Thr Ala Asn Asp Gly Val Gly Lys Arg Arg Leu Ser Asp Gly Phe Thr
                1390                1395                1400

ATC AAA TCT GAA AAC TTT ACG CTA GGT TCA AAA CAA TAT AAT GGC TCT    4703
Ile Lys Ser Glu Asn Phe Thr Leu Gly Ser Lys Gln Tyr Asn Gly Ser
            1405                1410                1415

GAT AGC TTA GGG GTA ATG TAT GAC GAT CAA AAT GGG GTC TTT AAA TTA    4751
Asp Ser Leu Gly Val Met Tyr Asp Asp Gln Asn Gly Val Phe Lys Leu
        1420                1425                1430

AGC CTA AAT ATG ACC GCA CTT ACC ACT TCA TTG GCT AAT ACT TTC GCG    4799
Ser Leu Asn Met Thr Ala Leu Thr Thr Ser Leu Ala Asn Thr Phe Ala
    1435                1440                1445

AAG TTG GAT GCC TCT AAC CTT ACT GAT GAT AGC AAT AAA GAG AAA TGG    4847
Lys Leu Asp Ala Ser Asn Leu Thr Asp Asp Ser Asn Lys Glu Lys Trp
1450                1455                1460                1465

CGT ACT GCG TTG AAT GTG TAT TCA AAA ACA GAA GTA GAT GCA GAA ATT    4895
Arg Thr Ala Leu Asn Val Tyr Ser Lys Thr Glu Val Asp Ala Glu Ile
                1470                1475                1480

CAA AAA TCC AAG GTA ACA CTC ACA CCA GAT TCG GGT TTG ATC TTT GCG    4943
Gln Lys Ser Lys Val Thr Leu Thr Pro Asp Ser Gly Leu Ile Phe Ala
            1485                1490                1495

ACC AAA CAA GCT GGG AGT GGT AAT AAC GCA GGT ATT GAT GCT GGG AAT    4991
Thr Lys Gln Ala Gly Ser Gly Asn Asn Ala Gly Ile Asp Ala Gly Asn
        1500                1505                1510

AAG AAA ATT AGT AAT GTC GCC GAT GGG GAT ATT TCT CCA ACC AGT GGT    5039
Lys Lys Ile Ser Asn Val Ala Asp Gly Asp Ile Ser Pro Thr Ser Gly
    1515                1520                1525

GAT GTA GTG ACA GGT CGT CAG CTC TAC GCC TTA ATG CAG AAA GGT ATT    5087
Asp Val Val Thr Gly Arg Gln Leu Tyr Ala Leu Met Gln Lys Gly Ile
1530                1535                1540                1545

CGC GTG TAT GGT GAT GAA GTT AGT CCA ACG AAG ACT CAA ACA ACA GCA    5135
Arg Val Tyr Gly Asp Glu Val Ser Pro Thr Lys Thr Gln Thr Thr Ala
                1550                1555                1560

CCT ACA AAT GCA AAC CCA ACT GCG ACG ACA GCA CCT ACA GCA TCT AGC    5183
```

-continued

```
Pro Thr Asn Ala Asn Pro Thr Ala Thr Thr Ala Pro Thr Ala Ser Ser
        1565                1570                1575

ACT CAA GGT TGG GCG ACA ACG GCG AAT ACG GCG GGT GGT GTA GCA CCA          5231
Thr Gln Gly Trp Ala Thr Thr Ala Asn Thr Ala Gly Gly Val Ala Pro
        1580                1585                1590

GCA GGT AAT GTA GCA ACG GGG GAT ATT GCG CCG ACA CAG CCA ACA TTG          5279
Ala Gly Asn Val Ala Thr Gly Asp Ile Ala Pro Thr Gln Pro Thr Leu
        1595                1600                1605

CCA GAG ATG AAT ACG GCA TTG GTT GAT GAT CAC TTG GCT GTG CCG TTA          5327
Pro Glu Met Asn Thr Ala Leu Val Asp Asp His Leu Ala Val Pro Leu
1610                1615                1620                1625

GGT GGA AGC CTC AAG ATT CAC GGA GAT CAT AAT GTG AAA ACA ACG ATT          5375
Gly Gly Ser Leu Lys Ile His Gly Asp His Asn Val Lys Thr Thr Ile
                1630                1635                1640

TCT GCG GAT AAT CAA GTG GGG ATT TCA TTA CAG CCA AAT ATT TCT ATT          5423
Ser Ala Asp Asn Gln Val Gly Ile Ser Leu Gln Pro Asn Ile Ser Ile
                1645                1650                1655

GAG AAT AAC TTG GTA ATT GGT TCA AAT GAT CCT GAG AAG GCA AAA TTA          5471
Glu Asn Asn Leu Val Ile Gly Ser Asn Asp Pro Glu Lys Ala Lys Leu
                1660                1665                1670

GCC GCA CAA GAA GGT AAT GCT TTG GTT ATC ACT AAC AAA GAT GAC GGG          5519
Ala Ala Gln Glu Gly Asn Ala Leu Val Ile Thr Asn Lys Asp Asp Gly
        1675                1680                1685

AAT GCG GCG ATG GTC TTT AAT AAC GAG AAA AAT ATG CTT GTT CTC AGT          5567
Asn Ala Ala Met Val Phe Asn Asn Glu Lys Asn Met Leu Val Leu Ser
1690                1695                1700                1705

GAT AAA GAG GCG AAA CCA AGA GTG CTT CTT GAT GGA CAA AAT GGG GCA          5615
Asp Lys Glu Ala Lys Pro Arg Val Leu Leu Asp Gly Gln Asn Gly Ala
                1710                1715                1720

TTA ACT TTA GTC GGC AAT GAT GAT TCT CAA GTC ACC CTT TCC TCT AAG          5663
Leu Thr Leu Val Gly Asn Asp Asp Ser Gln Val Thr Leu Ser Ser Lys
                1725                1730                1735

AAA GGT AAA GAT ATT GAT GGA AAT GAT TTG AGC CGT CTC TCT GTG ACG          5711
Lys Gly Lys Asp Ile Asp Gly Asn Asp Leu Ser Arg Leu Ser Val Thr
        1740                1745                1750

ACT GAA AGA ACA AAT GCT GAT GGG CAA CTT GAA AAA GTG GAA ACC TCA          5759
Thr Glu Arg Thr Asn Ala Asp Gly Gln Leu Glu Lys Val Glu Thr Ser
        1755                1760                1765

TTT GCT ACA ATG GAT GAT GGC TTG AAG TTC AAA GCC GAC GGG GAT AAA          5807
Phe Ala Thr Met Asp Asp Gly Leu Lys Phe Lys Ala Asp Gly Asp Lys
1770                1775                1780                1785

GTG ATT AAT AAG AAA CTT AAT GAA ACC GTT GAA ATT GTT GGT GAT GAG          5855
Val Ile Asn Lys Lys Leu Asn Glu Thr Val Glu Ile Val Gly Asp Glu
                1790                1795                1800

AAT GTG ACA ACA TCT ATT ACT GAT GAT AAT AAG GTG AAA GTT TCA CTG          5903
Asn Val Thr Thr Ser Ile Thr Asp Asp Asn Lys Val Lys Val Ser Leu
                1805                1810                1815

AAT AAG AAA ATC GCG ATT GAT GAG GTT AAG ATT CCA AAT ACA GAT CCT          5951
Asn Lys Lys Ile Ala Ile Asp Glu Val Lys Ile Pro Asn Thr Asp Pro
        1820                1825                1830

GAT GCT CAA AAG GGA GAT AGC ATT GTA ATC AAC AAT GGT GGA ATC CAC          5999
Asp Ala Gln Lys Gly Asp Ser Ile Val Ile Asn Asn Gly Gly Ile His
        1835                1840                1845

GCA GGT AAT AAA GTG ATT ACT GGC GTT AAA GCG AGT GAT GAC CCA ACC          6047
Ala Gly Asn Lys Val Ile Thr Gly Val Lys Ala Ser Asp Asp Pro Thr
1850                1855                1860                1865

AGT GCA GTG AAT CGA GGT CAA TTA AAT ACT GTG ATT GAT AAT GTT CAA          6095
Ser Ala Val Asn Arg Gly Gln Leu Asn Thr Val Ile Asp Asn Val Gln
                1870                1875                1880
```

-continued

| | |
|---|---|
| AAT AAT TTC AAT CAA GTT AAT CAA CGT ATT GGC GAT TTA ACA CGG GAG<br>Asn Asn Phe Asn Gln Val Asn Gln Arg Ile Gly Asp Leu Thr Arg Glu<br>                  1885                   1890                   1895 | 6143 |
| TCG CGT GCA GGT ATT GCA GGT GCA ATG GCG ACG GCA AGC CTA CAA AAT<br>Ser Arg Ala Gly Ile Ala Gly Ala Met Ala Thr Ala Ser Leu Gln Asn<br>     1900                   1905                   1910 | 6191 |
| GTT GCT TTA CCA GGG AAA ACA ACG ATT TCC GTA GGT ACA GCA ACG TTC<br>Val Ala Leu Pro Gly Lys Thr Thr Ile Ser Val Gly Thr Ala Thr Phe<br>     1915                   1920                   1925 | 6239 |
| AAA GGG GAG AAT GCT GTT GCA ATA GGG ATG TCT AGA CTC TCT GAT AAT<br>Lys Gly Glu Asn Ala Val Ala Ile Gly Met Ser Arg Leu Ser Asp Asn<br>1930                  1935                   1940                   1945 | 6287 |
| GGA AAA GTA GGT ATC CGT TTA TCT GGT ATG AGT ACG AGT AAC GGA GAT<br>Gly Lys Val Gly Ile Arg Leu Ser Gly Met Ser Thr Ser Asn Gly Asp<br>                   1950                   1955                   1960 | 6335 |
| AAA GGG GCA GCA ATG AGT GTT GGA TTT AGC TTT TAGCCTTAAT CCATAAAT<br>Lys Gly Ala Ala Met Ser Val Gly Phe Ser Phe<br>                 1965                   1970 | 6388 |
| GCAAAAAGCG AATCACCTTT GATTCGCTTT TTTTATCAGA TTATGTGCCG TAAAACTC | 6448 |
| TCCTTCAGGG CGGAGATATA AGGCACAAAC GGCGTAAGCC GTTTCAAACC TAACTAAT | 6508 |
| GGTGTTTGTT GTTGCTCAAT GTATTGGCGA ATAATGGAAA TTGGAGCGCC ACCACAAC | 6568 |
| CCTGCAAAAT AAGACGGAGA CCAAAGCTGA TTACCCCAAA GTTTTTTGCG GATGTTCG | 6628 |
| TAGTTTTTCT TCCTAATCAT TCGGCTTGAT ACACCTTTTA AACTGTTTAC AAGTGTAG | 6688 |
| ACAGCCACTT TCGGTGGATA TTCCACAAGT AAATGAACAT GATCGTCTTC ACCGTCAA | 6748 |
| TCAACTAATT TTGCTTTAAA ATCATTGCAG ACGCTTTCAA AAATCAATTT GAGTTCGT | 6808 |
| AAAATAGCTT TCGTAAAAAC ATCACGGCGA TATTTTGTTA CAAAGACTAA GTGAACAT | 6868 |
| ATATTAAAAA CACAATGTCT ACCGTGCCTA ATTTCTGTTT CTTTTTGCAT AGACCAAG | 6928 |
| TAAAATGTTG AAAACTTACA TTCTAAACCT TGTCAATGCA ACTACGCAAA GCCTTTAA | 6988 |
| TCGAGATAAT GCCGAATGGC GAACAAACCC GTAAAATCAA GCAATTTTGC GGTTGTTC | 7048 |
| GTTTTGTGTT CAATCGGGCA TTGGCTTGGC AAAATGAACA ATACGGGCAA GATAACAG | 7108 |
| TTAAGTTCAG TTACACTAAA ATCGCCAACT TGCTTCCACA ATGGAAAAAA GAATTAGT | 7168 |
| GGCTAAAAGA ATGCCATTCT CAAGTGCTTC AACAGTCGCT AAAAGATCTT GAGAGTGC | 7228 |
| TCAAAAATTT CTTTCAGAAA CGTGCCGACT TTCCAAAATT CAAGAAAAAA GGCGTGAA | 7288 |
| AGAGCTTTCG TTTTCCGCAA GGTTGCAAAT TAGAACAGGA AAATGACCGC TTATTTTT | 7348 |
| CAAAAATCGG CTGGATTCGC TATCGCAACA GCCGAGATAT CGTTGGTGAA ATCAAAAA | 7408 |
| TTACCGTCAG CCAAAAGTGC GGTCACTATT TTGTCAGTAT TCAAACTGAA TTTGAGTA | 7468 |
| AAATCCCGAC ACATAAAGGC GGTGAAATCG GTATTGATAT GGGCGTTGCA CGTTTTGC | 7528 |
| CATTGTCAAA TGGTGAATAT TTTGAACCGG TTAACGCCTT TAAAACTTAC AAAGGAAA | 7588 |
| TGGCTAAACT GCAAAGAGG CTTAAAAATA AAGTAAAATT TAGCCAAAAT TGGCAGAA | 7648 |
| TAAAGGCGAA AATCGCCAAA CTGCATCATA AAATTGCTAA TTGTCGCAAA GACTTCTT | 7708 |
| ATCAGACTTC AAGCAAAATC AGCAAAAACC ACGCCATGAT CTATATTGAA GATTTGCA | 7768 |
| TGTCAAATAT GTCAAAATCA GCCAAAGGTA CGGCGGAAAC ACCAGGCAAA AATGTTGC | 7828 |
| CAAAATCAGG GTTGAACCAA GCGATATTAG ATCAATCTTG GTTTGAGTTT CGCCGTCA | 7888 |
| TGGACTACAA AACGCAATGG CAAGGTGGAT TTTTAGTGGC AGTGCCAGCG CAAAATAC | 7948 |
| GTCGAACTTG CCCTTGTTGT GGTCATGTAG CAAAAGAAAA TCGCCAAACA CAGGCTAA | 8008 |
| TTGAGTGTGT AGAATGTGGC TACACAGAAA ATGCCGATGT GGTTGGAGCG TTAAATGT | 8068 |

```
TGGGGCGTGG GCGAGCTATC GTCCACGCGT AATAAAATGT CAGGGCAGGA CATGCCCG      8128

GAGCTTGTGA AGTGAACTTC ATTGAGAGGT CAGCAACAAG AACCCACCGA GAGTAGCC      8188

TTGCTTGCCA ATTGGCACTA GTAGGAATCC CCATCCTTTA GGGCGGGGAG GATGTCAA      8248

ACATCATTAA TATTTAATGA AAAATATTAT AACTAATTGA TTTTTATATT ATTATTTG      8308

TATTTGGGCG GTGGGACATA ATTTTGACAG ACAGAATGAT ATCGTTTATA TTTCCGAA      8368

TCTGAT ATG TTA TTT AGT AAA ATA TCA GAT AAG AAA AAT TTA TTT TTC       8416
       Met Leu Phe Ser Lys Ile Ser Asp Lys Lys Asn Leu Phe Phe
       1               5                   10

TTT ATA TAT AGC TCA ATT AAA AGG AAA TTT ATT ATG AAA AAG ACA CTT      8464
Phe Ile Tyr Ser Ser Ile Lys Arg Lys Phe Ile Met Lys Lys Thr Leu
15                  20                  25                  30

ATC GCT TTA GCT GTA ATA ACA ATG TTT TCA AGT GCA GCA AAT GCT GCG      8512
Ile Ala Leu Ala Val Ile Thr Met Phe Ser Ser Ala Ala Asn Ala Ala
                35                  40                  45

GTC ATT TAT GAA AAA GAA GGT ACG AAA ATT GAT ATT GAT GGT CGT ATG      8560
Val Ile Tyr Glu Lys Glu Gly Thr Lys Ile Asp Ile Asp Gly Arg Met
            50                  55                  60

CAT TTT GAA TTA CGT AAT GAT TCA GGC AAA CGT TCT GAT TTA CAA GAT      8608
His Phe Glu Leu Arg Asn Asp Ser Gly Lys Arg Ser Asp Leu Gln Asp
                65                  70                  75

GCA GGC TCT CGT GTC CGC GTA AGA GCT TTT CAA GAA ATT GGC AAT GGC      8656
Ala Gly Ser Arg Val Arg Val Arg Ala Phe Gln Glu Ile Gly Asn Gly
80                  85                  90

TTT TCT ACC TAT GGG GCT GTT GAG TTT CGT TTT TCT ACT AAG AAA GAT      8704
Phe Ser Thr Tyr Gly Ala Val Glu Phe Arg Phe Ser Thr Lys Lys Asp
95                  100                 105                 110

GGC TCA GAA CAA AGT ATT GGA TCT GAC TTA AGA GCT CAC CGC TTT TTT      8752
Gly Ser Glu Gln Ser Ile Gly Ser Asp Leu Arg Ala His Arg Phe Phe
                115                 120                 125

GCA GGA ATT AAA CAA AAA GAC ATA GGG GAA TTA ACT TTC GGT AAA CAA      8800
Ala Gly Ile Lys Gln Lys Asp Ile Gly Glu Leu Thr Phe Gly Lys Gln
                130                 135                 140

CTC CAT TTA GGT GAT CTT GTC CCG AAA GCA AAT TAT TCT TAT GAT TTA      8848
Leu His Leu Gly Asp Leu Val Pro Lys Ala Asn Tyr Ser Tyr Asp Leu
            145                 150                 155

GGG GCG AAC TCT TTT TTT GGT GCA CAT AGT AAA GTA GCA CAT TTT ATT      8896
Gly Ala Asn Ser Phe Phe Gly Ala His Ser Lys Val Ala His Phe Ile
160                 165                 170

TCT GTA CCA TTT AAT GGT GTG AGG GTG TCT GCA G                        8930
Ser Val Pro Phe Asn Gly Val Arg Val Ser Ala
175             180                 185

(2) INFORMATION FOR SEQ ID NO: 2:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (vi) ORIGINAL SOURCE:

(xi) SEQUENCE DESCRIPTION: SEQ ID NO: 2:

Lys Trp Leu Glu Val Tyr Ser Ser Ser Val Lys Leu Ser
1               5                   10
```

(2) INFORMATION FOR SEQ ID NO: 3:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 3:

```
CGCGGATCCA TGAATAAAGT TTTTAAAATT AAATATTCTG TTG          43
```

(2) INFORMATION FOR SEQ ID NO: 4:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 4:

```
CGCGGATCCT TAAGGCTAAA AGCTAAATCC AACACTCAT              39
```

(2) INFORMATION FOR SEQ ID NO: 5:

(i) SEQUENCE CHARACTERISTICS:
        (A) LENGTH: 7486 base pairs
        (B) TYPE: nucleic acid
        (C) STRANDEDNESS: double
        (D) TOPOLOGY: linear (ii) MOLECULE TYPE: genomic DNA (vi) ORIGINAL SOURCE:

(ix) FEATURE:
        (A) NAME/KEY: CDS
        (B) LOCATION: 848..6964

(xi) SEQUENCE DESCRIPTION: SEQ ID NO: 5:

```
TCTAGAATAT AAATCTTCAG TATCAACATA CAAGGGGCGT ATCGCATACG CCCCTGTGCT    60
GAATTTTTAC TTACAGAACA CCGTACTTTT GTTCTGTCAT TTTTGGATAT TTGGGCTGAT   120
GGCTTTTTTC TTTGGTAGTT ATAACGGGTT TCGCTCGTTG AGCGACTTAC TTTCTTTTAC   180
ATTCCCAAAA GAAAGTAAGC AAAGAAAAGG GAACCCGACT AAATTGCTGT TCCTCATTCC   240
AATAAAATTT TCTTCATGAA AAGTAAGCCT GATGTTCGCT TCGCTCTCGC TCGGCGTTAC   300
TTTTCTTAAA ATTTTATTTC CATTCGGGCA ATTTACACGG GAAAGGGCGA TTTTTAAAAG   360
TGCGGTGGTT TTTGAAGGAT ATTTTTGTAT TTGGAAAAAT CAAGAAAATG GCTTTAGAAA   420
ACACCTCACT TATTTTAACT GTAGGTATTG CATTTTTAAT AATACAAATT TTTCTTGAAA   480
TGATGAAATA ACCAATCAAA TTAGTCAGTT ATAAGTGGAG AAACTTAAAG AAAATGATTA   540
AATTAGGCTC ACTCATTAGA CCAGTAAGGG AATTAAAATA GTATTTTAA TTGCATTTAG    600
TTATTAAGTG TTAGAAATTA CCTATTGCAT CAATAAATGA GGTGTTTTTA TTTGTAATCT   660
CTAATTAATT AGAGTAGTAT TAAGTGGAGT TTTATCTTTA CTAAATTAAT GGTATCACCT   720
CTCAGAGAGG GAGAAGCAAA TTCCCCCCCC CTAGAAATAC CTAATAAGAG TTACATTAAG   780
GGCATATTAT AAAAGTAATT TATCAATAAT GATTAACGCT CATTATTATT AACAAAGGCA   840
AATGATT ATG AAT AAA GTT TTT AAA ATT AAA TAT TCT GTT GTA AAA CAA     889
        Met Asn Lys Val Phe Lys Ile Lys Tyr Ser Val Val Lys Gln
```

```
              -70                 -65                 -60
GAA ATG ATT GTG GTT TCA GAG CTA GCA AAT AAT AAA GAT AAA ACA GCT    937
Glu Met Ile Val Val Ser Glu Leu Ala Asn Asn Lys Asp Lys Thr Ala
        -55                 -50                 -45

AGC CAA AAA AAC ACA CAT AAT ACT GCC TTT TTT CAA CCG CTA TTT ACA    985
Ser Gln Lys Asn Thr His Asn Thr Ala Phe Phe Gln Pro Leu Phe Thr
-40                 -35                 -30                 -25

AAG TGT ACA TAT CTT GCT CTT CTC ATT AAT ATC GCA CTA GGA ACA TCA   1033
Lys Cys Thr Tyr Leu Ala Leu Leu Ile Asn Ile Ala Leu Gly Thr Ser
                -20                 -15                 -10

TTA TTC CCT CAA TTA GCT AAT GCG AAA TTT TTA GAG GTT TAT AAT AGC   1081
Leu Phe Pro Gln Leu Ala Asn Ala Lys Phe Leu Glu Val Tyr Asn Ser
            -5                  1                   5

TCC GTA AAA CTA CAG CAT GTT AAT AGT GGC GTA CCA AGT GAT AGT GTT   1129
Ser Val Lys Leu Gln His Val Asn Ser Gly Val Pro Ser Asp Ser Val
        10                  15                  20

AAT CTT AAT CCA TCG GGA GGT GAG AAT GTT GGC ATG AAT AGC AAT CAA   1177
Asn Leu Asn Pro Ser Gly Gly Glu Asn Val Gly Met Asn Ser Asn Gln
25                  30                  35                  40

GGG GTC GCT ATT GGC CGT GGT GCA GTA AAT AAT TAT TCG GCG ACG GGA   1225
Gly Val Ala Ile Gly Arg Gly Ala Val Asn Asn Tyr Ser Ala Thr Gly
            45                  50                  55

TCA ATT GCT ATT GGT CAG GGG GCA AAA AAT GAT AAT TGG GCG ACG AGA   1273
Ser Ile Ala Ile Gly Gln Gly Ala Lys Asn Asp Asn Trp Ala Thr Arg
        60                  65                  70

TCA ATT GCT ATT GGT CAG GGG GCA AAA AAT GAA AGT ATA GCA TCA GAT   1321
Ser Ile Ala Ile Gly Gln Gly Ala Lys Asn Glu Ser Ile Ala Ser Asp
    75                  80                  85

TCT GTG GCT ATT TCC AAC GCG ATT AAC CGT TTT AAA AAA TCT ATT GTG   1369
Ser Val Ala Ile Ser Asn Ala Ile Asn Arg Phe Lys Lys Ser Ile Val
90                  95                  100

ATA GGT CTT AAT ACT TAT ACA CAA TTA GAT CCC CGT AGA GCT CCA GAA   1417
Ile Gly Leu Asn Thr Tyr Thr Gln Leu Asp Pro Arg Arg Ala Pro Glu
105                 110                 115                 120

TCC CGT CAA GGT TCT GTG GTG ATT GGG GAA AAT GCG AAA AGT GCT GGG   1465
Ser Arg Gln Gly Ser Val Val Ile Gly Glu Asn Ala Lys Ser Ala Gly
            125                 130                 135

AAT CAA TCT GTT TCT TTA GGG CAA AAT GCG TGG TCA AAA ACC AAT TCT   1513
Asn Gln Ser Val Ser Leu Gly Gln Asn Ala Trp Ser Lys Thr Asn Ser
        140                 145                 150

ATT TCT ATT GGG GCA GGA ACC TTT GCG GAA GGG AAA TCA ACC ATT GCT   1561
Ile Ser Ile Gly Ala Gly Thr Phe Ala Glu Gly Lys Ser Thr Ile Ala
    155                 160                 165

ATA GGG ACT GAT AAA ATA CTA GGG ACT AAT TAT AAT GAC AAA TTG CCT   1609
Ile Gly Thr Asp Lys Ile Leu Gly Thr Asn Tyr Asn Asp Lys Leu Pro
170                 175                 180

GCT CCT AGT TGG GAT GGA AGA ACA GGT AAG GCA CCT ACT AAT TCC ATT   1657
Ala Pro Ser Trp Asp Gly Arg Thr Gly Lys Ala Pro Thr Asn Ser Ile
185                 190                 195                 200

TGG GAT ATA TTT TCT GAG TTA TAT ATG GGG AAA AAG ACT AAC GGC ACA   1705
Trp Asp Ile Phe Ser Glu Leu Tyr Met Gly Lys Lys Thr Asn Gly Thr
            205                 210                 215

GAT TAT GAT GCA AAA AAA AAT GAC CGC GAT CCA AAT AAG CCA GAG GCT   1753
Asp Tyr Asp Ala Lys Lys Asn Asp Arg Asp Pro Asn Lys Pro Glu Ala
        220                 225                 230

TTT TAT ACC TAT TCT GAT TTT AAA AGC AGA TAT GTT AAT AAC CCA AGT   1801
Phe Tyr Thr Tyr Ser Asp Phe Lys Ser Arg Tyr Val Asn Asn Pro Ser
    235                 240                 245

ACC TCT CCC ACT TAT GCC GCT AAA TTA GGG GCA ATT GCC CTA GGT TCC   1849
```

```
Thr Ser Pro Thr Tyr Ala Ala Lys Leu Gly Ala Ile Ala Leu Gly Ser
    250                 255                 260

CGC ACC ATT GCT GCG GGG GAA ATG TCC ACT GCG GTC GGT TCC TTA GCC      1897
Arg Thr Ile Ala Ala Gly Glu Met Ser Thr Ala Val Gly Ser Leu Ala
265                 270                 275                 280

TTT GCA TTG GCA GAT AAA TCC ACC GCA ATG GGG TTA CGT TCT TTT GTT      1945
Phe Ala Leu Ala Asp Lys Ser Thr Ala Met Gly Leu Arg Ser Phe Val
                    285                 290                 295

GCT AAA GAT GCC GTA GGT GGA ACG GCA ATC GGG GAA GAA TCG CGA ACC      1993
Ala Lys Asp Ala Val Gly Gly Thr Ala Ile Gly Glu Glu Ser Arg Thr
                300                 305                 310

TTT GCT AAA GAT TCC GTT GCC ATT GGT AAT AAA ACT GAA GCC TCA AAT      2041
Phe Ala Lys Asp Ser Val Ala Ile Gly Asn Lys Thr Glu Ala Ser Asn
            315                 320                 325

GCT GGC TCA ATG GCT TAT GGT TAT AAG GCG AAA GCG GTA GGT GCG GGG      2089
Ala Gly Ser Met Ala Tyr Gly Tyr Lys Ala Lys Ala Val Gly Ala Gly
330                 335                 340

GCA ATC GCA ATT GGT GCA GAA GTC GCA GCA GGG GCT GAA TTT GAT AGC      2137
Ala Ile Ala Ile Gly Ala Glu Val Ala Ala Gly Ala Glu Phe Asp Ser
345                 350                 355                 360

AGT CAA GCA GGA AAT TTA TTA CTA AAT AGA GGT GCT TAT GCT ACT TTA      2185
Ser Gln Ala Gly Asn Leu Leu Leu Asn Arg Gly Ala Tyr Ala Thr Leu
                365                 370                 375

AAA AGT GCC GAT AAA TCA GAT GAT ATT AAA GCT GGA GAT GCG ATT AAC      2233
Lys Ser Ala Asp Lys Ser Asp Asp Ile Lys Ala Gly Asp Ala Ile Asn
                380                 385                 390

GTA TTT ACC CAG TTT TTT GAT AAT ATG CTT ACT CAA GGC TCA CAC CTG      2281
Val Phe Thr Gln Phe Phe Asp Asn Met Leu Thr Gln Gly Ser His Leu
            395                 400                 405

ACA TAT GAA AAT ACC ACC TAT TTA ACC ACT TCA GCA GGT GAT ATC AAG      2329
Thr Tyr Glu Asn Thr Thr Tyr Leu Thr Thr Ser Ala Gly Asp Ile Lys
410                 415                 420

AAA ACA TTA GCT GCA GTT GGA GAT GGC GGG AAA AAT GCC ATT GCC ATT      2377
Lys Thr Leu Ala Ala Val Gly Asp Gly Gly Lys Asn Ala Ile Ala Ile
425                 430                 435                 440

GGT AAT AAA ACC TTT GCA TCT AAA GCA AAT TCT GTG GCA TTA GGG AGC      2425
Gly Asn Lys Thr Phe Ala Ser Lys Ala Asn Ser Val Ala Leu Gly Ser
                445                 450                 455

TAT GCC TTA GCG AGT GCC CAA AAT GCC TTT GCA CTA GGT TCT TAT TCT      2473
Tyr Ala Leu Ala Ser Ala Gln Asn Ala Phe Ala Leu Gly Ser Tyr Ser
                460                 465                 470

TTA GTG TCC CCT TTA GCA GCC AAT ACA ATC GTA ATT GGT GTG GGA GGT      2521
Leu Val Ser Pro Leu Ala Ala Asn Thr Ile Val Ile Gly Val Gly Gly
            475                 480                 485

TAT GCC ACA GGA TCA AAC AGT TTC GTA GGG GGT TCT TGG GTA TCA ACC      2569
Tyr Ala Thr Gly Ser Asn Ser Phe Val Gly Gly Ser Trp Val Ser Thr
490                 495                 500

CTT TCA GCT CGG ACA GTT GTG CTA GGG TAT TCC GCT TCA ATT AGC TCA      2617
Leu Ser Ala Arg Thr Val Val Leu Gly Tyr Ser Ala Ser Ile Ser Ser
505                 510                 515                 520

GAT TCT CAT GAT TCA TTA GCA ATG GGG GTG AAT GCC TTT ATT GGT AAT      2665
Asp Ser His Asp Ser Leu Ala Met Gly Val Asn Ala Phe Ile Gly Asn
                525                 530                 535

GGT AGT AAT TCT TCA TTG GCA TTA GGT ACG GGA TCT ACT ATT GCG AAA      2713
Gly Ser Asn Ser Ser Leu Ala Leu Gly Thr Gly Ser Thr Ile Ala Lys
                540                 545                 550

AAT GCC AAA TCT CCT GAC AGC TTA GCC ATT GGT AAA GAC TCA CGA ATT      2761
Asn Ala Lys Ser Pro Asp Ser Leu Ala Ile Gly Lys Asp Ser Arg Ile
                555                 560                 565
```

-continued

```
GAC GCT AAA GAT ACA GAT AAT GGT GTT TTG TAT ACC CCT CAA GTT TAT        2809
Asp Ala Lys Asp Thr Asp Asn Gly Val Leu Tyr Thr Pro Gln Val Tyr
570                 575                 580

GAT GAA ACT ACT CGA GCC TTT AGA ACC TTT GAT GAA AAC AAA GAT TAT        2857
Asp Glu Thr Thr Arg Ala Phe Arg Thr Phe Asp Glu Asn Lys Asp Tyr
585                 590                 595                 600

ATG CGT CAA GCA ATG GCA TTA GGT TTT AAT GCG AAG GTT TCG CGT GGG        2905
Met Arg Gln Ala Met Ala Leu Gly Phe Asn Ala Lys Val Ser Arg Gly
                605                 610                 615

AAG GGC AAA ATG GAA ACG GGG ATT AAC TCG ATG GCG ATT GGT GCT CGT        2953
Lys Gly Lys Met Glu Thr Gly Ile Asn Ser Met Ala Ile Gly Ala Arg
            620                 625                 630

TCT CAA GCA ACT TTG CAA AAT TCC ACC GCA CTT GGG GTA AAC GCT AAA        3001
Ser Gln Ala Thr Leu Gln Asn Ser Thr Ala Leu Gly Val Asn Ala Lys
        635                 640                 645

ACA GAT TAC ACT TGG GAA CAG TTA GAA GCC GAT CCT TGG GTA TCT AAA        3049
Thr Asp Tyr Thr Trp Glu Gln Leu Glu Ala Asp Pro Trp Val Ser Lys
    650                 655                 660

GGG GCA ATC AGT ATC CCA ACT TCA GGC AAA ATT GGG GTT ATC TCT GTG        3097
Gly Ala Ile Ser Ile Pro Thr Ser Gly Lys Ile Gly Val Ile Ser Val
665                 670                 675                 680

GGC TCA AAA GGC TCA GAA CGT CGT ATT GTG AAT GTT GCT TCG GGT TCT        3145
Gly Ser Lys Gly Ser Glu Arg Arg Ile Val Asn Val Ala Ser Gly Ser
                685                 690                 695

CTT GAT ACC GAT GCC GTG AAT GTT GCC CAA TTA AAA ACT ATT GAA GAA        3193
Leu Asp Thr Asp Ala Val Asn Val Ala Gln Leu Lys Thr Ile Glu Glu
            700                 705                 710

CGT TTC CAA TCT GAA ATT GAT TTA TTA CAA AAT GGC GGT GGG GTG CAA        3241
Arg Phe Gln Ser Glu Ile Asp Leu Leu Gln Asn Gly Gly Gly Val Gln
        715                 720                 725

TAT CTC TCT GTT GAA AAA ACG AAT ATC AAT GGA GAA GCG GGG AGA GTG        3289
Tyr Leu Ser Val Glu Lys Thr Asn Ile Asn Gly Glu Ala Gly Arg Val
    730                 735                 740

GCT AGC CAA ATT CGT AAA GGG GAA AGT TAT AAG CGA TAT GTG AAA TTA        3337
Ala Ser Gln Ile Arg Lys Gly Glu Ser Tyr Lys Arg Tyr Val Lys Leu
745                 750                 755                 760

AAA ACA CAA TTG CTC TAT TTA GAT GCA CGA AAA AAA TTA AAT GGA GAG        3385
Lys Thr Gln Leu Leu Tyr Leu Asp Ala Arg Lys Lys Leu Asn Gly Glu
                765                 770                 775

AAG TTT GAT CAA ACT TCA TTA GAC AAA ATT AGT AAG GCA GTG CAA GAA        3433
Lys Phe Asp Gln Thr Ser Leu Asp Lys Ile Ser Lys Ala Val Gln Glu
            780                 785                 790

CTT GAA GCG GAA TAT AGT GGC GAG TTA AAA ACA ACT GCG TCA GAA CTT        3481
Leu Glu Ala Glu Tyr Ser Gly Glu Leu Lys Thr Thr Ala Ser Glu Leu
        795                 800                 805

AAT AGA GTT GCA ATG CAA TTG AAT GCT GAG ACA ACT GTA AAT GAC TTC        3529
Asn Arg Val Ala Met Gln Leu Asn Ala Glu Thr Thr Val Asn Asp Phe
    810                 815                 820

GGG AAA TTT AAT CAA TAT AAA ACG CAG ATT GAG AAT GCA ACC AAT GCG        3577
Gly Lys Phe Asn Gln Tyr Lys Thr Gln Ile Glu Asn Ala Thr Asn Ala
825                 830                 835                 840

GAT TCA GAA AAA AAT GTA GGC GGC TTA TCC CCT CAA GTA ATT GCA CAG        3625
Asp Ser Glu Lys Asn Val Gly Gly Leu Ser Pro Gln Val Ile Ala Gln
                845                 850                 855

TTA AAA GCC AAT AAT AAC TAT CTT AAT GAT GGT GCA AAA GGG CAA GAC        3673
Leu Lys Ala Asn Asn Asn Tyr Leu Asn Asp Gly Ala Lys Gly Gln Asp
            860                 865                 870

AGT ATA GCA TTT GGC TGG CAG GCA AAA ACC TCA GAA GCT AAT AAT GGA        3721
Ser Ile Ala Phe Gly Trp Gln Ala Lys Thr Ser Glu Ala Asn Asn Gly
        875                 880                 885
```

```
TTA GCA GGG AAA CAA GCC ATT GCG ATT GGT TTC CAA GCG AAT TCT TCC    3769
Leu Ala Gly Lys Gln Ala Ile Ala Ile Gly Phe Gln Ala Asn Ser Ser
        890             895                 900

GCT GAA AAT GCC ATT TCT ATC GGT ACG AAT TCG GAT ACC TCA ATG ACA    3817
Ala Glu Asn Ala Ile Ser Ile Gly Thr Asn Ser Asp Thr Ser Met Thr
905             910                 915                 920

GGG GCA GTG GCG ATT GGT AAA GGT GCA ACG GTT ACT GCG GGT GGA AAA    3865
Gly Ala Val Ala Ile Gly Lys Gly Ala Thr Val Thr Ala Gly Gly Lys
                925                 930                 935

CCT TCC ATT GCA TTG GGG CAA GAT TCG ACG GTT GCC AAT TCC GCA ATT    3913
Pro Ser Ile Ala Leu Gly Gln Asp Ser Thr Val Ala Asn Ser Ala Ile
            940                 945                 950

AGC CGT ACA AGT TCA GTG ATG ATA AAT GGT TTA ACA TTC AAT AAT TTT    3961
Ser Arg Thr Ser Ser Val Met Ile Asn Gly Leu Thr Phe Asn Asn Phe
        955                 960                 965

GCA GGT TCC CCT GAA ACA CTC GGT GTG TTA AGT ATC GGA ACG GCT GGG    4009
Ala Gly Ser Pro Glu Thr Leu Gly Val Leu Ser Ile Gly Thr Ala Gly
970             975                 980

AAA GAG CGT AAA ATT GTT AAT GTT GCA GCA GGC GAT ATT TCG CAA ACT    4057
Lys Glu Arg Lys Ile Val Asn Val Ala Ala Gly Asp Ile Ser Gln Thr
985             990                 995                 1000

TCT ACT GAA GCC ATT AAC GGC TCA CAG CTT TAT GCA ACG AAC TTT ATG    4105
Ser Thr Glu Ala Ile Asn Gly Ser Gln Leu Tyr Ala Thr Asn Phe Met
            1005                1010                1015

TTG AAC AAA CTG GCT CAA TCC GTT AAA ACG AAT TTT GGC GGT AAT GCA    4153
Leu Asn Lys Leu Ala Gln Ser Val Lys Thr Asn Phe Gly Gly Asn Ala
        1020                1025                1030

AAC CTT GCC ACT GAT GGC ACA ATT ACA TTT ACA AAT ATT GGC GGC ACA    4201
Asn Leu Ala Thr Asp Gly Thr Ile Thr Phe Thr Asn Ile Gly Gly Thr
            1035                1040                1045

GGG CAA GAT ACA ATC CAC GAT GCG ATT AAT AAT GTT CTC ACC AAA TTG    4249
Gly Gln Asp Thr Ile His Asp Ala Ile Asn Asn Val Leu Thr Lys Leu
        1050                1055                1060

ATC TCG CTT TCG GCA ACA GAA GAA GAA GAA GTG GTG TCA GGG GAA GCT    4297
Ile Ser Leu Ser Ala Thr Glu Glu Glu Glu Val Val Ser Gly Glu Ala
1065                1070                1075                1080

GTC TAT GAT GCA CTT AAA GGT GCA AAA CCA ACG GTT TCA GCA GAA GCC    4345
Val Tyr Asp Ala Leu Lys Gly Ala Lys Pro Thr Val Ser Ala Glu Ala
            1085                1090                1095

AAC AAA GGC ATT ACT GGC TTG GTG GAT GTG GTG AAA AAA GCA AAT TCA    4393
Asn Lys Gly Ile Thr Gly Leu Val Asp Val Val Lys Lys Ala Asn Ser
        1100                1105                1110

CCG ATC ACA GTT GAG CCT TCT ACC GAT AAC AAC AAG AAA AAA ACC TTC    4441
Pro Ile Thr Val Glu Pro Ser Thr Asp Asn Asn Lys Lys Lys Thr Phe
            1115                1120                1125

ACT GTC GGC TTA ATG AAA GAC ATT GAA GGG GTA AAC AGC ATT ACC TTT    4489
Thr Val Gly Leu Met Lys Asp Ile Glu Gly Val Asn Ser Ile Thr Phe
        1130                1135                1140

GAT AAG TCA GGG CAA GAT CTA AAT CAA GTT ACG GGC AGA ATG AGC AGT    4537
Asp Lys Ser Gly Gln Asp Leu Asn Gln Val Thr Gly Arg Met Ser Ser
1145                1150                1155                1160

GCG GGT TTA ACC TTC AAA AAA GGC GAC ACA ACA AAT GGT TCA ACC ACC    4585
Ala Gly Leu Thr Phe Lys Lys Gly Asp Thr Thr Asn Gly Ser Thr Thr
            1165                1170                1175

ACT TTT GCA GAA GAT GGC TTA ACC ATT GAT AGC ACA ACA AAT TCT GCT    4633
Thr Phe Ala Glu Asp Gly Leu Thr Ile Asp Ser Thr Thr Asn Ser Ala
        1180                1185                1190

CAA ACA AAC TTA GTG AAA GTA AGT CGT GAT GGC TTC TCG GTG AAA AAT    4681
Gln Thr Asn Leu Val Lys Val Ser Arg Asp Gly Phe Ser Val Lys Asn
```

-continued

```
         1195                1200                1205
GGC AGC GAT GAA AGC AAA TTA GCC TCG ACA AAA TTA TCT ATC GGT GCG      4729
Gly Ser Asp Glu Ser Lys Leu Ala Ser Thr Lys Leu Ser Ile Gly Ala
1210                1215                1220

GAA AAT GCA GAA CAC GTT GAA GTA ACT AAA TCG GGC ATA GCC TTA AAA      4777
Glu Asn Ala Glu His Val Glu Val Thr Lys Ser Gly Ile Ala Leu Lys
1225                1230                1235                1240

GCG GAT AAC ACC TCC GAT AAA TCT AGC ATC ACC TTA GCC CAA GAT GCG      4825
Ala Asp Asn Thr Ser Asp Lys Ser Ser Ile Thr Leu Ala Gln Asp Ala
                1245                1250                1255

ATT ACT CTT GCG GGG AAC GCA ACC GGA ACG GCG ATT AAA TTG ACT GGT      4873
Ile Thr Leu Ala Gly Asn Ala Thr Gly Thr Ala Ile Lys Leu Thr Gly
                1260                1265                1270

GTT GCA GAT GGC AAC ATT ACG GTA AAT TCA AAA GAT GCG GTA AAT GGG      4921
Val Ala Asp Gly Asn Ile Thr Val Asn Ser Lys Asp Ala Val Asn Gly
                1275                1280                1285

GGG CAG TTG CGT ACC TTA TTA GGG GTT GAT AGC GGG GCT AAA ATT GGC      4969
Gly Gln Leu Arg Thr Leu Leu Gly Val Asp Ser Gly Ala Lys Ile Gly
                1290                1295                1300

GGT ACT GAG AAA ACA ACG ATC AGT GAA GCC ATT TCT GAT GTG AAG CAA      5017
Gly Thr Glu Lys Thr Thr Ile Ser Glu Ala Ile Ser Asp Val Lys Gln
1305                1310                1315                1320

GCT CTT ACC GAT GCG ACA TTG GCA TAT AAA GCG GAC AAT AAA AAC GGT      5065
Ala Leu Thr Asp Ala Thr Leu Ala Tyr Lys Ala Asp Asn Lys Asn Gly
                1325                1330                1335

AAA ACA GTT AAA TTG ACT GAC GGA TTG AAT TTT ACT AGC ACG ACC AAT      5113
Lys Thr Val Lys Leu Thr Asp Gly Leu Asn Phe Thr Ser Thr Thr Asn
                1340                1345                1350

ATT GAT GCT TCA GTG GAA GAT AAC GGT GTG GTG AAA TTC ACC TTA AAA      5161
Ile Asp Ala Ser Val Glu Asp Asn Gly Val Val Lys Phe Thr Leu Lys
                1355                1360                1365

GAT AAA TTA ACA GGC TTA AAA ACT ATC GCA ACT GAA TCT TTG AAT GCT      5209
Asp Lys Leu Thr Gly Leu Lys Thr Ile Ala Thr Glu Ser Leu Asn Ala
                1370                1375                1380

TCT CAA AAT ATC ATC GCT GGC GGT ACG GTA ACA GTG GGC GGC GAG ACA      5257
Ser Gln Asn Ile Ile Ala Gly Gly Thr Val Thr Val Gly Gly Glu Thr
1385                1390                1395                1400

GAG GGC ATT GTG CTA ACA AAA TCT GGC TCA GGA AAT GAC CGC ACT TTA      5305
Glu Gly Ile Val Leu Thr Lys Ser Gly Ser Gly Asn Asp Arg Thr Leu
                1405                1410                1415

TCT TTA TCT GGT GCA GGC AAT GCA GCA ACA GAT GGC ATT AAA GTC TCT      5353
Ser Leu Ser Gly Ala Gly Asn Ala Ala Thr Asp Gly Ile Lys Val Ser
                1420                1425                1430

GGC GTG AAA GCA GGG ACG GCA GAC ACC GAT GCG GTG AAT AAA GGT CAG      5401
Gly Val Lys Ala Gly Thr Ala Asp Thr Asp Ala Val Asn Lys Gly Gln
                1435                1440                1445

TTA GAT AAA CTT TTT AAA GCG ATC AAT GAC GCA TTA GGC ACA ACA GAT      5449
Leu Asp Lys Leu Phe Lys Ala Ile Asn Asp Ala Leu Gly Thr Thr Asp
                1450                1455                1460

TTA GCG GTA ACC AAA AAT CCA AAT CAA ACC TCT ATC TTT AAT CCG ATA      5497
Leu Ala Val Thr Lys Asn Pro Asn Gln Thr Ser Ile Phe Asn Pro Ile
1465                1470                1475                1480

AAC GGC ACG GCT CCA ACC ACC TTT AAA GAC GCG GTG GAT AAA TTA ACC      5545
Asn Gly Thr Ala Pro Thr Thr Phe Lys Asp Ala Val Asp Lys Leu Thr
                1485                1490                1495

ACC GCT GTG AAT ACA GGT TGG GGA TCA AAG GTA GGT ATT TTG GCA ACA      5593
Thr Ala Val Asn Thr Gly Trp Gly Ser Lys Val Gly Ile Leu Ala Thr
                1500                1505                1510

GGT ATT GAT GGT ATT GAT GCT GGG AAT AAG AAA ATT AGT AAT GTC GCC      5641
```

```
Gly Ile Asp Gly Ile Asp Ala Gly Asn Lys Lys Ile Ser Asn Val Ala
        1515                1520                1525

GAT GGG GAT ATT TCT CCA ACC AGT GGT GAT GTA GTG ACA GGT CGT CAG    5689
Asp Gly Asp Ile Ser Pro Thr Ser Gly Asp Val Val Thr Gly Arg Gln
    1530                1535                1540

CTC TAC GCC TTA ATG CAG AAA GGT ATT CGC GTG TAT GGT GAT GAA GTT    5737
Leu Tyr Ala Leu Met Gln Lys Gly Ile Arg Val Tyr Gly Asp Glu Val
1545                1550                1555                1560

AGT CCA ACG AAG ACT CAA ACA ACA GCA CCT ACA GCA TCT AGC ACT CAA    5785
Ser Pro Thr Lys Thr Gln Thr Thr Ala Pro Thr Ala Ser Ser Thr Gln
                1565                1570                1575

GGT GGG GCG ACA ACG GCG AAT ACG GCG GGT GGT GTA GCA CCA GCA GGT    5833
Gly Gly Ala Thr Thr Ala Asn Thr Ala Gly Gly Val Ala Pro Ala Gly
            1580                1585                1590

AAT GTA GCA ACG GGG GAT ATT GCG CCG ACA CAG CCA GCA TTG CCA GAG    5881
Asn Val Ala Thr Gly Asp Ile Ala Pro Thr Gln Pro Ala Leu Pro Glu
        1595                1600                1605

ATG AAA ACG GCA TTG GTT GGT GAT CAC TTG GCT GTG CCG TTA GGT GGA    5929
Met Lys Thr Ala Leu Val Gly Asp His Leu Ala Val Pro Leu Gly Gly
    1610                1615                1620

AGC CTC AAG ATT CAC GGA GAT CAT AAT GTG AAA ACA ACG ATT TCT GCG    5977
Ser Leu Lys Ile His Gly Asp His Asn Val Lys Thr Thr Ile Ser Ala
1625                1630                1635                1640

GGT AAT CAA GTG GGG ATT TCA TTA CAG CCA AAT ATT TCT ATT GAG AAT    6025
Gly Asn Gln Val Gly Ile Ser Leu Gln Pro Asn Ile Ser Ile Glu Asn
                1645                1650                1655

AAC TTG GTA ATT GGT TCA AAT AAG CCT GAG AAG GCA AAA TTA GCC GCA    6073
Asn Leu Val Ile Gly Ser Asn Lys Pro Glu Lys Ala Lys Leu Ala Ala
            1660                1665                1670

CAA GAA GGT AAT GCT TTG GTT ATC ACT AAC AAA GAT GAC GGG AAT GCG    6121
Gln Glu Gly Asn Ala Leu Val Ile Thr Asn Lys Asp Asp Gly Asn Ala
        1675                1680                1685

GCG ATG GTC TTT AAT AAC GAG AAA AAT ATG CTT GTT CTC AGT GAT AAA    6169
Ala Met Val Phe Asn Asn Glu Lys Asn Met Leu Val Leu Ser Asp Lys
    1690                1695                1700

AAG GCA AAA CCA AGA GCG GTT CTT GAT GGA CAA AAT GGG GCA TTA ACT    6217
Lys Ala Lys Pro Arg Ala Val Leu Asp Gly Gln Asn Gly Ala Leu Thr
1705                1710                1715                1720

TTA GTC GGC AAT GAT GAT TCT CAA GTC ACC CTT TCC TCT AAG AAA GGT    6265
Leu Val Gly Asn Asp Asp Ser Gln Val Thr Leu Ser Ser Lys Lys Gly
                1725                1730                1735

AAA GAT ATT GAT GGA AAT GAT TTG AGC CGT CTC TCT GTG ACG ACT GAA    6313
Lys Asp Ile Asp Gly Asn Asp Leu Ser Arg Leu Ser Val Thr Thr Glu
            1740                1745                1750

AGA ACA AAT GCT GAT GGG CAA CTT GAA AAA GTG GAA ACC TCA TTT GCT    6361
Arg Thr Asn Ala Asp Gly Gln Leu Glu Lys Val Glu Thr Ser Phe Ala
        1755                1760                1765

ACA ATG GAT GAT GGC TTG AAG TTC AAA GCC GAC GGG GAT AAA GTG ATT    6409
Thr Met Asp Asp Gly Leu Lys Phe Lys Ala Asp Gly Asp Lys Val Ile
    1770                1775                1780

AAT AAG AAA CTT AAT GAA ACC GTT GAA ATT GTT GGT GAT GAG AAT GTG    6457
Asn Lys Lys Leu Asn Glu Thr Val Glu Ile Val Gly Asp Glu Asn Val
1785                1790                1795                1800

ACA ACA TCT ATT ACT GAT GAT AAT AAG GTG AAA GTT TCA CTG AAT AAG    6505
Thr Thr Ser Ile Thr Asp Asp Asn Lys Val Lys Val Ser Leu Asn Lys
                1805                1810                1815

AAA ATC GCG ATT GAT GAG GTT AAG ATT CCA AAT ACA GAT CCT GAT GCT    6553
Lys Ile Ala Ile Asp Glu Val Lys Ile Pro Asn Thr Asp Pro Asp Ala
            1820                1825                1830
```

```
CAA AAG GGA GAT AGC ATT GTA ATC AAC AAT GGT GGA ATC CAC GCA GGT    6601
Gln Lys Gly Asp Ser Ile Val Ile Asn Asn Gly Gly Ile His Ala Gly
        1835                1840                1845

AAT AAA GTG ATT ACT GGC GTT AAA GCG AGT GAT GAC CCA ACC AGT GCG    6649
Asn Lys Val Ile Thr Gly Val Lys Ala Ser Asp Asp Pro Thr Ser Ala
1850                1855                1860

GTG AAT CGA GGT CAA TTA AAT ACT GTG ATT GAT AAT GTT CAA AAT AAT    6697
Val Asn Arg Gly Gln Leu Asn Thr Val Ile Asp Asn Val Gln Asn Asn
1865                1870                1875                1880

TTC AAT CAA GTT AAT CAA CGT ATT GGC GAT TTA ACA CGG GAG TCG CGT    6745
Phe Asn Gln Val Asn Gln Arg Ile Gly Asp Leu Thr Arg Glu Ser Arg
            1885                1890                1895

GCA GGT ATT GCA GGT GCA ATG GCG ACG GCA AGC CTA CAA AAT GTT GCT    6793
Ala Gly Ile Ala Gly Ala Met Ala Thr Ala Ser Leu Gln Asn Val Ala
        1900                1905                1910

TTA CCA GGG AAA ACA ACG ATT TCC GTA GGT ACA GCA ACG TTC AAA GGG    6841
Leu Pro Gly Lys Thr Thr Ile Ser Val Gly Thr Ala Thr Phe Lys Gly
        1915                1920                1925

GAG AAT GCT GTT GCA ATA GGG ATG TCT AGA CTC TCT GAT AAT GGA AAA    6889
Glu Asn Ala Val Ala Ile Gly Met Ser Arg Leu Ser Asp Asn Gly Lys
1930                1935                1940

GTA GGT ATC CGT TTA TCT GGT ATG AGT ACA AGT AAC GGA GAT AAA GGG    6937
Val Gly Ile Arg Leu Ser Gly Met Ser Thr Ser Asn Gly Asp Lys Gly
1945                1950                1955                1960

GCA GCA ATG AGT GTT GGA TTT ACC TTT TAGCCTTAAT CCATAAATAA GCAAA    6991
Ala Ala Met Ser Val Gly Phe Thr Phe
                1965

GCGAATCACC TTTGATTCGC TTTTTTTATC AGATTATGTG CCGTAAAACT CCGTCCTT     7051

GGGCGGAGAT ATAAGGCACA AACGGCGTAA GCCGTTTCAA ACCTAACTAA TCAGGTGT     7111

GTTGTTGCTC AATGTATTGG CGAATAATGG AAATTGGAGT GCCACCACAA CTCCCTGC     7171

AATAAGACGG AGACCAAAGC TGATTACCCC AAAGTTTTTT GCGGATGTTC GAGTAGTT     7231

TCTTCCTAAT CATTCGGCTT GATACACCTT TTAAACTGTT TACAAGTGTA GATACAGC     7291

CTTTCGGTGG ATATTCCACA AGTAAATGAA CATGATCGTC TTCACCGTCA AATTCAAC     7351

ATTTTGCTTT AAAATCATTG CAGACGCTTT CAAAAATCAA TTTGAGTTCG TCTAAAAT     7411

CTTTCGTAAA AACATCACAG CGATATTTTG TTACAAAGAC TAAGTGAACA TGCATATT     7471

AAACACAATG TCTAC                                                    7486
```

(2) INFORMATION FOR SEQ ID NO: 6:

(i) SEQUENCE CHARACTERISTICS:
       (A) LENGTH: 2042 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 6:

```
Met Asn Lys Val Phe Lys Ile Lys Tyr Ser Val Val Lys Gln Glu Met
1               5                   10                  15

Ile Val Val Ser Glu Leu Ala Asn Asn Lys Asp Lys Thr Ala Ser Gln
                20                  25                  30

Lys Asn Thr His Asn Thr Ala Phe Phe Gln Pro Leu Phe Thr Lys Cys
            35                  40                  45

Thr Tyr Leu Ala Leu Leu Ile Asn Ile Ala Leu Gly Ala Ser Leu Phe
        50                  55                  60
```

```
Pro Gln Leu Ala Asn Ala Lys Trp Leu Glu Val Tyr Ser Ser Ser Val
 65                  70                  75                  80

Lys Leu Ser Thr Val Ser Ala Gln Ser Asn Ser Val Asn Leu Asn Pro
                 85                  90                  95

Ser Gly Ala Glu Ser Val Gly Thr Asn Ser Pro Gln Gly Val Ala Ile
                100                 105                 110

Gly Tyr Gly Ala Thr Asn Asp Arg Ser Ala Thr Gly Ala Ile Ala Leu
            115                 120                 125

Gly Val Gly Val Lys Asn Glu Thr Leu Ala Lys Asp Ser Ile Ala Ile
            130                 135                 140

Gly Tyr Gly Ala Lys Asn Glu Ser Thr Ala Pro Ser Ser Val Thr Ile
145                 150                 155                 160

Gly Lys Gln Ala Ile Asn Arg Phe Glu Lys Ser Ile Val Met Gly Leu
                165                 170                 175

Asn Ala Tyr Thr Gln Leu Asp Pro Arg Gly Thr Ser Lys Glu Thr Arg
                180                 185                 190

Gln Gly Ser Val Val Ile Gly Glu Asn Ala Lys Ser Ala Gly Asn Gln
            195                 200                 205

Ser Val Ser Leu Gly Gln Asn Ser Trp Ser Lys Thr Asn Ser Ile Ser
            210                 215                 220

Ile Gly Ala Gly Thr Phe Ala Glu Gly Lys Ser Ser Ile Ala Ile Gly
225                 230                 235                 240

Thr Asp Lys Ile Ser Gly Thr Lys Tyr Asn Asp Lys Leu Pro Ala Thr
                245                 250                 255

Ala Trp Asn Gly Thr Gly Thr Val Pro Lys Asn Ser Ile Trp Asp Ile
                260                 265                 270

Phe Ser Glu Leu Tyr Met Gly Lys Gln Thr Asn Gly Arg Asp Tyr Asp
            275                 280                 285

Thr Thr Thr Arg Asp Pro Asn Lys Pro Glu Ala Phe Tyr Lys Phe Ser
            290                 295                 300

Asp Phe Lys Gly Lys Tyr Val Asn Thr Pro Thr Ala Ser Pro Thr Tyr
305                 310                 315                 320

Ala Gly Lys Leu Gly Ala Ile Ala Leu Gly Ser Arg Thr Ile Ala Ala
                325                 330                 335

Gly Glu Met Ser Thr Ala Val Gly Ser Leu Ala Phe Ala Leu Ala Asp
                340                 345                 350

Arg Ser Thr Ala Met Gly Leu Arg Ser Phe Val Ala Lys Asp Ala Val
            355                 360                 365

Gly Gly Thr Ala Ile Gly Glu Glu Ser Arg Thr Phe Ala Lys Asp Ser
            370                 375                 380

Val Ala Ile Gly Asn Lys Thr Glu Ala Ser Asn Ala Gly Ser Met Ala
385                 390                 395                 400

Tyr Gly Tyr Lys Ala Lys Ala Val Gly Ala Gly Ala Ile Ala Ile Gly
                405                 410                 415

Thr Glu Val Ala Ala Gly Ala Lys Phe Asn Ser His Gln Thr Gly Asn
                420                 425                 430

Leu Leu Gln Asp Asn Asn Ala Tyr Ala Thr Leu Lys Asn Ala Asp Lys
            435                 440                 445

Ser Asp Asp Thr Lys Thr Gly Asn Ala Ile Thr Val Phe Thr Gln Ser
450                 455                 460

Phe Asp Asn Met Leu Thr Asn Gly Leu Pro Leu Val Ser Glu Asn Glu
465                 470                 475                 480

Thr Tyr Leu Thr Thr Ser Ala Gly Ala Ile Lys Lys Thr Ala Thr Thr
```

```
                    485                 490                 495
Asp Ser Ser Ala Gly Gly Lys Asn Ala Ile Ala Ile Gly Ser Lys
                500                 505             510

Thr Phe Ala Ser Lys Ala Asn Ser Val Ala Leu Gly Ser Tyr Ala Leu
            515                 520                 525

Ala Asp Ala Gln Asn Ala Phe Ala Leu Gly Ser Tyr Ser Phe Val Glu
530                         535                 540

Ser Ser Ala Thr Asn Thr Ile Thr Ile Gly Val Gly Ser Tyr Ala Lys
545                 550                 555                 560

Gly Lys Asn Ser Phe Leu Gly Gly Thr Trp Ala Ser Thr Leu Ser Asp
                565                 570                 575

Arg Thr Val Val Leu Gly Asn Ser Thr Ser Ile Ser Ser Gly Ser Gln
            580                 585                 590

Asn Ala Leu Ala Ile Gly Val Asn Val Phe Ile Gly Asn Asp Ser Ala
                595                 600                 605

Ser Ser Leu Ala Leu Gly Met Gly Ser Thr Ile Ala Lys Ser Ala Lys
610                 615                 620

Ser Pro Asp Ser Leu Ala Ile Gly Lys Glu Ala Arg Ile Asp Ala Lys
625                 630                 635                 640

Asp Thr Asp Asn Gly Thr Leu Tyr Gln Pro Gln Val Tyr Asp Glu Thr
                645                 650                 655

Thr Arg Ala Phe Arg Asn Phe Asn Glu Ser Ser Asp Tyr Met Arg Gln
            660                 665                 670

Ala Met Ala Leu Gly Phe Asn Ala Lys Val Ser Arg Gly Val Gly Lys
                675                 680                 685

Met Glu Thr Gly Ile Asn Ser Met Ala Ile Gly Ala Tyr Ala Gln Ala
    690                 695                 700

Thr Leu Gln Asn Ser Thr Ala Leu Gly Val Gly Ser Lys Thr Asp Tyr
705                 710                 715                 720

Thr Trp Glu Gln Leu Glu Thr Asp Pro Trp Val Ser Glu Gly Ala Ile
                725                 730                 735

Ser Ile Pro Thr Ser Gly Lys Thr Gly Val Ile Ser Val Gly Ser Lys
            740                 745                 750

Gly Ser Glu Arg Arg Ile Val Asn Leu Ala Ser Gly Ser Ser Asp Thr
                755                 760                 765

Asp Ala Val Asn Val Ala Gln Leu Lys Thr Val Glu Glu Arg Phe Leu
770                 775                 780

Ser Glu Ile Asn Leu Leu Gln Asn Gly Gly Val Lys Tyr Leu Ser
785                 790                 795                 800

Val Glu Lys Thr Asn Ile Asn Gly Gln Ser Gly Arg Val Ala Ser Gln
                805                 810                 815

Ile Arg Lys Gly Glu Asn Tyr Glu Arg Tyr Val Lys Leu Lys Thr Gln
            820                 825                 830

Leu Leu Tyr Leu Asp Ala Arg Gly Lys Leu Asn Gly Glu Lys Phe Asp
                835                 840                 845

Gln Asn Ser Leu Asn Lys Ile Arg Ala Val Val Gln Glu Leu Glu Ala
        850                 855                 860

Glu Tyr Ser Gly Glu Leu Lys Thr Thr Ala Ser Ala Leu Asn Gln Val
865                 870                 875                 880

Ala Thr Gln Leu Glu Gln Glu Val Thr Asn Asn Phe Asp Lys Phe
                885                 890                 895

Asn Gln Tyr Lys Thr Gln Ile Glu Asn Ala Ser Asn Ala Asp Ser Ala
                900                 905                 910
```

-continued

```
Arg Asn Val Gly Gly Leu Thr Pro Gln Ala Ile Ala Gln Leu Lys Ala
        915                 920                 925
Asn Asn Asn Tyr Leu Asn Asp Gly Ala Lys Gly Gln Asp Ser Ile Ala
        930                 935                 940
Phe Gly Trp Gln Ala Lys Thr Ser Gly Ala Asn Asn Gly Leu Ala Gly
945                 950                 955                 960
Lys Gln Ala Ile Ala Ile Gly Phe Gln Ala Asn Ser Ser Ala Glu Asn
                965                 970                 975
Ala Ile Ser Ile Gly Thr Asn Ser Asp Thr Ser Met Thr Gly Ala Val
            980                 985                 990
Ala Ile Gly Lys Gly Ala Thr Val Thr Ala Gly Lys Pro Ser Ile
        995                 1000                1005
Ala Leu Gly Gln Asp Ser Thr Val Ala Asn Ser Ala Ile Ser Arg Thr
     1010                 1015                 1020
Ser Ser Pro Met Ile Asn Gly Leu Ile Phe Asn Asn Phe Ala Gly Ser
1025                 1030                 1035                 1040
Pro Glu Thr Leu Gly Val Leu Ser Ile Gly Thr Ala Gly Arg Glu Arg
                1045                 1050                 1055
Lys Ile Val Asn Val Ala Ala Gly Asp Val Ser Gln Ala Ser Thr Glu
            1060                 1065                 1070
Ala Ile Asn Gly Ser Gln Leu Tyr Ala Thr Asn Phe Met Leu Ser Lys
        1075                 1080                 1085
Val Ala Gln Ser Val Lys Ser Asn Phe Gly Gly Asn Val Asn Leu Gly
     1090                 1095                 1100
Thr Asp Gly Thr Ile Thr Phe Thr Asn Ile Gly Gly Thr Gly Gln Ala
1105                 1110                 1115                 1120
Thr Ile His Asp Ala Ile Asn Asn Val Leu Thr Lys Gly Ile Tyr Leu
                1125                 1130                 1135
Lys Ala Asp Gln Asn Asp Pro Thr Gly Asn Gln Gly Gln Lys Val Glu
            1140                 1145                 1150
Leu Gly Asn Ala Ile Thr Leu Ser Ala Thr Asn Gln Trp Ala Asn Asn
        1155                 1160                 1165
Gly Val Asn Tyr Lys Thr Asn Asn Leu Thr Thr Tyr Asn Ser Gln Asn
     1170                 1175                 1180
Gly Thr Ile Leu Phe Gly Met Arg Glu Asp Pro Ser Val Lys Gln Ile
1185                 1190                 1195                 1200
Thr Ala Gly Thr Tyr Asn Thr Thr Gly Asp Ala Asn Asn Lys Asn Gln
                1205                 1210                 1215
Leu Asn Asn Thr Leu Gln Gln Thr Thr Leu Glu Ala Thr Gly Ile Thr
            1220                 1225                 1230
Ser Ser Val Gly Ser Thr Asn Tyr Ala Gly Phe Ser Leu Gly Ala Asp
        1235                 1240                 1245
Ser Val Thr Phe Ser Lys Gly Gly Ala Gly Thr Val Lys Leu Ser Gly
     1250                 1255                 1260
Val Ser Asp Ala Thr Ala Asp Thr Asp Ala Ala Thr Leu Lys Gln Val
1265                 1270                 1275                 1280
Lys Glu Tyr Arg Thr Thr Leu Val Gly Asp Asn Asp Ile Thr Ala Ala
                1285                 1290                 1295
Asp Arg Ser Gly Gly Thr Ser Asn Gly Ile Thr Tyr Asn Leu Ser Leu
            1300                 1305                 1310
Asn Lys Gly Thr Val Ser Ala Thr Glu Glu Lys Val Val Ser Gly Lys
        1315                 1320                 1325
```

-continued

```
Thr Val Tyr Glu Ala Ile Arg Asn Ala Ile Thr Gly Asn Ile Phe Thr
    1330                1335                1340

Ile Gly Leu Asp Asp Thr Thr Leu Asn Lys Ile Asn Asn Pro Ala Asp
1345                1350                1355                1360

Gln Asp Leu Ser Asn Leu Ser Glu Ser Gly Lys Asn Ala Ile Thr Gly
            1365                1370                1375

Leu Val Asp Val Val Lys Lys Thr Asn Ser Pro Ile Thr Val Glu Pro
        1380                1385                1390

Ser Thr Asp Ser Asn Lys Lys Lys Thr Phe Thr Val Gly Val Asp Phe
    1395                1400                1405

Thr Asp Thr Ile Thr Glu Gly Asp Ala Thr Asp Lys Lys Leu Thr
    1410                1415                1420

Thr Ser Lys Ser Val Glu Ser Tyr Val Thr Asn Lys Leu Ala Asn Phe
1425                1430                1435                1440

Ser Thr Asp Ile Leu Leu Ser Asp Gly Arg Ser Gly Asn Ala Thr Thr
            1445                1450                1455

Ala Asn Asp Gly Val Gly Lys Arg Arg Leu Ser Asp Gly Phe Thr Ile
        1460                1465                1470

Lys Ser Glu Asn Phe Thr Leu Gly Ser Lys Gln Tyr Asn Gly Ser Asp
    1475                1480                1485

Ser Leu Gly Val Met Tyr Asp Asp Gln Asn Gly Val Phe Lys Leu Ser
    1490                1495                1500

Leu Asn Met Thr Ala Leu Thr Thr Ser Leu Ala Asn Thr Phe Ala Lys
1505                1510                1515                1520

Leu Asp Ala Ser Asn Leu Thr Asp Asp Ser Asn Lys Glu Lys Trp Arg
            1525                1530                1535

Thr Ala Leu Asn Val Tyr Ser Lys Thr Glu Val Asp Ala Glu Ile Gln
        1540                1545                1550

Lys Ser Lys Val Thr Leu Thr Pro Asp Ser Gly Leu Ile Phe Ala Thr
    1555                1560                1565

Lys Gln Ala Gly Ser Gly Asn Asn Ala Gly Ile Asp Ala Gly Asn Lys
    1570                1575                1580

Lys Ile Ser Asn Val Ala Asp Gly Asp Ile Ser Pro Thr Ser Gly Asp
1585                1590                1595                1600

Val Val Thr Gly Arg Gln Leu Tyr Ala Leu Met Gln Lys Gly Ile Arg
            1605                1610                1615

Val Tyr Gly Asp Glu Val Ser Pro Thr Lys Thr Gln Thr Thr Ala Pro
        1620                1625                1630

Thr Asn Ala Asn Pro Thr Ala Thr Thr Ala Pro Thr Ala Ser Ser Thr
    1635                1640                1645

Gln Gly Trp Ala Thr Thr Ala Asn Thr Ala Gly Gly Val Ala Pro Ala
    1650                1655                1660

Gly Asn Val Ala Thr Gly Asp Ile Ala Pro Thr Gln Pro Thr Leu Pro
1665                1670                1675                1680

Glu Met Asn Thr Ala Leu Val Asp Asp His Leu Ala Val Pro Leu Gly
            1685                1690                1695

Gly Ser Leu Lys Ile His Gly Asp His Asn Val Lys Thr Thr Ile Ser
        1700                1705                1710

Ala Asp Asn Gln Val Gly Ile Ser Leu Gln Pro Asn Ile Ser Ile Glu
    1715                1720                1725

Asn Asn Leu Val Ile Gly Ser Asn Asp Pro Glu Lys Ala Lys Leu Ala
    1730                1735                1740

Ala Gln Glu Gly Asn Ala Leu Val Ile Thr Asn Lys Asp Asp Gly Asn
```

```
                    1745            1750            1755            1760

Ala Ala Met Val Phe Asn Asn Glu Lys Asn Met Leu Val Leu Ser Asp
                1765            1770            1775

Lys Glu Ala Lys Pro Arg Val Leu Leu Asp Gly Gln Asn Gly Ala Leu
            1780            1785            1790

Thr Leu Val Gly Asn Asp Asp Ser Gln Val Thr Leu Ser Ser Lys Lys
        1795            1800            1805

Gly Lys Asp Ile Asp Gly Asn Asp Leu Ser Arg Leu Ser Val Thr Thr
    1810            1815            1820

Glu Arg Thr Asn Ala Asp Gly Gln Leu Glu Lys Val Glu Thr Ser Phe
1825            1830            1835            1840

Ala Thr Met Asp Asp Gly Leu Lys Phe Lys Ala Asp Gly Asp Lys Val
                1845            1850            1855

Ile Asn Lys Lys Leu Asn Glu Thr Val Glu Ile Val Gly Asp Glu Asn
            1860            1865            1870

Val Thr Thr Ser Ile Thr Asp Asp Asn Lys Val Lys Val Ser Leu Asn
        1875            1880            1885

Lys Lys Ile Ala Ile Asp Glu Val Lys Ile Pro Asn Thr Asp Pro Asp
    1890            1895            1900

Ala Gln Lys Gly Asp Ser Ile Val Ile Asn Asn Gly Gly Ile His Ala
1905            1910            1915            1920

Gly Asn Lys Val Ile Thr Gly Val Lys Ala Ser Asp Asp Pro Thr Ser
                1925            1930            1935

Ala Val Asn Arg Gly Gln Leu Asn Thr Val Ile Asp Asn Val Gln Asn
            1940            1945            1950

Asn Phe Asn Gln Val Asn Gln Arg Ile Gly Asp Leu Thr Arg Glu Ser
        1955            1960            1965

Arg Ala Gly Ile Ala Gly Ala Met Ala Thr Ala Ser Leu Gln Asn Val
    1970            1975            1980

Ala Leu Pro Gly Lys Thr Thr Ile Ser Val Gly Thr Ala Thr Phe Lys
1985            1990            1995            2000

Gly Glu Asn Ala Val Ala Ile Gly Met Ser Arg Leu Ser Asp Asn Gly
                2005            2010            2015

Lys Val Gly Ile Arg Leu Ser Gly Met Ser Thr Ser Asn Gly Asp Lys
            2020            2025            2030

Gly Ala Ala Met Ser Val Gly Phe Ser Phe
        2035            2040

(2) INFORMATION FOR SEQ ID NO: 7:

(i) SEQUENCE CHARACTERISTICS:
        (A) LENGTH: 2039 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

Met Asn Lys Val Phe Lys Ile Lys Tyr Ser Val Val Lys Gln Glu Met
 1               5                  10                  15

Ile Val Val Ser Glu Leu Ala Asn Asn Lys Asp Lys Thr Ala Ser Gln
                20                  25                  30

Lys Asn Thr His Asn Thr Ala Phe Phe Gln Pro Leu Phe Thr Lys Cys
            35                  40                  45

Thr Tyr Leu Ala Leu Leu Ile Asn Ile Ala Leu Gly Thr Ser Leu Phe
```

-continued

```
          50                      55                      60
Pro Gln Leu Ala Asn Ala Lys Phe Leu Glu Val Tyr Asn Ser Ser Val
 65                      70                      75                      80

Lys Leu Gln His Val Asn Ser Gly Val Pro Ser Asp Ser Val Asn Leu
                         85                      90                      95

Asn Pro Ser Gly Gly Glu Asn Val Gly Met Asn Ser Asn Gln Gly Val
                        100                     105                     110

Ala Ile Gly Arg Gly Ala Val Asn Asn Tyr Ser Ala Thr Gly Ser Ile
            115                     120                     125

Ala Ile Gly Gln Gly Ala Lys Asn Asp Asn Trp Ala Thr Arg Ser Ile
            130                     135                     140

Ala Ile Gly Gln Gly Ala Lys Asn Glu Ser Ile Ala Ser Asp Ser Val
145                     150                     155                     160

Ala Ile Ser Asn Ala Ile Asn Arg Phe Lys Lys Ser Ile Val Ile Gly
                165                     170                     175

Leu Asn Thr Tyr Thr Gln Leu Asp Pro Arg Arg Ala Pro Glu Ser Arg
                180                     185                     190

Gln Gly Ser Val Val Ile Gly Glu Asn Ala Lys Ser Ala Gly Asn Gln
            195                     200                     205

Ser Val Ser Leu Gly Gln Asn Ala Trp Ser Lys Thr Asn Ser Ile Ser
210                     215                     220

Ile Gly Ala Gly Thr Phe Ala Glu Gly Lys Ser Thr Ile Ala Ile Gly
225                     230                     235                     240

Thr Asp Lys Ile Leu Gly Thr Asn Tyr Asn Asp Lys Leu Pro Ala Pro
                245                     250                     255

Ser Trp Asp Gly Arg Thr Gly Lys Ala Pro Thr Asn Ser Ile Trp Asp
            260                     265                     270

Ile Phe Ser Glu Leu Tyr Met Gly Lys Lys Thr Asn Gly Thr Asp Tyr
            275                     280                     285

Asp Ala Lys Lys Asn Asp Arg Asp Pro Asn Lys Pro Glu Ala Phe Tyr
290                     295                     300

Thr Tyr Ser Asp Phe Lys Ser Arg Tyr Val Asn Asn Pro Ser Thr Ser
305                     310                     315                     320

Pro Thr Tyr Ala Ala Lys Leu Gly Ala Ile Ala Leu Gly Ser Arg Thr
                325                     330                     335

Ile Ala Ala Gly Glu Met Ser Thr Ala Val Gly Ser Leu Ala Phe Ala
            340                     345                     350

Leu Ala Asp Lys Ser Thr Ala Met Gly Leu Arg Ser Phe Val Ala Lys
            355                     360                     365

Asp Ala Val Gly Gly Thr Ala Ile Gly Glu Glu Ser Arg Thr Phe Ala
370                     375                     380

Lys Asp Ser Val Ala Ile Gly Asn Lys Thr Glu Ala Ser Asn Ala Gly
385                     390                     395                     400

Ser Met Ala Tyr Gly Tyr Lys Ala Lys Ala Val Gly Ala Gly Ala Ile
                405                     410                     415

Ala Ile Gly Ala Glu Val Ala Ala Gly Ala Glu Phe Asp Ser Ser Gln
            420                     425                     430

Ala Gly Asn Leu Leu Leu Asn Arg Gly Ala Tyr Ala Thr Leu Lys Ser
            435                     440                     445

Ala Asp Lys Ser Asp Asp Ile Lys Ala Gly Asp Ala Ile Asn Val Phe
            450                     455                     460

Thr Gln Phe Phe Asp Asn Met Leu Thr Gln Gly Ser His Leu Thr Tyr
465                     470                     475                     480
```

-continued

```
Glu Asn Thr Thr Tyr Leu Thr Thr Ser Ala Gly Asp Ile Lys Lys Thr
                485                 490                 495
Leu Ala Ala Val Gly Asp Gly Gly Lys Asn Ala Ile Ala Ile Gly Asn
            500                 505                 510
Lys Thr Phe Ala Ser Lys Ala Asn Ser Val Ala Leu Gly Ser Tyr Ala
        515                 520                 525
Leu Ala Ser Ala Gln Asn Ala Phe Ala Leu Gly Ser Tyr Ser Leu Val
    530                 535                 540
Ser Pro Leu Ala Ala Asn Thr Ile Val Ile Gly Val Gly Gly Tyr Ala
545                 550                 555                 560
Thr Gly Ser Asn Ser Phe Val Gly Gly Ser Trp Val Ser Thr Leu Ser
                565                 570                 575
Ala Arg Thr Val Val Leu Gly Tyr Ser Ala Ser Ile Ser Ser Asp Ser
            580                 585                 590
His Asp Ser Leu Ala Met Gly Val Asn Ala Phe Ile Gly Asn Gly Ser
        595                 600                 605
Asn Ser Ser Leu Ala Leu Gly Thr Gly Ser Thr Ile Ala Lys Asn Ala
    610                 615                 620
Lys Ser Pro Asp Ser Leu Ala Ile Gly Lys Asp Ser Arg Ile Asp Ala
625                 630                 635                 640
Lys Asp Thr Asp Asn Gly Val Leu Tyr Thr Pro Gln Val Tyr Asp Glu
                645                 650                 655
Thr Thr Arg Ala Phe Arg Thr Phe Asp Glu Asn Lys Asp Tyr Met Arg
            660                 665                 670
Gln Ala Met Ala Leu Gly Phe Asn Ala Lys Val Ser Arg Gly Lys Gly
        675                 680                 685
Lys Met Glu Thr Gly Ile Asn Ser Met Ala Ile Gly Ala Arg Ser Gln
    690                 695                 700
Ala Thr Leu Gln Asn Ser Thr Ala Leu Gly Val Asn Ala Lys Thr Asp
705                 710                 715                 720
Tyr Thr Trp Glu Gln Leu Glu Ala Asp Pro Trp Val Ser Lys Gly Ala
                725                 730                 735
Ile Ser Ile Pro Thr Ser Gly Lys Ile Gly Val Ile Ser Val Gly Ser
            740                 745                 750
Lys Gly Ser Glu Arg Arg Ile Val Asn Val Ala Ser Gly Ser Leu Asp
        755                 760                 765
Thr Asp Ala Val Asn Val Ala Gln Leu Lys Thr Ile Glu Glu Arg Phe
    770                 775                 780
Gln Ser Glu Ile Asp Leu Leu Gln Asn Gly Gly Val Gln Tyr Leu
785                 790                 795                 800
Ser Val Glu Lys Thr Asn Ile Asn Gly Glu Ala Gly Arg Val Ala Ser
                805                 810                 815
Gln Ile Arg Lys Gly Glu Ser Tyr Lys Arg Tyr Val Lys Leu Lys Thr
            820                 825                 830
Gln Leu Leu Tyr Leu Asp Ala Arg Lys Lys Leu Asn Gly Glu Lys Phe
        835                 840                 845
Asp Gln Thr Ser Leu Asp Lys Ile Ser Lys Ala Val Gln Glu Leu Glu
    850                 855                 860
Ala Glu Tyr Ser Gly Glu Leu Lys Thr Thr Ala Ser Glu Leu Asn Arg
865                 870                 875                 880
Val Ala Met Gln Leu Asn Ala Glu Thr Thr Val Asn Asp Phe Gly Lys
                885                 890                 895
```

```
Phe Asn Gln Tyr Lys Thr Gln Ile Glu Asn Ala Thr Asn Ala Asp Ser
            900                 905                 910
Glu Lys Asn Val Gly Gly Leu Ser Pro Gln Val Ile Ala Gln Leu Lys
        915                 920                 925
Ala Asn Asn Asn Tyr Leu Asn Asp Gly Ala Lys Gly Gln Asp Ser Ile
    930                 935                 940
Ala Phe Gly Trp Gln Ala Lys Thr Ser Glu Ala Asn Asn Gly Leu Ala
945                 950                 955                 960
Gly Lys Gln Ala Ile Ala Ile Gly Phe Gln Ala Asn Ser Ser Ala Glu
            965                 970                 975
Asn Ala Ile Ser Ile Gly Thr Asn Ser Asp Thr Ser Met Thr Gly Ala
            980                 985                 990
Val Ala Ile Gly Lys Gly Ala Thr Val Thr Ala Gly Lys Pro Ser
            995                 1000                1005
Ile Ala Leu Gly Gln Asp Ser Thr Val Ala Asn Ser Ala Ile Ser Arg
    1010                1015                1020
Thr Ser Ser Val Met Ile Asn Gly Leu Thr Phe Asn Asn Phe Ala Gly
1025                1030                1035                1040
Ser Pro Glu Thr Leu Gly Val Leu Ser Ile Gly Thr Ala Gly Lys Glu
            1045                1050                1055
Arg Lys Ile Val Asn Val Ala Ala Gly Asp Ile Ser Gln Thr Ser Thr
            1060                1065                1070
Glu Ala Ile Asn Gly Ser Gln Leu Tyr Ala Thr Asn Phe Met Leu Asn
            1075                1080                1085
Lys Leu Ala Gln Ser Val Lys Thr Asn Phe Gly Gly Asn Ala Asn Leu
            1090                1095                1100
Ala Thr Asp Gly Thr Ile Thr Phe Thr Asn Ile Gly Gly Thr Gly Gln
1105                1110                1115                1120
Asp Thr Ile His Asp Ala Ile Asn Asn Val Leu Thr Lys Leu Ile Ser
            1125                1130                1135
Leu Ser Ala Thr Glu Glu Glu Val Val Ser Gly Glu Ala Val Tyr
            1140                1145                1150
Asp Ala Leu Lys Gly Ala Lys Pro Thr Val Ser Ala Glu Ala Asn Lys
            1155                1160                1165
Gly Ile Thr Gly Leu Val Asp Val Val Lys Lys Ala Asn Ser Pro Ile
    1170                1175                1180
Thr Val Glu Pro Ser Thr Asp Asn Asn Lys Lys Lys Thr Phe Thr Val
1185                1190                1195                1200
Gly Leu Met Lys Asp Ile Glu Gly Val Asn Ser Ile Thr Phe Asp Lys
            1205                1210                1215
Ser Gly Gln Asp Leu Asn Gln Val Thr Gly Arg Met Ser Ser Ala Gly
            1220                1225                1230
Leu Thr Phe Lys Lys Gly Asp Thr Thr Asn Gly Ser Thr Thr Thr Phe
            1235                1240                1245
Ala Glu Asp Gly Leu Thr Ile Asp Ser Thr Thr Asn Ser Ala Gln Thr
            1250                1255                1260
Asn Leu Val Lys Val Ser Arg Asp Gly Phe Ser Val Lys Asn Gly Ser
1265                1270                1275                1280
Asp Glu Ser Lys Leu Ala Ser Thr Lys Leu Ser Ile Gly Ala Glu Asn
            1285                1290                1295
Ala Glu His Val Glu Val Thr Lys Ser Gly Ile Ala Leu Lys Ala Asp
            1300                1305                1310
Asn Thr Ser Asp Lys Ser Ser Ile Thr Leu Ala Gln Asp Ala Ile Thr
```

-continued

```
          1315                1320                1325
Leu Ala Gly Asn Ala Thr Gly Thr Ala Ile Lys Leu Thr Gly Val Ala
    1330                1335                1340

Asp Gly Asn Ile Thr Val Asn Ser Lys Asp Ala Val Asn Gly Gly Gln
1345                1350                1355                1360

Leu Arg Thr Leu Leu Gly Val Asp Ser Gly Ala Lys Ile Gly Gly Thr
        1365                1370                1375

Glu Lys Thr Thr Ile Ser Glu Ala Ile Ser Asp Val Lys Gln Ala Leu
    1380                1385                1390

Thr Asp Ala Thr Leu Ala Tyr Lys Ala Asp Asn Lys Asn Gly Lys Thr
        1395                1400                1405

Val Lys Leu Thr Asp Gly Leu Asn Phe Thr Ser Thr Thr Asn Ile Asp
    1410                1415                1420

Ala Ser Val Glu Asp Asn Gly Val Val Lys Phe Thr Leu Lys Asp Lys
1425                1430                1435                1440

Leu Thr Gly Leu Lys Thr Ile Ala Thr Glu Ser Leu Asn Ala Ser Gln
        1445                1450                1455

Asn Ile Ile Ala Gly Gly Thr Val Thr Val Gly Gly Glu Thr Glu Gly
        1460                1465                1470

Ile Val Leu Thr Lys Ser Gly Ser Gly Asn Asp Arg Thr Leu Ser Leu
    1475                1480                1485

Ser Gly Ala Gly Asn Ala Ala Thr Asp Gly Ile Lys Val Ser Gly Val
    1490                1495                1500

Lys Ala Gly Thr Ala Asp Thr Asp Ala Val Asn Lys Gly Gln Leu Asp
1505                1510                1515                1520

Lys Leu Phe Lys Ala Ile Asn Asp Ala Leu Gly Thr Thr Asp Leu Ala
        1525                1530                1535

Val Thr Lys Asn Pro Asn Gln Thr Ser Ile Phe Asn Pro Ile Asn Gly
        1540                1545                1550

Thr Ala Pro Thr Thr Phe Lys Asp Ala Val Asp Lys Leu Thr Thr Ala
    1555                1560                1565

Val Asn Thr Gly Trp Gly Ser Lys Val Gly Ile Leu Ala Thr Gly Ile
    1570                1575                1580

Asp Gly Ile Asp Ala Gly Asn Lys Lys Ile Ser Asn Val Ala Asp Gly
1585                1590                1595                1600

Asp Ile Ser Pro Thr Ser Gly Asp Val Val Thr Gly Arg Gln Leu Tyr
        1605                1610                1615

Ala Leu Met Gln Lys Gly Ile Arg Val Tyr Gly Asp Glu Val Ser Pro
        1620                1625                1630

Thr Lys Thr Gln Thr Thr Ala Pro Thr Ala Ser Ser Thr Gln Gly Gly
    1635                1640                1645

Ala Thr Thr Ala Asn Thr Ala Gly Gly Val Ala Pro Ala Gly Asn Val
    1650                1655                1660

Ala Thr Gly Asp Ile Ala Pro Thr Gln Pro Ala Leu Pro Glu Met Lys
1665                1670                1675                1680

Thr Ala Leu Val Gly Asp His Leu Ala Val Pro Leu Gly Gly Ser Leu
        1685                1690                1695

Lys Ile His Gly Asp His Asn Val Lys Thr Thr Ile Ser Ala Gly Asn
        1700                1705                1710

Gln Val Gly Ile Ser Leu Gln Pro Asn Ile Ser Ile Glu Asn Asn Leu
    1715                1720                1725

Val Ile Gly Ser Asn Lys Pro Glu Lys Ala Lys Leu Ala Ala Gln Glu
    1730                1735                1740
```

```
Gly Asn Ala Leu Val Ile Thr Asn Lys Asp Asp Gly Asn Ala Ala Met
1745                1750                1755                1760

Val Phe Asn Asn Glu Lys Asn Met Leu Val Leu Ser Asp Lys Lys Ala
            1765                1770                1775

Lys Pro Arg Ala Val Leu Asp Gly Gln Asn Gly Ala Leu Thr Leu Val
        1780                1785                1790

Gly Asn Asp Asp Ser Gln Val Thr Leu Ser Ser Lys Lys Gly Lys Asp
    1795                1800                1805

Ile Asp Gly Asn Asp Leu Ser Arg Leu Ser Val Thr Thr Glu Arg Thr
1810                1815                1820

Asn Ala Asp Gly Gln Leu Glu Lys Val Glu Thr Ser Phe Ala Thr Met
1825                1830                1835                1840

Asp Asp Gly Leu Lys Phe Lys Ala Asp Gly Asp Lys Val Ile Asn Lys
            1845                1850                1855

Lys Leu Asn Glu Thr Val Glu Ile Val Gly Asp Glu Asn Val Thr Thr
        1860                1865                1870

Ser Ile Thr Asp Asp Asn Lys Val Lys Val Ser Leu Asn Lys Lys Ile
    1875                1880                1885

Ala Ile Asp Glu Val Lys Ile Pro Asn Thr Asp Pro Asp Ala Gln Lys
1890                1895                1900

Gly Asp Ser Ile Val Ile Asn Asn Gly Gly Ile His Ala Gly Asn Lys
1905                1910                1915                1920

Val Ile Thr Gly Val Lys Ala Ser Asp Asp Pro Thr Ser Ala Val Asn
            1925                1930                1935

Arg Gly Gln Leu Asn Thr Val Ile Asp Asn Val Gln Asn Asn Phe Asn
        1940                1945                1950

Gln Val Asn Gln Arg Ile Gly Asp Leu Thr Arg Glu Ser Arg Ala Gly
    1955                1960                1965

Ile Ala Gly Ala Met Ala Thr Ala Ser Leu Gln Asn Val Ala Leu Pro
1970                1975                1980

Gly Lys Thr Thr Ile Ser Val Gly Thr Ala Thr Phe Lys Gly Glu Asn
1985                1990                1995                2000

Ala Val Ala Ile Gly Met Ser Arg Leu Ser Asp Asn Gly Lys Val Gly
            2005                2010                2015

Ile Arg Leu Ser Gly Met Ser Thr Ser Asn Gly Asp Lys Gly Ala Ala
        2020                2025                2030

Met Ser Val Gly Phe Thr Phe
    2035

(2) INFORMATION FOR SEQ ID NO: 8:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: peptide (vi) ORIGINAL SOURCE:

(xi) SEQUENCE DESCRIPTION: SEQ ID NO: 8:

Met Leu Phe Ser Lys Ile Ser Asp Lys Lys Asn Leu Phe Phe Phe Ile
1               5                   10                  15

Tyr Ser Ser Ile Lys Arg Lys Phe Ile Met Lys Lys Thr Leu Ile Ala
                20                  25                  30
```

```
Leu Ala Val Ile Thr Met Phe Ser Ser Ala Ala Asn Ala Ala Val Ile
            35                  40                  45
Tyr Glu Lys Glu Gly Thr Lys Ile Asp Ile Asp Gly Arg Met His Phe
        50                  55                  60
Glu Leu Arg Asn Asp Ser Gly Lys Arg Ser Asp Leu Gln Asp Ala Gly
 65                 70                  75                  80
Ser Arg Val Arg Val Arg Ala Phe Gln Glu Ile Gly Asn Gly Phe Ser
                85                  90                  95
Thr Tyr Gly Ala Val Glu Phe Arg Phe Ser Thr Lys Lys Asp Gly Ser
            100                 105                 110
Glu Gln Ser Ile Gly Ser Asp Leu Arg Ala His Arg Phe Phe Ala Gly
            115                 120                 125
Ile Lys Gln Lys Asp Ile Gly Glu Leu Thr Phe Gly Lys Gln Leu His
    130                 135                 140
Leu Gly Asp Leu Val Pro Lys Ala Asn Tyr Ser Tyr Asp Leu Gly Ala
145                 150                 155                 160
Asn Ser Phe Phe Gly Ala His Ser Lys Val Ala His Phe Ile Ser Val
                165                 170                 175
Pro Phe Asn Gly Val Arg Val Ser Ala
            180                 185
```

What is claimed is:

1. An isolated polypeptide having the amino acid sequence at the N-terminal end as shown in SEQ ID:2 from *Haemophilus paragallinarum,* said polypeptide having a molecular weight of about 130 KD and which polypeptide prevents infection and onset of avian infectious coryza.

2. The isolated polypeptide of claim 1 which is a recombinant polypeptide obtained by a genetic recombination technique.

* * * * *

UNITED STATES PATENT AND TRADEMARK OFFICE
CERTIFICATE OF CORRECTION

PATENT NO.   : 6,544,519 B1
DATED        : April 8, 2003
INVENTOR(S)  : Eiji Tokunaga It is certified that error appears in the above-identified patent and that said Letters Patent is hereby corrected as shown below:

Title page,
Item [73], Assignee, delete "Chemo-Suro" and insert therefor -- Chemo-Sero --
Item [22], PCT filed, delete "Sep. 17, 1997" and insert therefor -- Sep. 12, 1997 --

Column 2,
Line 29, delete "heast-stable" and insert -- heat stable --
Line 31, delete "erythrcytes" and insert therefor -- erythrocytes --

Column 5,
Line 39, delete "surf actant" and insert therefor -- surfactant --

Column 21,
Lines 34, 40 and 42, delete "Xpnl" and insert therefor -- Kpnl --

Sequence Listing, column 27 and 28, (2) INFORMATION FOR SEQ ID NO:1:, (ix) FEATURE:, add (A) NAME/KEY: CDS, (B) LOCATION: 243..6368
Sequence Listing, column 27 and 28, position 120, 180 and 240, insert -- T --
Sequence Listing, column 41 and 42, position 6387 and 6388, insert -- AA --
Sequence Listing, column 41 and 42, position 6447 and 6448, insert -- CG --
Sequence Listing, column 41 and 42, position 6507 and 6508, insert -- CA --
Sequence Listing, column 41 and 42, position 6567 and 6568, insert -- TC --
Sequence Listing, column 41 and 42, position 6627 and 6628, insert -- AG --
Sequence Listing, column 41 and 42, position 6687 and 6688, insert -- AT --
Sequence Listing, column 41 and 42, position 6747 and 6748, insert -- AT --
Sequence Listing, column 41 and 42, position 6807 and 6808, insert -- CT --
Sequence Listing, column 41 and 42, position 6867 and 6868, insert -- GC --
Sequence Listing, column 41 and 42, position 6927 and 6928, insert -- TG --
Sequence Listing, column 41 and 42, position 6987 and 6988, insert -- GT --
Sequence Listing, column 41 and 42, position 7047 and 7048, insert -- TC --
Sequence Listing, column 41 and 42, position 7107 and 7108, insert -- CT --
Sequence Listing, column 41 and 42, position 7167 and 7168, insert -- TT --
Sequence Listing, column 41 and 42, position 7227 and 7228, insert -- GT --
Sequence Listing, column 41 and 42, position 7287 and 7288, insert -- AG --
Sequence Listing, column 41 and 42, position 7347 and 7348, insert -- GC --
Sequence Listing, column 41 and 42, position 7407 and 7408, insert -- TG --
Sequence Listing, column 41 and 42, position 7467 and 7468, insert -- CG --
Sequence Listing, column 41 and 42, position 7527 and 7258, insert -- AA --
Sequence Listing, column 41 and 42, position 7587 and 7588, insert -- AT --
Sequence Listing, column 41 and 42, position 7647 and 7648, insert -- AT --
Sequence Listing, column 41 and 42, position 7707 and 7708, insert -- GC --

UNITED STATES PATENT AND TRADEMARK OFFICE
CERTIFICATE OF CORRECTION

PATENT NO. : 6,544,519 B1
DATED : April 8, 2003
INVENTOR(S) : Eiji Tokunaga

It is certified that error appears in the above-identified patent and that said Letters Patent is hereby corrected as shown below:

Sequence Listing, column 41 and 42, position 7767 and 7768, insert -- GG --
Sequence Listing, column 41 and 42, position 7827 and 7828, insert -- TG --
Sequence Listing, column 41 and 42, position 7887 and 7888, insert -- GT --
Sequence Listing, column 41 and 42, position 7947 and 7948, insert -- CA --
Sequence Listing, column 41 and 42, position 8007 and 8008, insert -- TT --
Sequence Listing, column 41 and 42, position 8067 and 8068, insert -- AT --
Sequence Listing, column 43 and 44, position 8127 and 8128, insert -- TA --
Sequence Listing, column 43 and 44, position 8187 and 8188, insert -- CA --
Sequence Listing, column 43 and 44, position 8247 and 8248, insert -- AT --
Sequence Listing, column 43 and 44, position 8307 and 8308, insert -- TC --
Sequence Listing, column 43 and 44, position 8367 and 8368, insert -- TA --
Sequence Listing, column 59 and 60, position 6990 and 6991, insert -- AA --
Sequence Listing, column 59 and 60, position 7050 and 7051, insert -- CA --
Sequence Listing, column 59 and 60, position 7110 and 7111, insert -- TT --
Sequence Listing, column 59 and 60, position 7170 and 7171, insert -- AA --
Sequence Listing, column 59 and 60, position 7230 and 7231, insert -- TT --
Sequence Listing, column 59 and 60, position 7290 and 7291, insert -- CA --
Sequence Listing, column 59 and 60, position 7350 and 7351, insert -- TA --
Sequence Listing, column 59 and 60, position 7410 and 7411, insert -- AG --
Sequence Listing, column 59 and 60, position 7470 and 7471, insert -- AA --
Sequence Listing, column 79 and 80, (2) INFORMATION FOR SEQ ID NO:8:,
(vi) ORIGINAL SOURCE:, add "Haemophilus paragallinarum serotype A strain 221"

Signed and Sealed this

Seventeenth Day of August, 2004

JON W. DUDAS
*Acting Director of the United States Patent and Trademark Office*